US010219902B2

(12) United States Patent
Machold et al.

(10) Patent No.: US 10,219,902 B2
(45) Date of Patent: Mar. 5, 2019

(54) DEVICES, SYSTEMS, AND METHODS FOR RESHAPING A HEART VALVE ANULUS, INCLUDING THE USE OF A BRIDGE IMPLANT HAVING AN ADJUSTABLE BRIDGE STOP

(71) Applicant: MVRX, INC., San Mateo, CA (US)

(72) Inventors: Timothy R. Machold, San Mateo, CA (US); David J. Scott, Redwood City, CA (US); David A. Rahdert, San Francisco, CA (US); David R. Tholfsen, San Leandro, CA (US); Robert T. Chang, Belmont, CA (US); John A. Macoviak, La Jolla, CA (US)

(73) Assignee: MVRx, Inc., San Mateo, CA (US)

( * ) Notice: Subject to any disclaimer, the term of this patent is extended or adjusted under 35 U.S.C. 154(b) by 16 days.

(21) Appl. No.: 15/431,450

(22) Filed: Feb. 13, 2017

(65) Prior Publication Data
US 2017/0216031 A1 Aug. 3, 2017

Related U.S. Application Data

(60) Division of application No. 14/751,574, filed on Jun. 26, 2015, now Pat. No. 9,597,184, which is a
(Continued)

(51) Int. Cl.
*A61F 2/24* (2006.01)
*A61B 17/00* (2006.01)
(Continued)

(52) U.S. Cl.
CPC ...... *A61F 2/2445* (2013.01); *A61B 17/00234* (2013.01); *A61B 17/0401* (2013.01);
(Continued)

(58) Field of Classification Search
CPC ........ A61F 2/24; A61F 2/2451; A61F 2/2445; A61B 17/00243; A61B 17/00234; A61B 2017/00237
See application file for complete search history.

(56) References Cited

U.S. PATENT DOCUMENTS

| 4,056,854 A | 11/1977 | Boretos et al. |
| 4,275,469 A | 6/1981 | Gabbay |
| | (Continued) | |

FOREIGN PATENT DOCUMENTS

| WO | 2003055417 | 7/2003 |
| WO | 2004045463 | 6/2004 |

OTHER PUBLICATIONS

Alvarez et al., "Technical Improvements in the Repair of Acute Postinfarction Ventricular Septal Rupture.", J Card Surg., vol. 7, No. 3, Sep. 1992, pp. 198-202.
(Continued)

*Primary Examiner* — Jason-Dennis Stewart
(74) *Attorney, Agent, or Firm* — Kilpatrick Townsend & Stockton LLP

(57) ABSTRACT

Implants or systems of implants and methods apply a selected force vector or a selected combination of force vectors within or across the left atrium, which allow mitral valve leaflets to better coapt. The implants or systems of implants and methods make possible rapid deployment, facile endovascular delivery, and full intra-atrial adjustability and retrievability years after implant. The implants or systems of implants and methods also make use of strong fluoroscopic landmarks. The implants or systems of implants and methods make use of an adjustable implant and a fixed length implant. The implants or systems of implants
(Continued)

and methods may also utilize an adjustable bridge stop to secure the implant, and the methods of implantation employ various tools.

25 Claims, 35 Drawing Sheets

Related U.S. Application Data continuation of application No. 13/210,097, filed on Aug. 15, 2011, now Pat. No. 9,179,896, which is a continuation of application No. 11/255,663, filed on Oct. 21, 2005, now abandoned, which is a continuation-in-part of application No. 11/089,949, filed on Mar. 25, 2005, now abandoned.

(51) Int. Cl.
  *A61B 17/04* (2006.01)
  *A61B 17/06* (2006.01)

(52) U.S. Cl.
  CPC ........ *A61B 17/0487* (2013.01); *A61F 2/2451* (2013.01); *A61F 2/2466* (2013.01); *A61F 2/2487* (2013.01); *A61B 2017/00252* (2013.01); *A61B 2017/00867* (2013.01); *A61B 2017/00876* (2013.01); *A61B 2017/0417* (2013.01); *A61B 2017/0419* (2013.01); *A61B 2017/0453* (2013.01); *A61B 2017/0462* (2013.01); *A61B 2017/0464* (2013.01); *A61B 2017/06176* (2013.01); *A61F 2210/009* (2013.01); *A61F 2250/0012* (2013.01)

(56) References Cited

U.S. PATENT DOCUMENTS

| | | | |
|---|---|---|---|
| 4,994,069 A | 2/1991 | Ritchart et al. | |
| 5,360,444 A | 11/1994 | Kusuhara | |
| 5,370,685 A | 12/1994 | Stevens | |
| 5,545,241 A | 8/1996 | Vanderauwera et al. | |
| 5,716,397 A | 2/1998 | Myers | |
| 5,776,189 A | 7/1998 | Khalid | |
| 5,792,155 A | 8/1998 | Van Cleef | |
| 5,830,224 A | 11/1998 | Cohn et al. | |
| 5,851,185 A | 12/1998 | Berns | |
| 5,855,601 A | 1/1999 | Bessler et al. | |
| 5,961,440 A | 10/1999 | Schweich, Jr. et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,099,542 A | 8/2000 | Cohn et al. | |
| 6,102,932 A | 8/2000 | Kurz | |
| 6,162,168 A | 12/2000 | Schweich, Jr. et al. | |
| 6,165,119 A | 12/2000 | Schweich, Jr. et al. | |
| 6,183,411 B1 | 2/2001 | Mortier et al. | |
| 6,210,432 B1 | 4/2001 | Solem et al. | |
| 6,231,587 B1 | 5/2001 | Makower | |
| 6,260,552 B1 | 7/2001 | Mortier et al. | |
| 6,261,222 B1 | 7/2001 | Schweich, Jr. et al. | |
| 6,287,339 B1 | 9/2001 | Vazquez et al. | |
| 6,299,637 B1 | 10/2001 | Shaolian et al. | |
| 6,312,464 B1 | 11/2001 | Navia | |
| 6,312,465 B1 | 11/2001 | Griffin et al. | |
| 6,332,864 B1 | 12/2001 | Schweich, Jr. et al. | |
| 6,332,893 B1 | 12/2001 | Mortier et al. | |
| 6,338,470 B1 | 1/2002 | Steely et al. | |
| 6,338,735 B1 | 1/2002 | Stevens | |
| 6,338,740 B1 | 1/2002 | Carpentier | |
| 6,402,781 B1 | 6/2002 | Langberg et al. | |
| 6,419,695 B1 | 7/2002 | Gabbay | |
| 6,419,696 B1 | 7/2002 | Ortiz et al. | |
| 6,440,164 B1 | 8/2002 | Dimatteo et al. | |
| 6,454,799 B1 | 9/2002 | Schreck | |
| 6,458,153 B1 | 10/2002 | Bailey et al. | |
| 6,503,272 B2 | 1/2003 | Duerig et al. | |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,629,534 B1 | 10/2003 | Goar St. et al. | |
| 6,656,221 B2 | 12/2003 | Taylor et al. | |
| 6,669,709 B1 | 12/2003 | Cohn et al. | |
| 6,676,699 B2 | 1/2004 | Shiu | |
| 6,685,739 B2 | 2/2004 | Dimatteo et al. | |
| 6,702,826 B2 | 3/2004 | Liddicoat et al. | |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 6,805,711 B2 | 10/2004 | Quijano et al. | |
| 6,893,459 B1 | 5/2005 | Macoviak | |
| 6,913,608 B2 | 7/2005 | Liddicoat et al. | |
| 6,945,978 B1 | 9/2005 | Hyde | |
| 7,004,176 B2 | 2/2006 | Lau | |
| 7,070,618 B2 | 7/2006 | Streeter | |
| 7,077,862 B2 | 7/2006 | Vidlund et al. | |
| 7,166,126 B2 | 1/2007 | Spence et al. | |
| 7,967,808 B2 | 6/2011 | Fitzgerald et al. | |
| 8,956,407 B2 | 2/2015 | Macoviak et al. | |
| 9,179,891 B2 | 11/2015 | Sasady | |
| 2001/0010017 A1 | 7/2001 | Letac et al. | |
| 2001/0021872 A1 | 9/2001 | Bailey et al. | |
| 2001/0051824 A1 | 12/2001 | Hopkins et al. | |
| 2002/0026233 A1* | 2/2002 | Shaknovich | A61F 2/24 623/1.24 |
| 2002/0032481 A1 | 3/2002 | Gabbay | |
| 2002/0065554 A1 | 5/2002 | Streeter et al. | |
| 2002/0094573 A1 | 7/2002 | Bell | |
| 2002/0123802 A1 | 9/2002 | Snyders | |
| 2002/0129820 A1 | 9/2002 | Ryan et al. | |
| 2002/0138138 A1 | 9/2002 | Yang | |
| 2002/0183841 A1* | 12/2002 | Cohn | A61F 2/2451 623/2.36 |
| 2003/0014104 A1 | 1/2003 | Cribier | |
| 2003/0040792 A1 | 2/2003 | Gabbay | |
| 2003/0069593 A1 | 4/2003 | Tremulis et al. | |
| 2003/0078465 A1 | 4/2003 | Pai et al. | |
| 2003/0120340 A1 | 6/2003 | Liska et al. | |
| 2003/0139819 A1 | 7/2003 | Beer et al. | |
| 2003/0181928 A1 | 9/2003 | Vidlund et al. | |
| 2003/0199974 A1 | 10/2003 | Lee et al. | |
| 2003/0233022 A1 | 12/2003 | Vidlund et al. | |
| 2004/0148019 A1 | 7/2004 | Vidlund et al. | |
| 2004/0162610 A1 | 8/2004 | Liska et al. | |
| 2004/0243230 A1 | 12/2004 | Navia et al. | |
| 2004/0260317 A1 | 12/2004 | Bloom et al. | |
| 2005/0010277 A1 | 1/2005 | Chuter | |
| 2005/0055089 A1 | 3/2005 | Macoviak et al. | |
| 2005/0075723 A1 | 4/2005 | Schroeder et al. | |
| 2005/0267571 A1 | 12/2005 | Spence et al. | |
| 2006/0241745 A1 | 10/2006 | Solem | |
| 2006/0282161 A1* | 12/2006 | Huynh | A61B 17/00234 623/2.11 |
| 2007/0282430 A1 | 12/2007 | Thommen et al. | |

OTHER PUBLICATIONS

Antunes , "Submitralleft Ventricular Aneurysms. Correction by a New Transatrial Approach.", J Thorac Cardiovasc Surg., vol. 94, No. 2, Aug. 1987, pp. 241-245.

Bailey et al., "Surgical Repair of Mitral Insufficiency.", Diseases of the Chest, vol. XIX, No. 2, Feb. 1951, pp. 125-137.

Bailey et al., "The Surgical Correction of Mitral Insufficiency by the Use of Pericardia! Grafts.", The Journal of Thoracic Surgery, vol. 28, No. 6, Dec. 1954, pp. 551-603.

Barnard et al., "A Surgical Approach to Mitral Insufficiency.", Br J Surg., vol. 48, May 1961, pp. 655-662.

(56) References Cited

OTHER PUBLICATIONS

Bolling et al., "Early Outcome of Mitral Valve Reconstruction in Patients with End-Stage Cardiomyopathy.", J Thorac Cardiovasc Surgical, vol. 109, 1995, pp. 676-683.
Bolling et al., "Intermediate-Term Outcome of Mitral Reconstruction in Cardiomyopathy.", Journal of Thoracic Cardiovascular Surgery, vol. 115, No. 2, Feb. 1998, pp. 381-388.
Cicek et al., "Left Ventricular Endoaneurysmorrhaphy: Effect on Left Ventricular Size, Shape and Function", Cardiology, vol. 88, No. 4, Jul.-Aug. 1997, pp. 340-345.
Cooley, "Repair of Postinfarction Ventricular Septal Defect", J Card Surg., vol. 9, No. 4, Jul. 1994, pp. 427-429.
Cox, "Surgical Management of Left Ventricular Aneurysms: A Clarification of the Similarities and Differences Between . . . ", Sernin Thorac Cardiovasc Surg., vol. 9, No. 2, Apr. 1997, pp. 131-138.
Daggett et al., "Surgery for Post-Myocardial Infarct Ventricular Septal Defect", Ann Surg., vol. 186, No. 3, Sep. 1977, pp. 260-271.
Daggett, "Surgical Technique for Early Repair of Posterior Ventricular Septal Rupture.", J Thorac Cardiovasc Surg., vol. 84, No. 2, Aug. 1982, pp. 306-312.
Davila et al., "A Method for the Surgical Correction of Mitral insufficiency.", Surgery, Gynecology and Obstetrics, vol. 98, No. 4, Apr. 1954, pp. 407-412.
Davila et al., "Circumferential Suture of the Mitral Ring: A Method for the Surgical Correction of Mitral Insufficiency", Journ of Thoracic Surg, vol. 30, No. 5, Nov. 1955, pp. 531-563.
Davila et al., "The Clinical and Physiological Criteria for Surgical Correction of Mitral Insufficiency", Journal of Thoracic Surg, vol. 35, No. 2, Feb. 1958, pp. 206-231.
De Silva et al., "Postinfarction Ventricular Septal Defect an Efficacious Technique for Early Surgical Repair.", J Thorac Cardiovasc Surg., vol. 97, No. 1, Jan. 1989, pp. 86-89.
Dor, "Left Ventricular Aneurysms: the Endoventrciular Circular Patch Plasty.", Semin Thorac Cardiovasc Surg., vol. 9, No. 2, Apr. 1997, pp. 123-130.
Edmunds et al., "Septal Defect.", Atlas of Cardiothoracic Surgery, 1990, 4 pages.
Fucci et al., "Improved Results with Mitral Valve Repair Using New SUrgical Techniques.", European Journal of Cardio-Throacic Surgery, vol. 9, 1995, pp. 621-626.
Glover et al., "The Treatment of Mitral Insufficiency by the Purse-String Technique.", Journal of Thoracic Surgery, vol. 33, No. 1, Jan. 1957, pp. 75-101.
Harken et al., "The Surgical Correction of Mitral Insufficiency", Surgical Forum, vol. 4, 1953, pp. 4-7.
Harken et al., "The Surgical Correction of Mitral Insufficiency", The Journal of Thoracic Surgery, vol. 28, Issue No. 6, 1954, pp. 604-627.
Harken et al., "The Surgical Correction of Mitral Insufficiency.", The Journal of Thoracic Surgery, vol. 28, No. 6, 1954, pp. 604-624.
Harlan et al., Manual of Cardiac Surgery, vol. 2, Figs. 16.3-16.4, 1981, 3 pages.
Henderson et al., "The Surgical Treatment of Mitral Insufficiency. Experimental Use of Transplanted Pericardium in Dogs", Surgery, vol. 33, Issue No. 6, 1953, pp. 858-868.

Jatene, "Left Ventricular Aneurysmectomy. Resection or Reconstruction.", J Thorac Cardiovasc Surgical, vol. 89, 1985, pp. 321-331.
Kameda et al., "Annuloplasty for Severe Mitral Regurgitation Due to Dilated Cardiomyopathy.", Ann Thorac Surg., vol. 61, 1996, pp. 1829-1832.
Kay et al., "Surgical Treatment of Mitral insufficiency.", Surgery, vol. 37, No. 5, May 1955, pp. 697-706.
Koniaris et al., "Dynamic Retention: A Technique for Closure of the Complex Abdomen in Critically Ill Patients.", Archives of Surgery, vol. 136, No. 12, Dec. 2001, pp. 1359-1362.
Kuykendall et al., "Surgical Correction of Chronic Mitral Insufficiency in Dogs.", Surgery, vol. 44, No. 4, Oct. 1958, pp. 718-725.
Liedtke et al., "Functional Reductions in Left Ventricular Volume.", Thorac Cardiovasc Surg., vol. 71, No. 2, Feb. 1976, pp. 195-206.
McKenzie et al., "Current Concepts in Surgical Correction of Acquired Mitral Insufficiency.", Circulation, vol. 28, Oct. 1963, pp. 603-616.
Moore et al., "Unsuitability of Transventricular Autogenous Slings for Diminishing Valvular Insufficiency.", Surgery, vol. 33, No. 2, Feb. 1953, pp. 173-182.
Murray et al., "Reconstruction of the Valves of the Heart.", The Canadian Medical Association Journal, vol. 38, No. 4, Apr. 1938, pp. 317-319.
Rankin et al., "A Clinical Comparison of Mitral Valve Repair Versus Vaive Replacement in Ischemic Mitral Regurgitation", J Thome Cardiovasc Surg., vol. 95, No. 2, Feb. 1988, pp. 165-177.
Saab et al., "Left Ventricular Aneurysm: A New Surgical Approach.", Thorac Cardiovasc Surg., vol. 37, No. 1, Feb. 1989, pp. 11-19.
Sakakibara, "A Surgical Approach to the Correction of Mitral Insufficiency.", Annals of Surgery. vol. 142, No. 2, 1954, pp. 196-203.
Salati et al., "Severe Diastolic Dysfunction after Endoventriculoplasty.", J Thorac Cardiovasc Surg., vol. 109, No. 4, Apr. 1995, pp. 694-701.
Skillington et al., "Surgical Treatment for Infarct-Related Ventricular Septal Defects . . . ", J Thorac Cardiovasc Surg., vol. 99, No. 5, May 1990, pp. 798-808.
Sosa et al., "Recurrent Ventricular Tachycardia Associated With Postinfarction Aneurysm. Results of Left Ventricular . . . ", J Thorac Cardiovasc Surg., vol. 103, No. 5, May 1992, pp. 855-860.
Tashiro et al., "Extended Endocardia! Repair of Postinfarction Ventricular Septal Rupture: New Operative Technique-Modification, . . . ", J Card Surg., vol. 9, No. 2, Mar. 1994, pp. 97-102.
Templeton Ill et al., "Experimental Reconstruction of Cardiac Valves by Venous and Pericardia! Grafts.", Annals of Surgery vol. 129, No. 2, Feb. 1949, pp. 161-176.
Wilson, "Studies in Experimental Mitral Obstruction in Reiation to the Surgical Treatment of Mitral Stenosis", The British, Journal of Surgery, vol. XVIII, No. 70, 1931, pp. 259-274.
Yacoub et al., "Anatomic Correction of the Syndrome of Prolapsing Right Coronary Aortic Cusp, Dilatation of the Sinus . . . ", J Thorac Cardiovasc Surg., vol. 113, No. 2, Feb. 1997, pp. 253-260.

\* cited by examiner

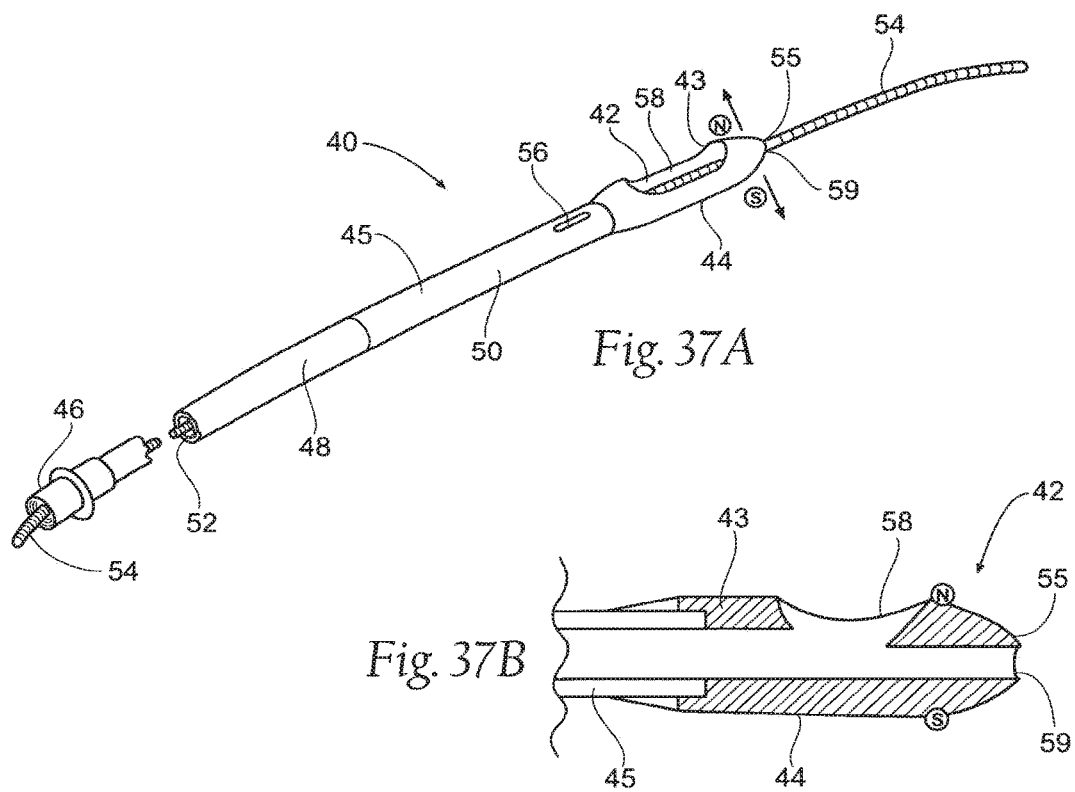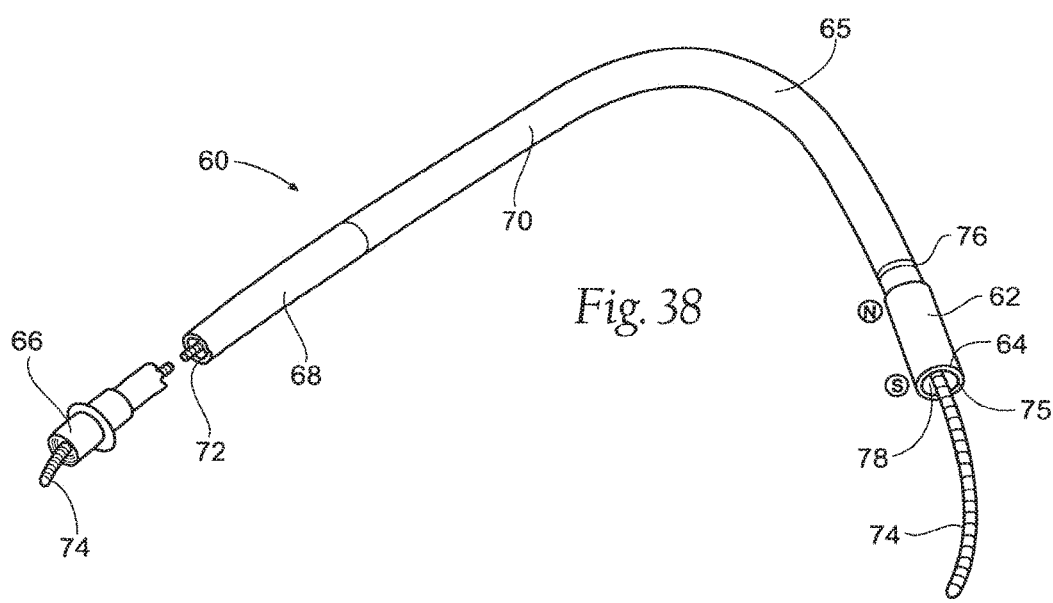

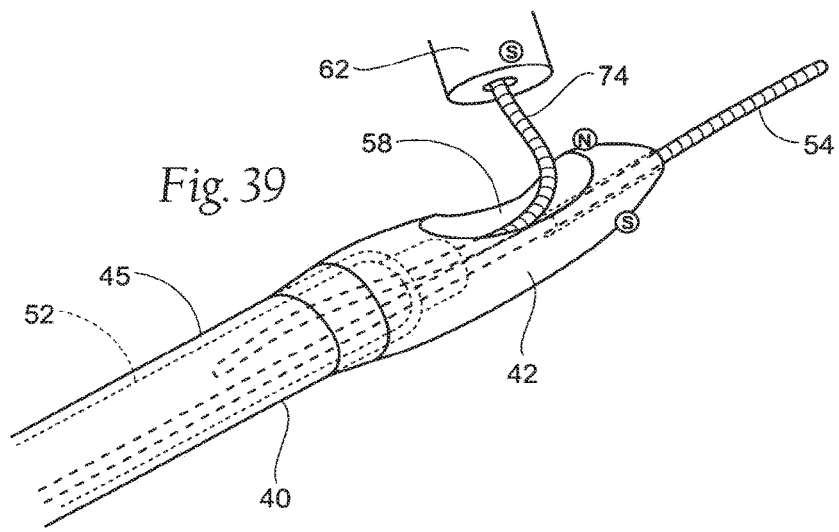
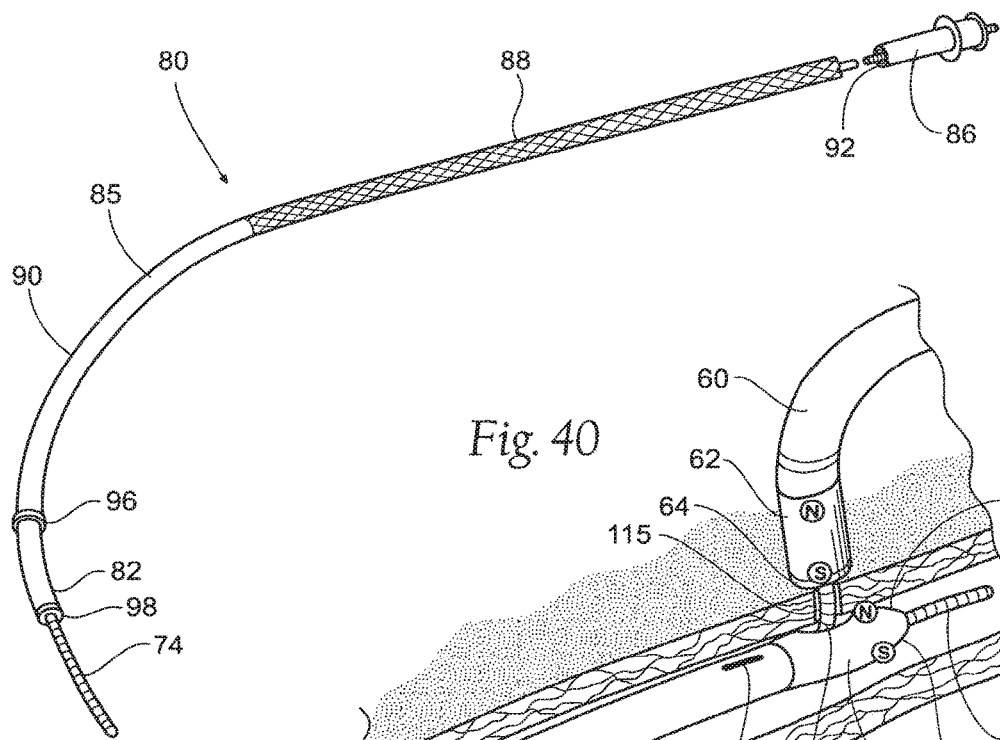
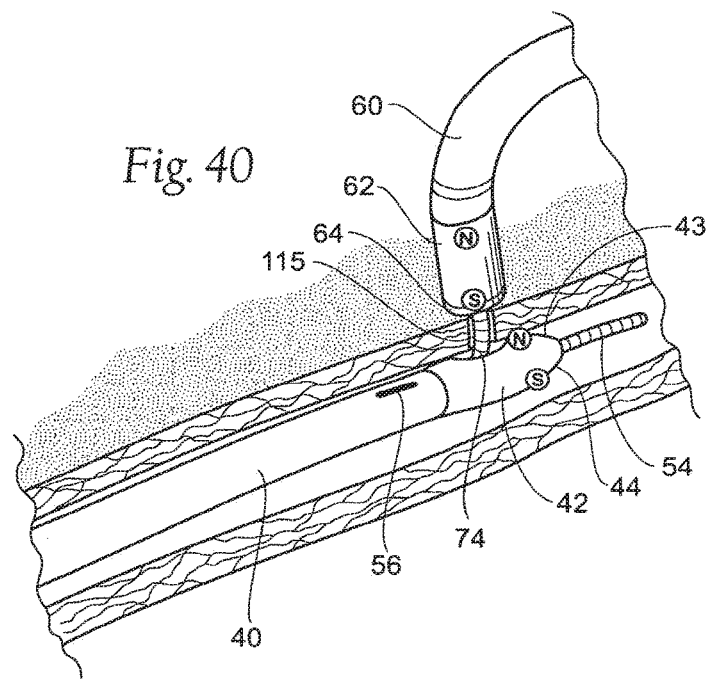

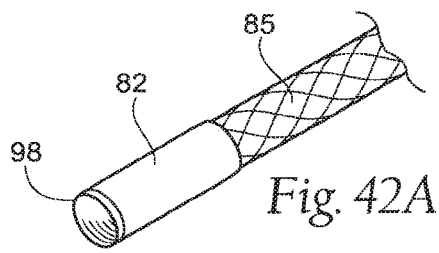
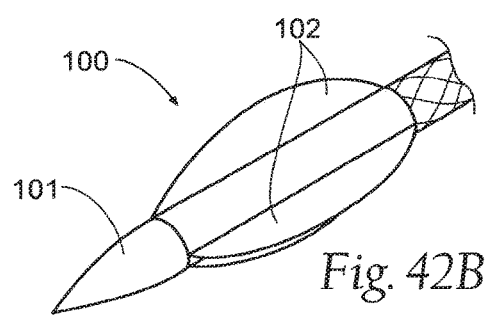
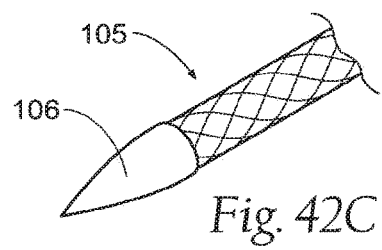
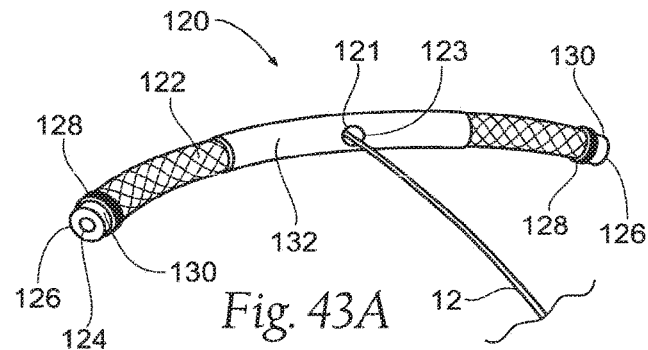
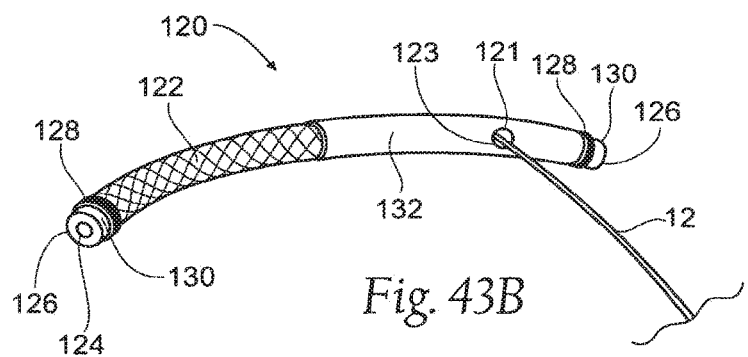

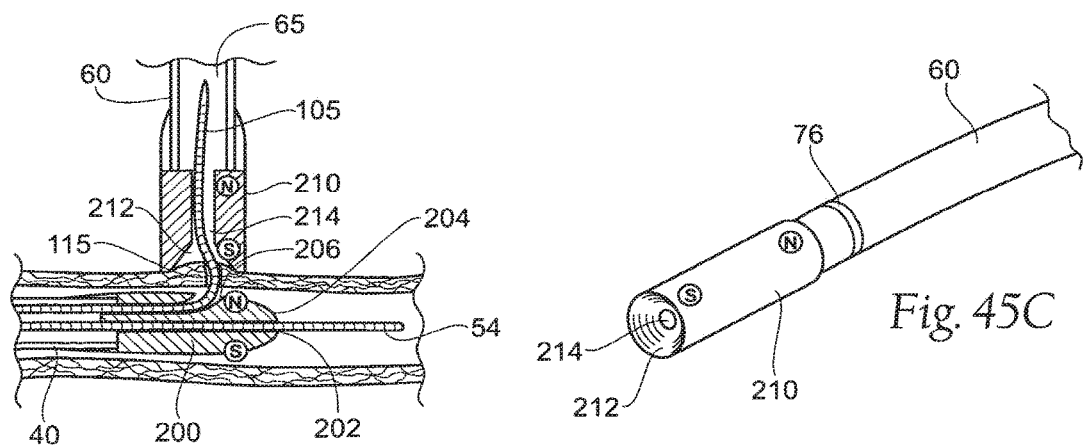
Fig. 45B
Fig. 45C
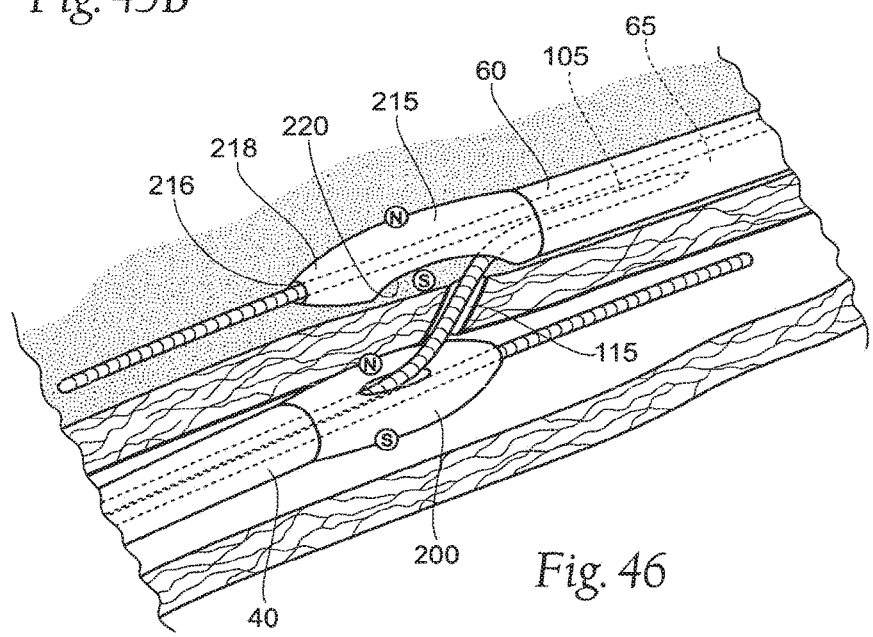
Fig. 46
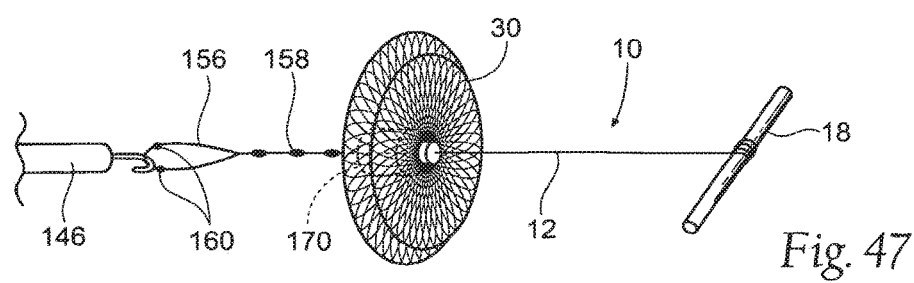
Fig. 47

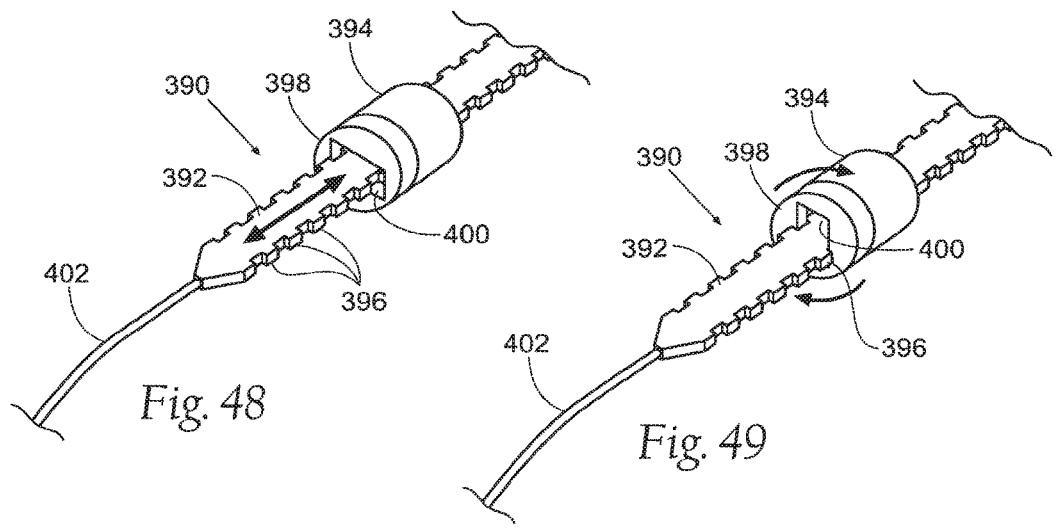
Fig. 48
Fig. 49
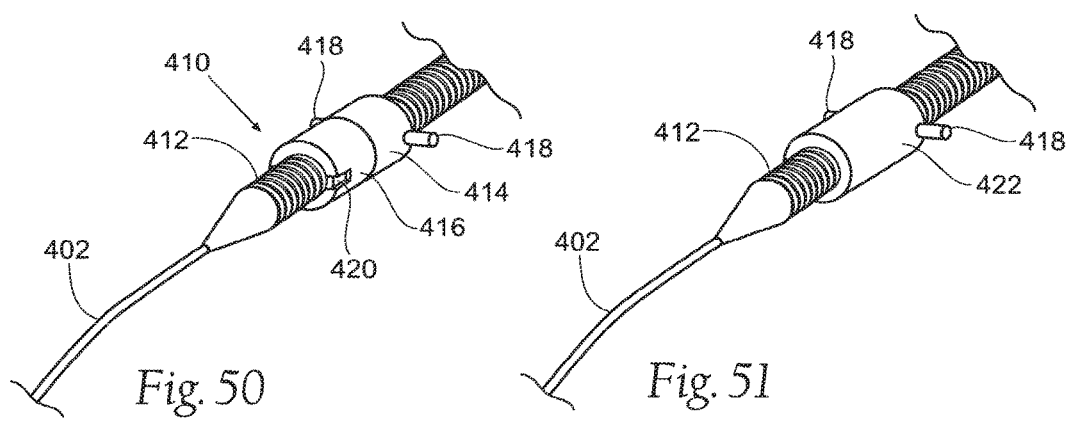
Fig. 50
Fig. 51
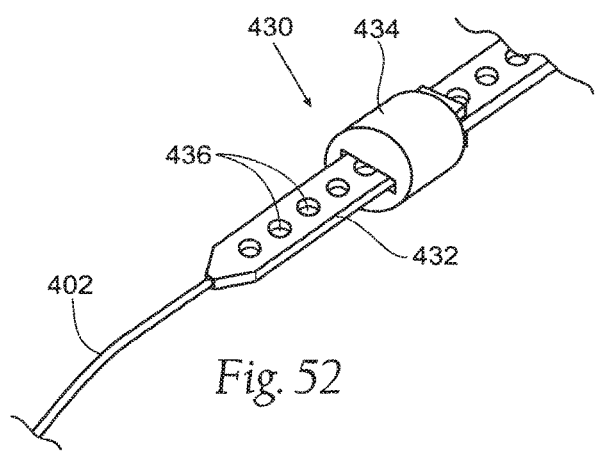
Fig. 52

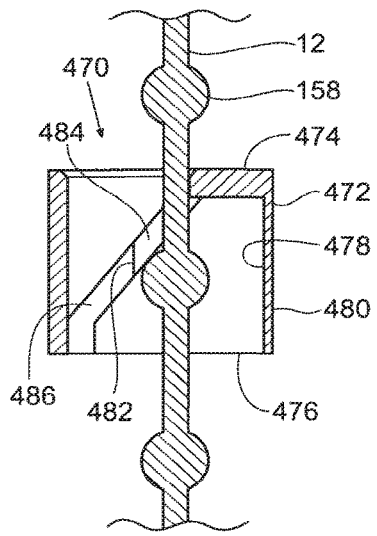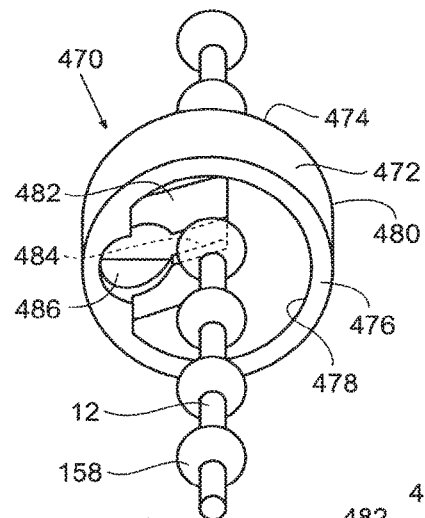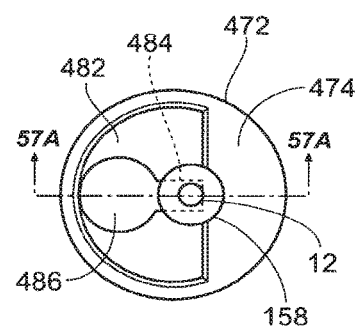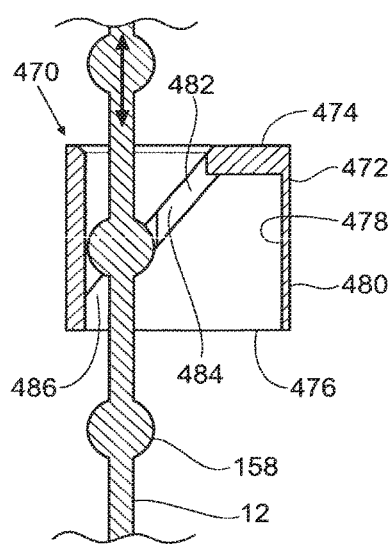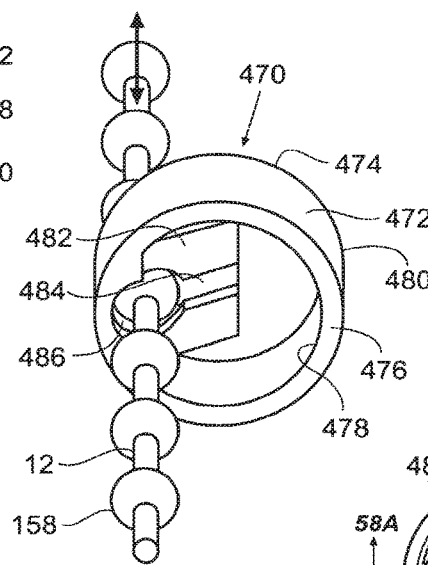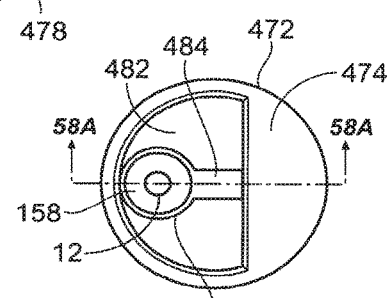
Fig. 57A
Fig. 57B
Fig. 57C
Fig. 58A
Fig. 58B
Fig. 58C

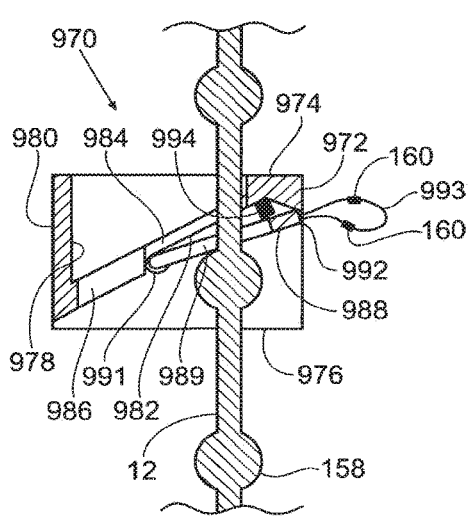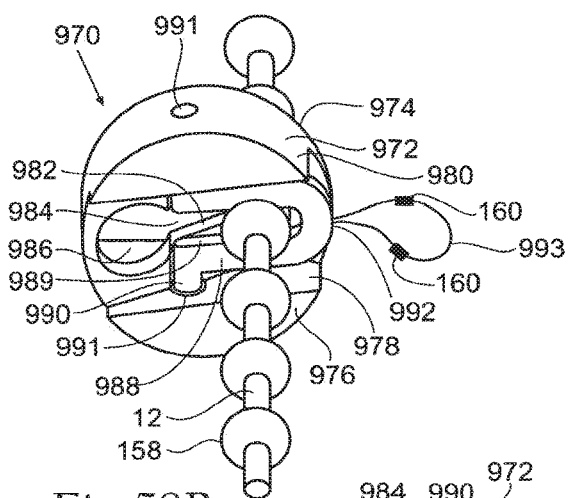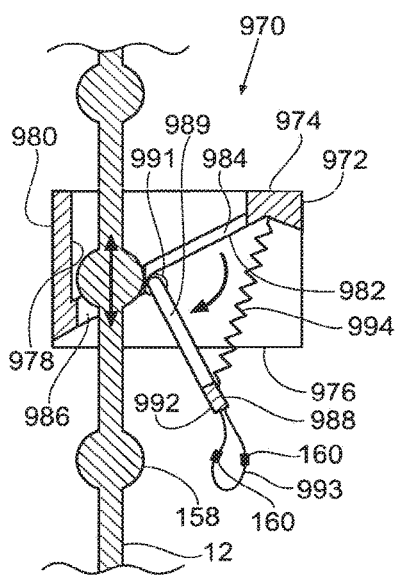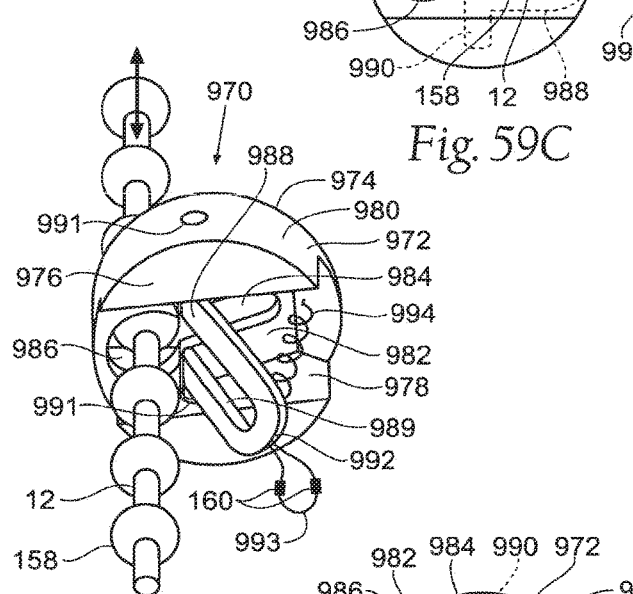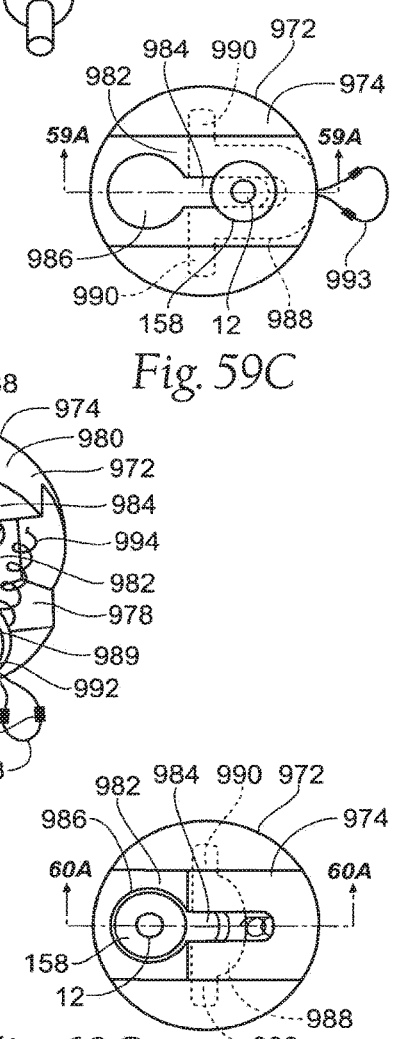
Fig. 59A
Fig. 59B
Fig. 59C
Fig. 60A
Fig. 60B
Fig. 60C

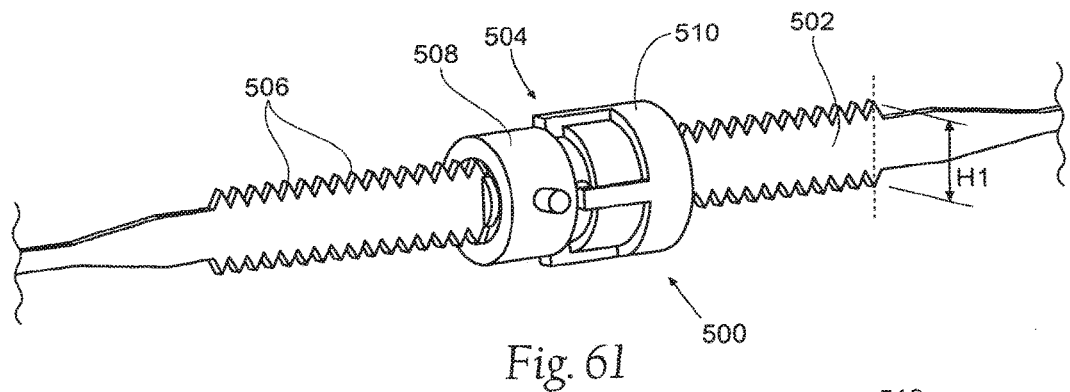
Fig. 61
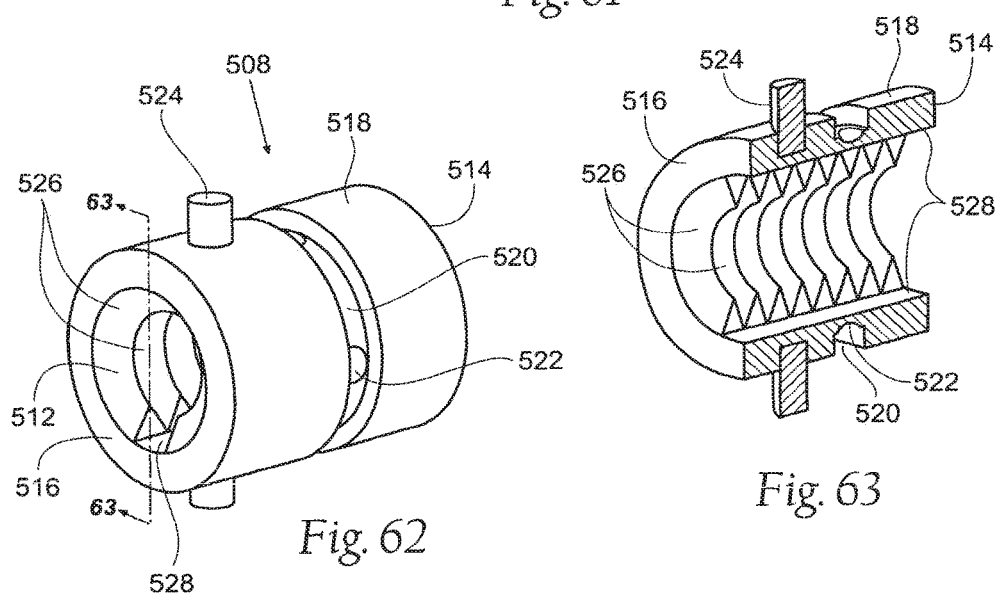
Fig. 62
Fig. 63
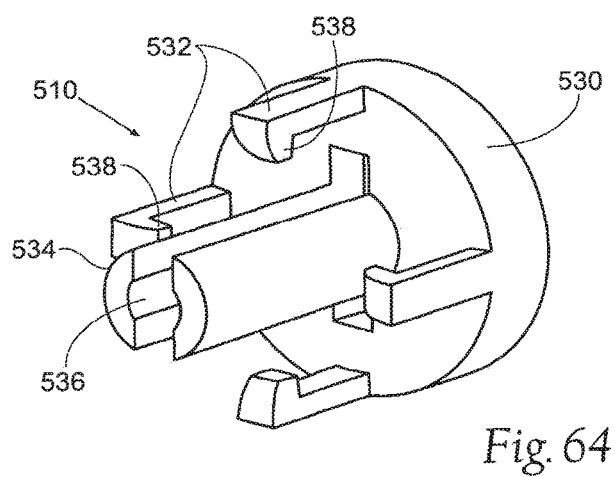
Fig. 64

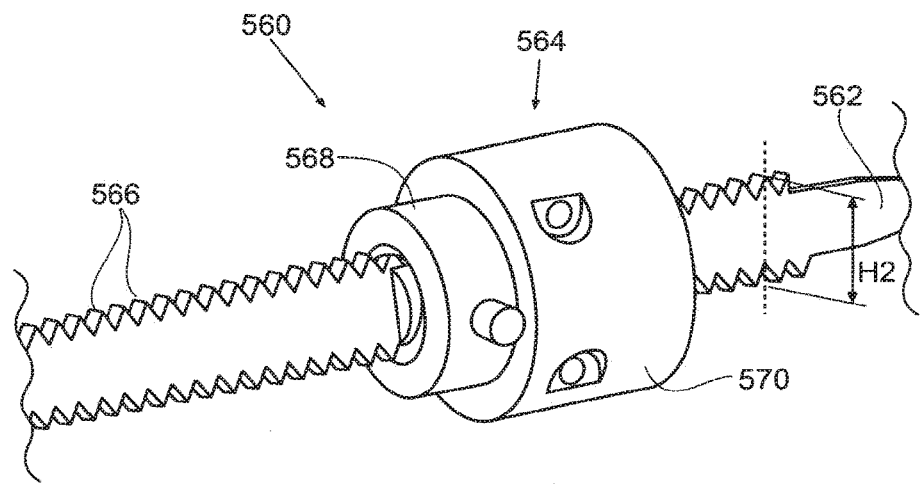
Fig. 68
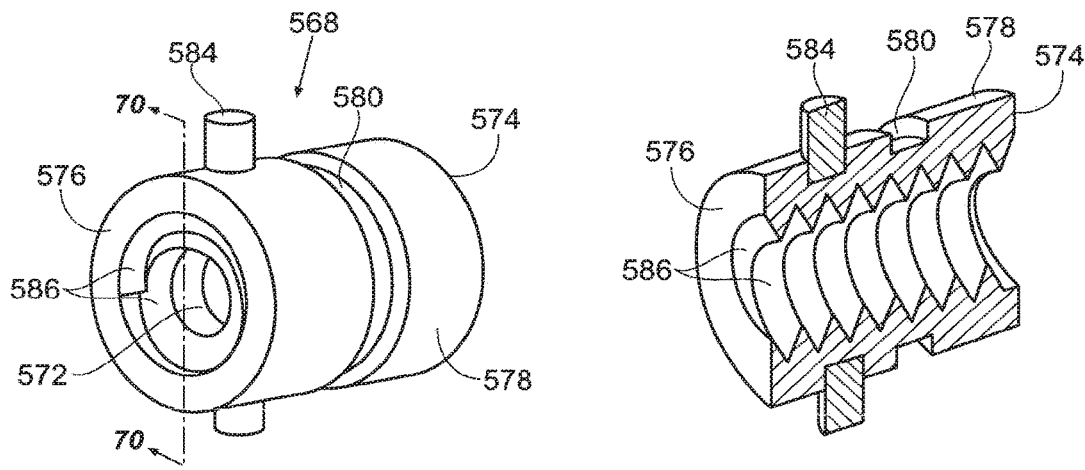
Fig. 69
Fig. 70
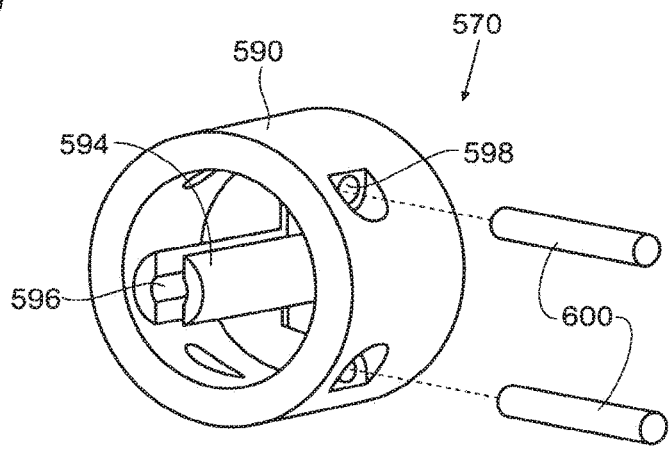
Fig. 71

DEVICES, SYSTEMS, AND METHODS FOR RESHAPING A HEART VALVE ANULUS, INCLUDING THE USE OF A BRIDGE IMPLANT HAVING AN ADJUSTABLE BRIDGE STOP

RELATED APPLICATIONS

This application is a divisional of co-pending application Ser. No. 14/751,574 filed 26 Jun. 2015, which is a continuation of application Ser. No. 13/210,097 filed 15 Aug. 2011, now U.S. Pat. No. 9,179,896 issued on 10 Nov. 2015, which is a continuation of application Ser. No. 11/255,663 filed 21 Oct. 2005, which is a continuation-in-part of Ser. No. 11/089,949, filed 25 Mar. 2005, and entitled "Devices, Systems, and Methods for Reshaping a Heart Valve Annulus, Including the Use of a Bridge Implant" which is incorporated herein by reference.

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atriums are the blood-receiving chambers, which pump blood into the ventricles. The ventricles are the blood-discharging chambers. A wall composed of fibrous and muscular parts, called the interatrial septum separates the right and left atriums (see FIGS. 2 to 4). The fibrous interatrial septum is, compared to the more friable muscle tissue of the heart, a more materially strong tissue structure in its own extent in the heart. An anatomic landmark on the interatrial septum is an oval, thumbprint sized depression called the oval fossa, or fossa ovalis (shown in FIGS. 4 and 6), which is a remnant of the oval foramen and its valve in the fetus. It is free of any vital structures such as valve structure, blood vessels and conduction pathways. Together with its inherent fibrous structure and surrounding fibrous ridge which makes it identifiable by angiographic techniques, the fossa ovalis is the favored site for trans-septal diagnostic and therapeutic procedures from the right into the left heart. Before birth, oxygenated blood from the placenta was directed through the oval foramen into the left atrium, and after birth the oval foramen closes.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atriums into the corresponding ventricles. Shortly after ventricular systole (i.e., ventricular emptying) begins, the tricuspid and mitral valves close (see FIG. 3)—to prevent back flow from the ventricles into the corresponding atriums—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

The mitral and tricuspid valves are defined by fibrous rings of collagen, each called an annulus, which forms a part of the fibrous skeleton of the heart. The annulus provides attachments for the two cusps or leaflets of the mitral valve (called the anterior and posterior cusps) and the three cusps or leaflets of the tricuspid valve. The leaflets receive chordae tendineae from more than one papillary muscle. In a healthy heart, these muscles and their tendinous chords support the mitral and tricuspid valves, allowing the leaflets to resist the high pressure developed during contractions (pumping) of the left and right ventricles. FIGS. 5 and 6 show the chordae tendineae and papillary muscles in the left ventricle that support the mitral valve.

As FIGS. 2 and 3 show, the anterior (A) portion of the mitral valve annulus is intimate with the non-coronary leaflet of the aortic valve. As FIGS. 2 and 3 also show, the mitral valve annulus is also near other critical heart structures, such as the circumflex branch of the left coronary artery (which supplies the left atrium, a variable amount of the left ventricle, and in many people the SA node) and the AV node (which, with the SA node, coordinates the cardiac cycle).

Also in the vicinity of the posterior (F) mitral valve annulus is the coronary sinus and its tributaries. These vessels drain the areas of the heart supplied by the left coronary artery. The coronary sinus and its tributaries receive approximately 85% of coronary venous blood. The coronary sinus empties into the posterior of the right atrium, anterior and inferior to the fossa ovalis (see FIG. 4). A tributary of the coronary sinus is called the great cardiac vein, which courses parallel to the majority of the posterior mitral valve annulus, and is superior to the posterior mitral valve annulus by an average distance of about 9.64+/−3.15 millimeters (Yamanouchi, Y, *Pacing and Clinical Electophysiology* 21(11):2522-6; 1998).

II. Characteristics and Causes of Mitral Valve Dysfunction

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (see FIGS. 7 and 8), the dimensions of the mitral valve annulus create an anatomic shape and tension such that the leaflets coapt, forming a tight junction, at peak contraction pressures. Where the leaflets coapt at the opposing medial (CM) and lateral (CL) sides of the annulus are called the leaflet commissures.

Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease.

Regardless of the cause (see FIG. 9), mitral valve dysfunction can occur when the leaflets do not coapt at peak contraction pressures. As FIG. 9 shows, the coaptation line of the two leaflets is not tight at ventricular systole. As a result, an undesired back flow of blood from the left ventricle into the left atrium can occur.

Mitral regurgitation is a condition where, during contraction of the left ventricle, the mitral valve allows blood to flow backwards from the left ventricle into the left atrium. This has two important consequences.

First, blood flowing back into the atrium may cause high atrial pressure and reduce the flow of blood into the left atrium from the lungs. As blood backs up into the pulmonary system, fluid leaks into the lungs and causes pulmonary edema.

Second, the blood volume going to the atrium reduces volume of blood going forward into the aorta causing low cardiac output. Excess blood in the atrium over-fills the ventricle during each cardiac cycle and causes volume overload in the left ventricle.

Mitral regurgitation is measured on a numeric Grade scale of 1+ to 4+ by either contrast ventriculography or by echocardiographic Doppler assessment. Grade 1+ is trivial regurgitation and has little clinical significance. Grade 2+ shows a jet of reversed flow going halfway back into the left atrium. Grade 3 regurgitation shows filling of the left atrium with reversed flow up to the pulmonary veins and a contrast injection that clears in three heart beats or less. Grade 4 regurgitation has flow reversal into the pulmonary veins and a contrast injection that does not clear from the atrium in three or fewer heart beats.

Mitral regurgitation is categorized into two main types, (i) organic or structural and (ii) functional. Organic mitral regurgitation results from a structurally abnormal valve component that causes a valve leaflet to leak during systole. Functional mitral regurgitation results from annulus dilation due to primary congestive heart failure, which is itself generally surgically untreatable, and not due to a cause like severe irreversible ischemic or primary valvular heart disease.

Organic mitral regurgitation is seen when a disruption of the seal occurs at the free leading edge of the leaflet due to a ruptured chord or papillary muscle making the leaflet flail; or if the leaflet tissue is redundant, the valves may prolapse the level at which coaptation occurs higher into the atrium with further prolapse opening the valve higher in the atrium during ventricular systole.

Functional mitral regurgitation occurs as a result of dilation of heart and mitral annulus secondary to heart failure, most often as a result of coronary artery disease or idiopathic dilated cardiomyopathy. Comparing a healthy annulus in FIG. 7 to an unhealthy annulus in FIG. 9, the unhealthy annulus is dilated and, in particular, the anterior-to-posterior distance along the minor axis (line P-A) is increased. As a result, the shape and tension defined by the annulus becomes less oval (see FIG. 7) and more round (see FIG. 9). This condition is called dilation. When the annulus is dilated, the shape and tension conducive for coaptation at peak contraction pressures progressively deteriorate.

The fibrous mitral annulus is attached to the anterior mitral leaflet in one-third of its circumference. The muscular mitral annulus constitutes the remainder of the mitral annulus and is attached to by the posterior mitral leaflet. The anterior fibrous mitral annulus is intimate with the central fibrous body, the two ends of which are called the fibrous trigones. Just posterior to each fibrous trigone is the commissure of which there are two, the anterior medial (CM) and the posterior lateral commissure (CL). The commissure is where the anterior leaflet meets the posterior leaflet at the annulus.

As before described, the central fibrous body is also intimate with the non-coronary leaflet of the aortic valve. The central fibrous body is fairly resistant to elongation during the process of mitral annulus dilation. It has been shown that the great majority of mitral annulus dilation occurs in the posterior two-thirds of the annulus known as the muscular annulus. One could deduce thereby that, as the annulus dilates, the percentage that is attached to the anterior mitral leaflet diminishes.

In functional mitral regurgitation, the dilated annulus causes the leaflets to separate at their coaptation points in all phases of the cardiac cycle. Onset of mitral regurgitation may be acute, or gradual and chronic in either organic or in functional mitral regurgitation.

In dilated cardiomyopathy of ischemic or of idiopathic origin, the mitral annulus can dilate to the point of causing functional mitral regurgitation. It does so in approximately twenty-five percent of patients with congestive heart failure evaluated in the resting state. If subjected to exercise, echocardiography shows the incidence of functional mitral regurgitation in these patients rises to over fifty percent.

Functional mitral regurgitation is a significantly aggravating problem for the dilated heart, as is reflected in the increased mortality of these patients compared to otherwise comparable patients without functional mitral regurgitation. One mechanism by which functional mitral regurgitation aggravates the situation in these patients is through increased volume overload imposed upon the ventricle. Due directly to the leak, there is increased work the heart is required to perform in each cardiac cycle to eject blood antegrade through the aortic valve and retrograde through the mitral valve. The latter is referred to as the regurgitant fraction of left ventricular ejection. This is added to the forward ejection fraction to yield the total ejection fraction. A normal heart has a forward ejection fraction of about 50 to 70 percent. With functional mitral regurgitation and dilated cardiomyopathy, the total ejection fraction is typically less than thirty percent. If the regurgitant fraction is half the total ejection fraction in the latter group the forward ejection fraction can be as low as fifteen percent.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

Currently, patient selection criteria for mitral valve surgery are very selective. Possible patient selection criteria for mitral surgery include: normal ventricular function, general good health, a predicted lifespan of greater than 3 to 5 years, NYHA Class III or IV symptoms, and at least Grade 3 regurgitation. Younger patients with less severe symptoms may be indicated for early surgery if mitral repair is anticipated. The most common surgical mitral repair procedure is for organic mitral regurgitation due to a ruptured chord on the middle scallop of the posterior leaflet.

In conventional annuloplasty ring repair, the posterior mitral annulus is reduced along its circumference with sutures passed through a surgical annuloplasty sewing ring cuff. The goal of such a repair is to bring the posterior mitral leaflet forward toward to the anterior leaflet to better allow coaptation.

Surgical edge-to-edge juncture repairs, which can be performed endovascularly, are also made, in which a mid valve leaflet to mid valve leaflet suture or clip is applied to keep these points of the leaflet held together throughout the cardiac cycle. Other efforts have developed an endovascular suture and a clip to grasp and bond the two mitral leaflets in the beating heart.

Grade 3+ or 4+ organic mitral regurgitation may be repaired with such edge-to-edge technologies. This is because, in organic mitral regurgitation, the problem is not the annulus but in the central valve components.

However, functional mitral regurgitation can persist at a high level, even after edge-to-edge repair, particularly in cases of high Grade 3+ and 4+ functional mitral regurgitation. After surgery, the repaired valve may progress to high rates of functional mitral regurgitation over time.

In yet another emerging technology, the coronary sinus is mechanically deformed through endovascular means applied and contained to function solely within the coronary sinus.

It is reported that twenty-five percent of the six million Americans who will have congestive heart failure will have functional mitral regurgitation to some degree. This constitutes the 1.5 million people with functional mitral regurgitation. Of these, the idiopathic dilated cardiomyopathy accounts for 600,000 people. Of the remaining 900,000 people with ischemic disease, approximately half have functional mitral regurgitation due solely to dilated annulus.

By interrupting the cycle of progressive functional mitral regurgitation, it has been shown in surgical patients, that survival is increased and in fact forward ejection fraction increases in many patients. The problem with surgical therapy is the significant insult it imposes on these chronically ill patients with high morbidity and mortality rates associated with surgical repair.

The need remains for simple, cost-effective, and less invasive devices, systems, and methods for treating dysfunction of a heart valve, e.g., in the treatment of organic and functional mitral valve regurgitation.

SUMMARY OF THE INVENTION

The invention provides devices, systems, and methods for reshaping a heart valve annulus, including the use of a bridge implant system having an adjustable bridge stop.

One aspect of the invention provides devices, systems, and methods including a bridge implant system having an adjustable bridge stop, the bridge stop comprising a bridge stop housing having a length and a width, an aperture extending through the length of the bridge stop housing, the aperture sized and configured to allow a bridging element to extend through at least a portion of the length of the aperture, and an adjustment mechanism coupled to the bridge stop housing to allow adjustment of a length of the bridging element. The adjustment mechanism may include a catheter releasably coupled to the bridge stop to activate the adjustment mechanism. In addition, the adjustment mechanism may be located within the aperture within the bridge stop housing. The adjustment mechanism may allow for only lengthening or only shortening of the bridging element, or for both lengthening and shortening of the bridging element. The adjustment mechanism may also be sized and configured to allow for repeatable adjustment. The bridge stop may also include a relocation element, and the relocation element further may include at least one radio-opaque marker.

In one embodiment, the bridge stop adjustment mechanism includes a static state, with the bridge stop adjustment mechanism restraining the bridging element in the adjustment mechanism's static state, thereby requiring a positive activation force necessary to allow the bridging element to be adjusted.

In an additional embodiment, the bridging element includes discrete stop beads to allow the bridging element to be adjusted in discrete lengths. The bridging element may also include a toothed ribbon portion or a perforated ribbon portion or a threaded shaft portion extending through at least a portion of the aperture in the bridge stop housing.

An additional aspect of the invention provides devices, systems, and methods including a bridge implant system having an adjustable bridge stop, the bridge stop comprising a bridge stop housing, the housing comprising an inner portion and an outer portion, the housing having a length and a width, an aperture extending through the length of the bridge stop housing, the aperture sized and configured to allow a bridging element to extend through at least a portion of the length of the aperture, and an adjustment mechanism coupled to the bridge stop housing to allow adjustment of the bridging element. The adjustment mechanism may comprise rotation of either the inner portion or the outer portion. In addition, the inner portion may be positioned completely within the outer portion, or the inner portion may extend partially outside the outer portion.

Yet an additional aspect of the invention provides devices, systems, and methods including a bridge implant system having an adjustable bridge stop, the bridge implant system comprising bridging element sized and configured to span a left atrium between a great cardiac vein and an interatrial septum, a first bridge stop coupled to the bridging element, and a second bridge stop coupled to the bridging element, the second bridge stop comprising, a bridge stop housing having a length and a width, an aperture extending through the length of the bridge stop housing, the aperture sized and configured to allow a bridging element to extend through at least a portion of the length of the aperture, and an adjustment mechanism coupled to the bridge stop housing to allow adjustment of the bridging element. The bridge stop housing may further comprise an inner portion and an outer portion, wherein the adjustment mechanism may comprise rotation of either the inner portion or the outer portion to allow the bridging element to be lengthened or shortened.

Yet an additional aspect of the invention provides devices, systems, and methods for adjusting a bridge stop of an implant system, the bridge stop comprising a bridge stop housing having a length and a width, an aperture extending through the length of the bridge stop housing, the aperture sized and configured to allow a bridging element to extend through at least a portion of the length of the aperture, and an adjustment mechanism coupled to the bridge stop housing to allow adjustment of a length of the bridging element. The adjustment mechanism may include a catheter releasably coupled to the bridge stop to activate the adjustment mechanism. In addition, the adjustment mechanism may be located within the aperture within the bridge stop housing. The adjustment mechanism may allow for only lengthening or only shortening of the bridging element, or for both lengthening and shortening of the bridging element. The adjustment mechanism may also be sized and configured to allow for repeatable adjustment. The bridge stop may also include a relocation element, and the relocation element further may include at least one radio-opaque marker.

Yet an additional aspect of the invention provides devices, systems, and methods for adjusting a length of a bridging element of a bridge implant system within a chamber of a heart comprising providing a bridge stop comprising a bridge stop housing having a length and a width, an aperture extending through the length of the bridge stop housing, the aperture sized and configured to allow a bridging element to extend through at least a portion of the length of the aperture, and an adjustment mechanism coupled to the bridge stop housing to allow adjustment of a length of the bridging element, and then operating the adjustment mechanism to lengthen or to shorten the bridging element.

In one aspect of the invention, the adjustment may be repeated until a desired length of the bridging element is achieved. Further, the bridging element may be allowed to settle for a predetermined time before repeating the operating the adjustment mechanism step. A catheter may be coupled to the bridge stop adjustment mechanism, the catheter being used to operate the adjustment mechanism. Alternatively a catheter may be coupled to the bridging element, the catheter being used to lengthen or shorten the bridging element.

In an additional embodiment, the devices, systems, and methods for adjusting a length of a bridging element of a bridge implant system within a chamber of a heart may further comprise providing a catheter, the catheter including a proximal end and a distal end, the catheter having a first adjustment mechanism on its proximal end and a second adjustment mechanism on its proximal end, coupling the first adjustment mechanism to one of the posterior bridge stop and the anterior bridge stop, coupling the second adjustment mechanism to the bridging element, operating the first adjustment mechanism to allow adjustment of the bridging element, operating the second adjustment mechanism to lengthen or shorten the bridging element, and operating the first adjustment mechanism again to re-secure the bridging element.

Other features and advantages of the invention shall be apparent based upon the accompanying description, drawings, and claims.

BRIEF DESCRIPTION OF THE DRAWINGS

FIG. 37A is a perspective view of a catheter used in the implantation of an implant system of the type shown in FIGS. 10A to 10C.

FIG. 37B is a partial sectional view showing a magnetic head of the catheter as shown in FIG. 37A.

FIG. 38 is a perspective view of an additional catheter which may be used in the implantation of an implant system of the type shown in FIGS. 10A to 10C.

FIG. 39 is a partial perspective view of the interaction between the magnetic head of the catheter shown in FIG. 37A and the magnetic head of the catheter shown in FIG. 38, showing a guide wire extending out of one magnetic head and into the other magnetic head.

FIG. 40 is an anatomic partial perspective view of the magnetic catheter heads shown in FIG. 39, with one catheter shown in the left atrium and one catheter shown in the great cardiac vein.

FIG. 41 is a perspective view of an additional catheter which may be used in the implantation of an implant system of the type shown in FIGS. 10A to 10C.

FIGS. 42A to 42C are partial perspective views of catheter tips which may be used with the catheter shown in FIG. 41.

FIG. 43A is a perspective view of a symmetrically shaped T-shaped bridge stop or member which may be used with the implant system of the type shown in FIGS. 10A to 10C.

FIG. 43B is a perspective view of an alternative embodiment of the T-shaped bridge stop shown in FIG. 43A, showing the bridge stop being asymmetric and having one limb shorter than the other.

FIG. 45B is a partial sectional view of the alternative magnetic catheter heads of the type shown in FIG. 45A, showing a guide wire piercing the wall of the great cardiac vein and left atrium and extending into the receiving catheter.

FIG. 45C is a partial perspective view of an alternative magnetic head of the type shown in FIG. 45B.

FIG. 46 is an anatomic partial perspective view of an additional alternative embodiment for the magnetic catheter heads of the type shown in FIG. 45A, showing a side to side configuration.

FIG. 47 is a perspective view depicting an alternative embodiment of an implant system of the type shown in FIGS. 10A to 10D, showing the use a bridge stop having a bridging element adjustment feature and also including a relocation loop.

FIG. 48 is a perspective view depicting an alternative embodiment of a bridge stop having a bridging element adjustment feature, and showing the bridging element adjustment feature in the open position.

FIG. 49 is a perspective view of the bridge stop shown in FIG. 48, showing the bridging element adjustment feature in the closed position.

FIGS. 50 through 52 are perspective views depicting alternative embodiments of a bridge stop having a bridging element adjustment feature.

FIG. 57A is a sectional view of an alternative embodiment of a bridge lock having a bridging element adjustment feature, showing the bridging element in the locked position.

FIG. 57B is a perspective view looking into the bridge lock shown in FIG. 57A, showing the bridging element in the locked position.

FIG. 57C is a top view of the bridge lock shown in FIG. 57A, showing the bridging element in the locked position.

FIG. 58A is a sectional view of the bridge lock shown in FIG. 57A, showing the bridging element in the unlocked position.

FIG. 58B is a perspective view looking into the bridge lock shown in FIG. 57A, showing the bridging element in the unlocked position.

FIG. 58C is a top view of the bridge lock shown in FIG. 57A, showing the bridging element in the unlocked position.

FIGS. 59A through 60C are views of an alternative embodiment of the bridge lock shown in FIGS. 57A through 58C, and showing the alternative bridge lock having a rotating gate to provide a convenient mechanism to reset the bridge lock for adjustment.

FIG. 61 is a perspective view of an alternative embodiment of a bridge lock, the bridge lock having a bridging element adjustment feature, and showing the bridging element adjustment feature in the open position.

FIG. 62 is a perspective view of the grooved component of the bridge lock shown in FIG. 61, and without the bridging element.

FIG. 63 is a section view of the grooved component of the bridge lock shown in FIG. 62, taken generally along line 63-63 of FIG. 62.

FIG. 64 is a perspective view of the snap component of the bridge lock shown in FIG. 61.

FIG. 68 is a perspective view of an alternative embodiment of the bridge lock shown in FIG. 61, the bridge lock having internal threads to allow for threaded bridging element adjustment.

FIG. 69 is a perspective view of the threaded component of the bridge lock shown in FIG. 68.

FIG. 70 is a section view of the threaded component of the bridge lock shown in FIG. 69, taken generally along line 70-70 of FIG. 69.

FIG. 71 is a perspective view of the hub component of the bridge lock shown in FIG. 68.

DESCRIPTION OF THE PREFERRED EMBODIMENT

Figure 1:
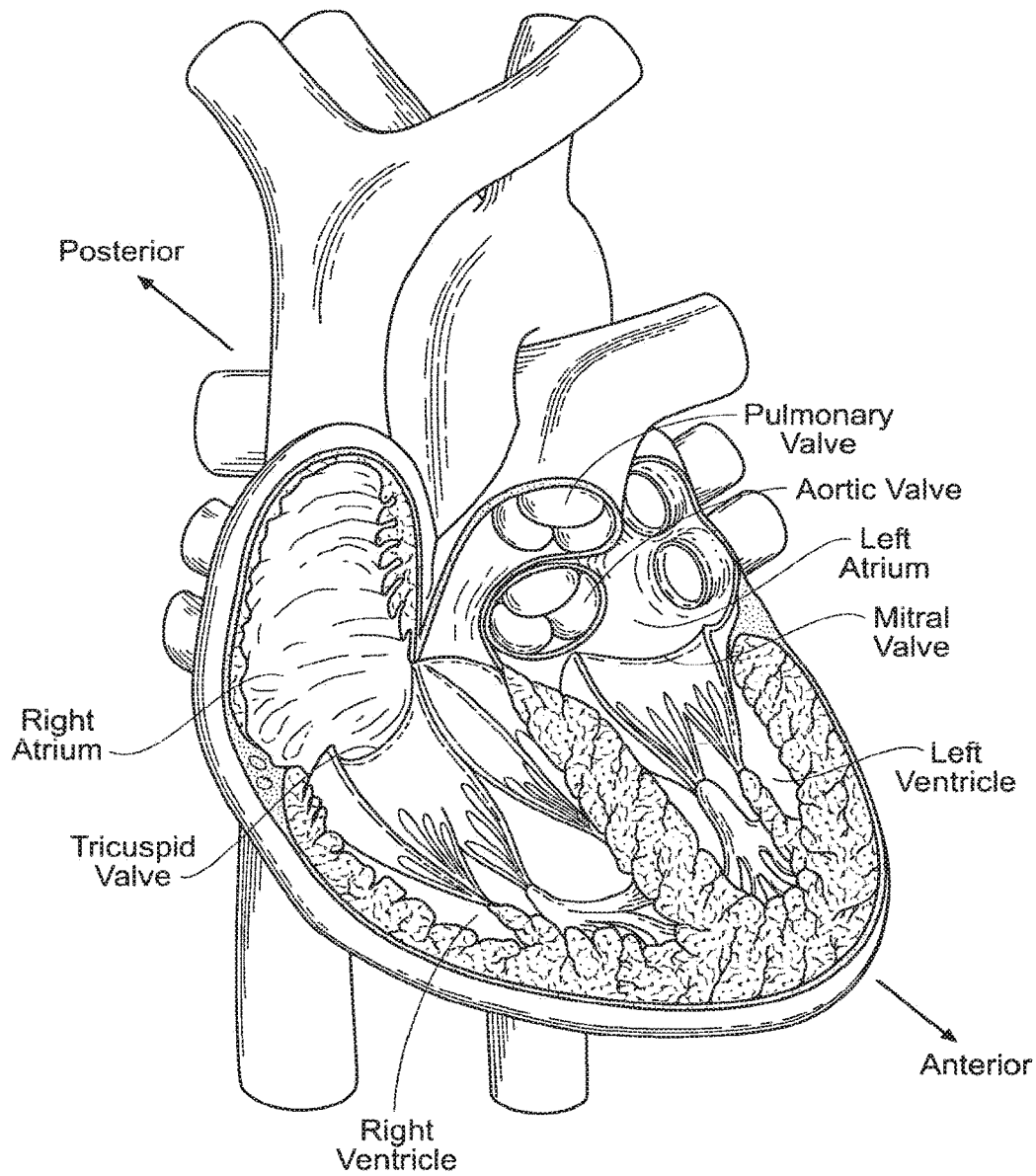
FIG. 1 is an anatomic anterior view of a human heart, with portions broken away and in section to view the interior heart chambers and adjacent structures.
Figure 2:
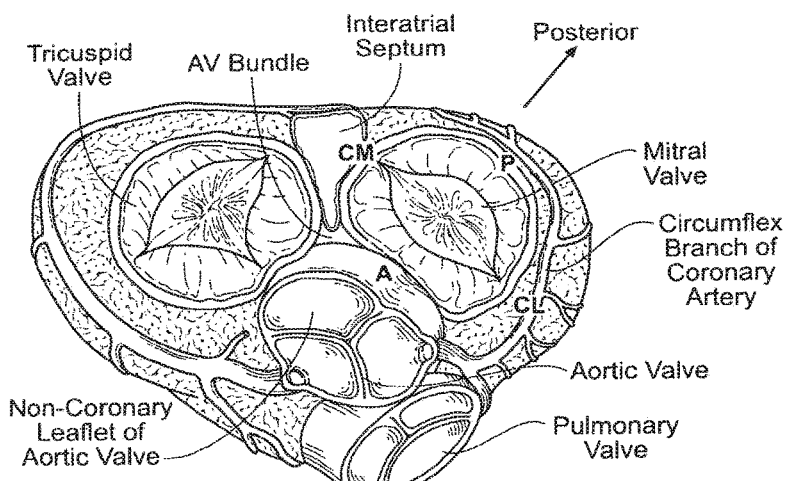
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
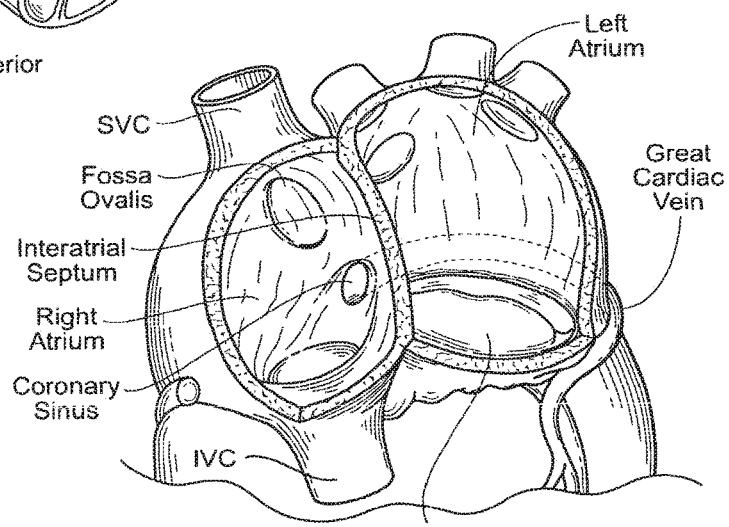
FIG. 4 is an anatomic anterior perspective view of the left and right atriums, with portions broken away and in section to show the interior of the heart chambers and associated structures, such as the fossa ovalis, coronary sinus, and the great cardiac vein.
Figure 3:
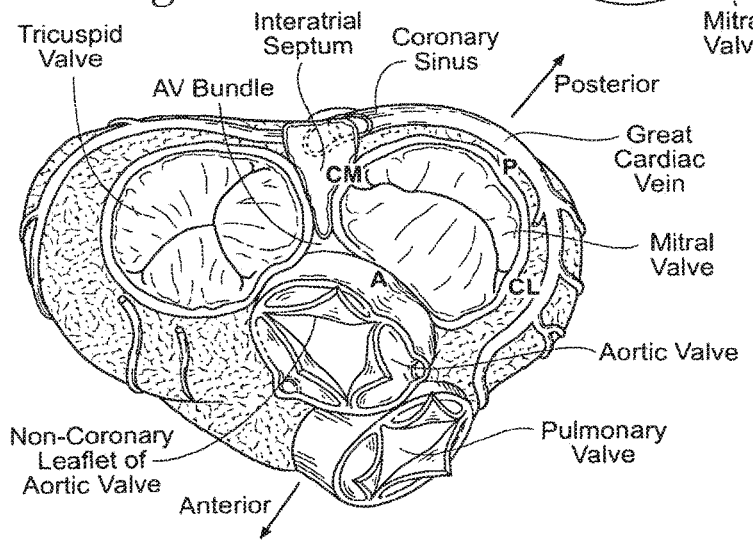
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.
Figure 5:
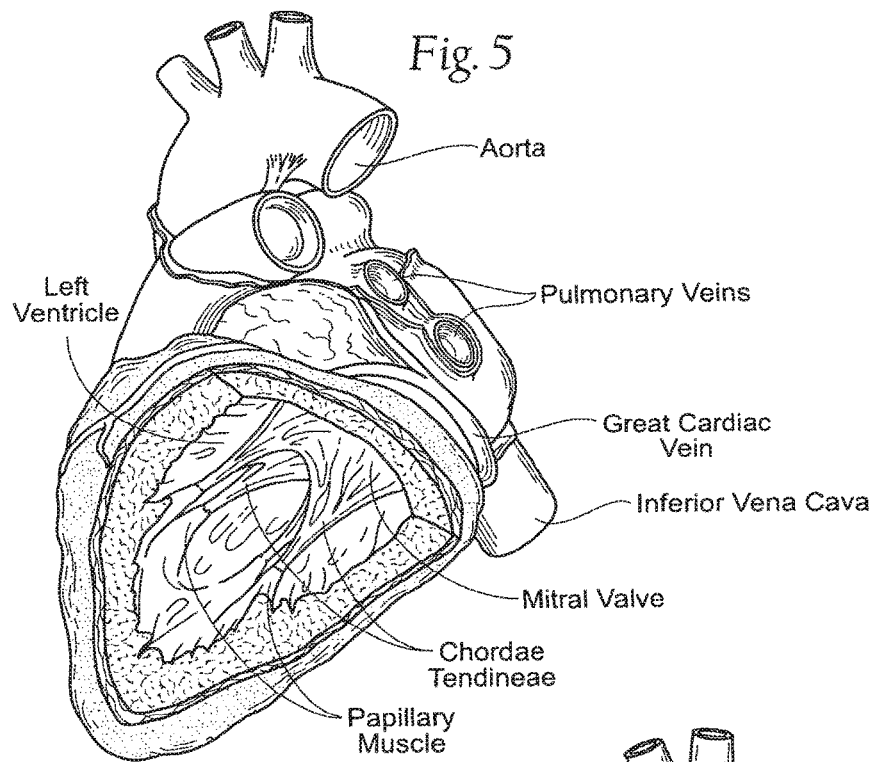
FIG. 5 is an anatomic lateral view of a human heart with portions broken away and in section to show the interior of the left ventricle and associated muscle and chord structures coupled to the mitral valve.
Figure 6:
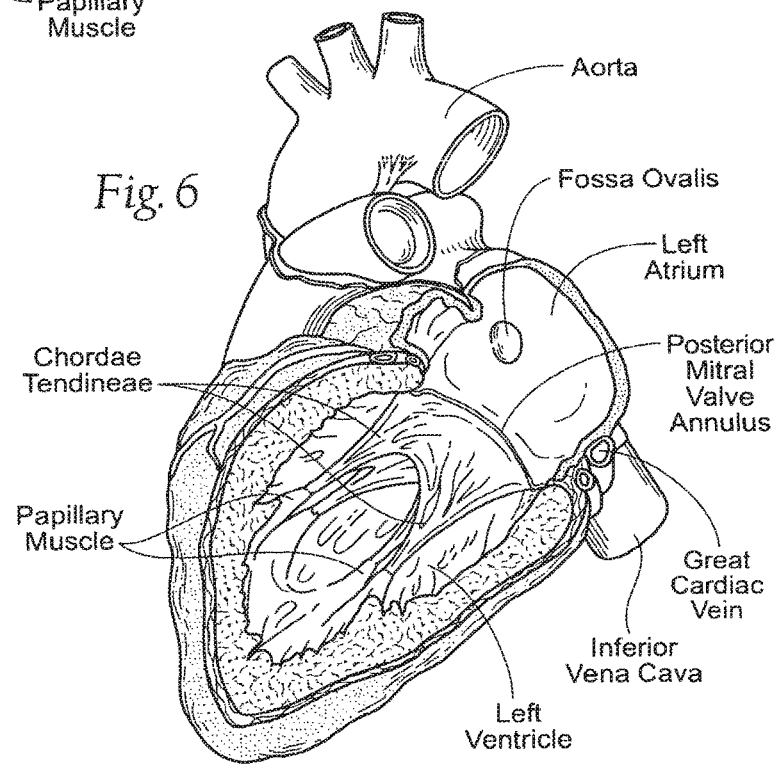
FIG. 6 is an anatomic lateral view of a human heart with portions broken away and in section to show the interior of the left ventricle and left atrium and associated muscle and chord structures coupled to the mitral valve.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

I. Trans-Septal Implants for Direct Shortening of the Minor Axis of a Heart Valve Annulus A. Implant Structure FIGS. 10A to 10D show embodiments of an implant 10 that is sized and configured to extend across the left atrium in generally an anterior-to-posterior direction, spanning the mitral valve annulus. The implant 10 comprises a spanning region or bridging element 12 having a posterior bridge stop region 14 and an anterior bridge stop region 16.

The posterior bridge stop region 14 is sized and configured to allow the bridging element 12 to be placed in a region of atrial tissue above the posterior mitral valve annulus. This region is preferred, because it generally presents more tissue mass for obtaining purchase of the posterior bridge stop region 14 than in a tissue region at or adjacent to the posterior mitral annulus. Engagement of tissue at this supra-annular location also may reduce risk of injury to the circumflex coronary artery. In a small percentage of cases, the circumflex coronary artery may pass over and medial to the great cardiac vein on the left atrial aspect of the great cardiac vein, coming to lie between the great cardiac vein and endocardium of the left atrium. However, since the forces in the posterior bridge stop region are directed upward and inward relative to the left atrium and not in a constricting manner along the long axis of the great cardiac vein, the likelihood of circumflex artery compression is less compared to other technologies in this field that do constrict the tissue of the great cardiac vein. Nevertheless, should a coronary angiography reveal circumflex artery stenosis, the symmetrically shaped posterior bridge stop may be replaced by an asymmetrically shaped bridge stop, such as where one limb of a T-shaped member is shorter than the other, thus avoiding compression of the crossing point of the circumflex artery. The asymmetric form may also be selected first based on a pre-placement angiogram.

An asymmetric posterior bridge stop may be utilized for other reasons as well. The asymmetric posterior bridge stop may be selected where a patient is found to have a severely stenotic distal great cardiac vein, where the asymmetric bridge stop better serves to avoid obstruction of that vessel. In addition, an asymmetric bridge stop may be chosen for its use in selecting application of forces differentially and preferentially on different points along the posterior mitral annulus to optimize treatment, i.e., in cases of malformed or asymmetrical mitral valves.

The anterior bridge stop region 16 is sized and configured to allow the bridging element 12 to be placed, upon passing into the right atrium through the septum, adjacent tissue in or near the right atrium. For example, as is shown in FIGS. 10A to 10D, the anterior bridge stop region 16 may be adjacent or abutting a region of fibrous tissue in the interatrial septum. As shown, the bridge stop site 16 is desirably superior to the anterior mitral annulus at about the same elevation or higher than the elevation of the posterior bridge stop region 14. In the illustrated embodiment, the anterior bridge stop region 16 is adjacent to or near the inferior rim of the fossa ovalis. Alternatively, the anterior bridge stop region 16 can be located at a more superior position in the septum, e.g., at or near the superior rim of the fossa ovalis. The anterior bridge stop region 16 can also be located in a more superior or inferior position in the septum, away from the fossa ovalis, provided that the bridge stop site does not harm the tissue region.

Figure 11A:
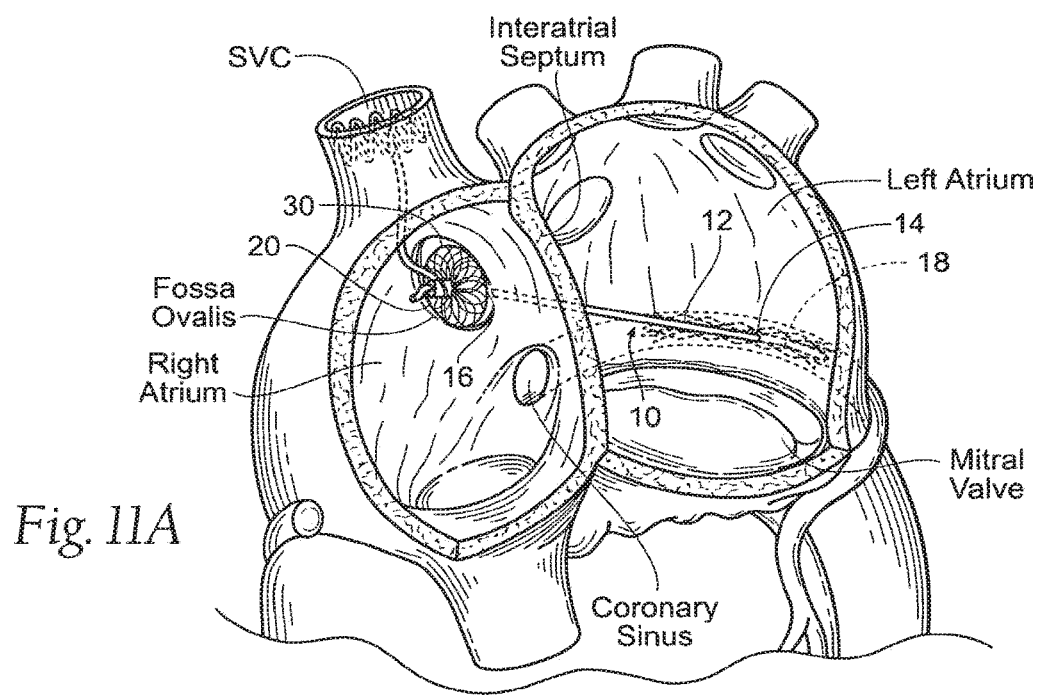
FIG. 11A is an anatomic anterior perspective view of the left and right atriums, with portions broken away and in section to show the presence of an implant system of the type shown in FIGS. 10A and 10B, with the anterior region of the implant extending through a pass-through structure, such as a septal member, in the inter-atrial septum and situated in the superior vena cava.
Figure 11B:
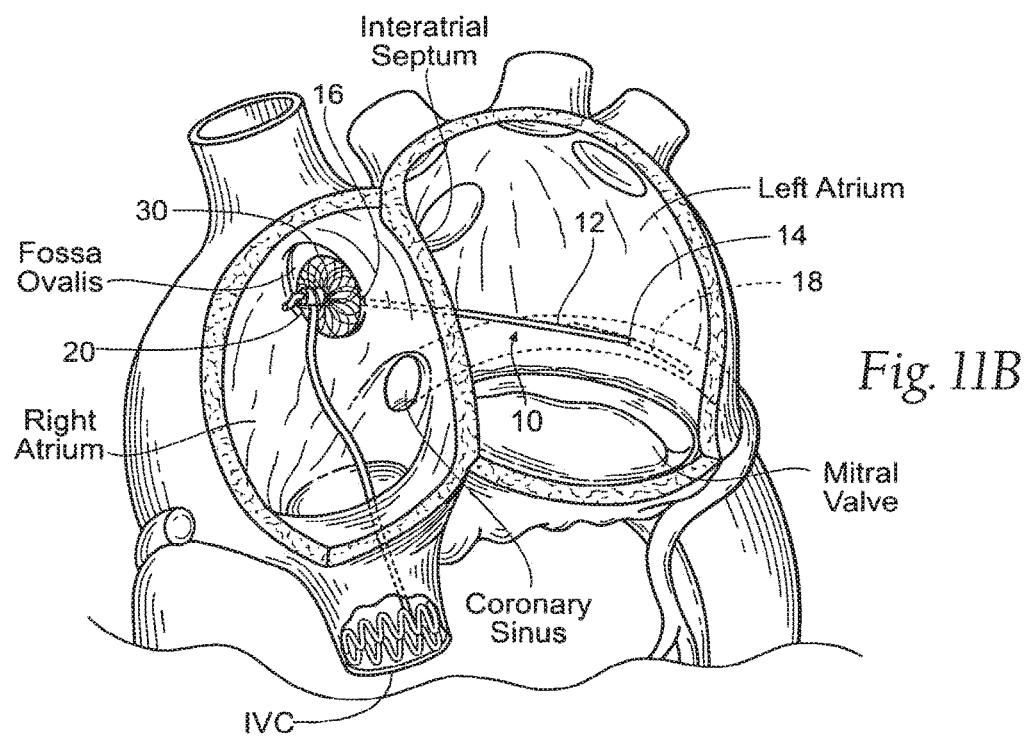
FIG. 11B is an anatomic anterior perspective view of the left and right atriums, with portions broken away and in section to show the presence of an implant system of the type shown in FIGS. 10A and 10B, with the anterior region of the implant extending through a pass-through structure, such as a septal member, in the inter-atrial septum and situated in the inferior vena cava.

Alternatively, as can be seen in FIGS. 11A and 11B, the anterior bridge stop region 16, upon passing through the septum into the right atrium, may be positioned within or otherwise situated in the superior vena cava (SVC) or the inferior vena cava (IVC), instead of at the septum itself.

Figure 7:
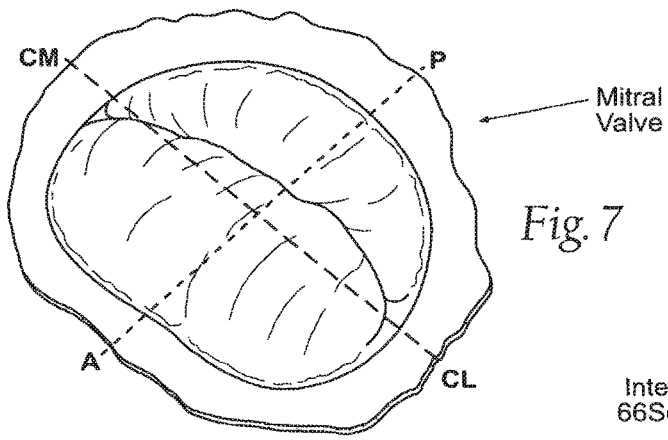
FIG. 7 is a superior view of a healthy mitral valve, with the leaflets closed and coapting at peak contraction pressures during ventricular systole.
Figure 8:
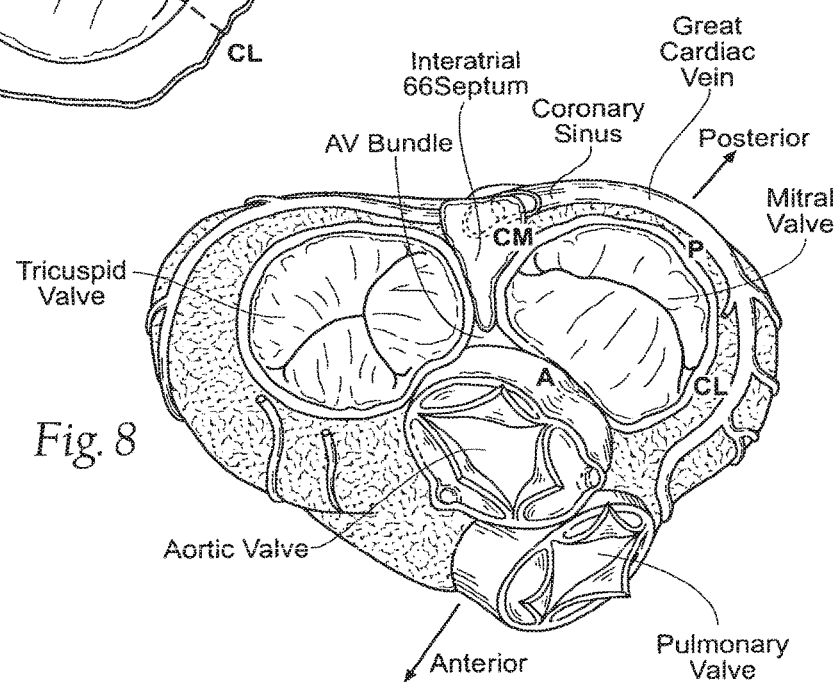
FIG. 8 is an anatomic superior view of a section of the human heart, with the normal mitral valve shown in FIG. 7 closed during ventricular systole (ventricular emptying) of the cardiac cycle.
Figure 9:
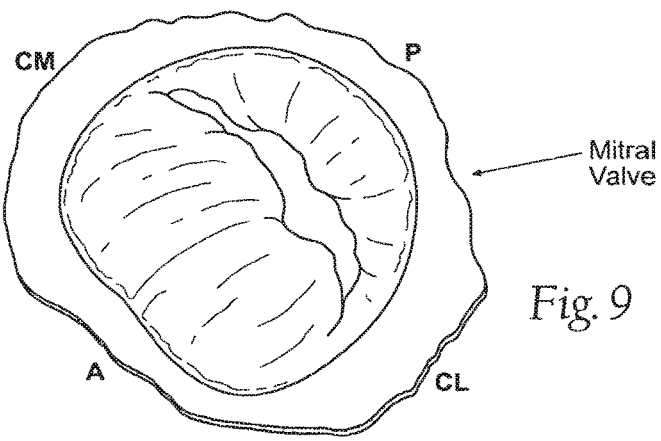
FIG. 9 is a superior view of a dysfunctional mitral valve, with the leaflets failing to coapt during peak contraction pressures during ventricular systole, leading to mitral regurgitation.

In use, the spanning region or bridging element 12 can be placed into tension between the two bridge stop regions 14 and 16. The implant 10 thereby serves to apply a direct mechanical force generally in a posterior to anterior direction across the left atrium. The direct mechanical force can serve to shorten the minor axis (line P-A in FIG. 7) of the annulus. In doing so, the implant 10 can also reactively reshape the annulus along its major axis (line CM-CL in FIG. 7) and/or reactively reshape other surrounding anatomic structures. It should be appreciated, however, the presence of the implant 10 can serve to stabilize tissue adjacent the heart valve annulus, without affecting the length of the minor or major axes.

It should also be appreciated that, when situated in other valve structures, the axes affected may not be the "major" and "minor" axes, due to the surrounding anatomy. In addition, in order to be therapeutic, the implant 10 may only need to reshape the annulus during a portion of the heart cycle, such as during late diastole and early systole when the heart is most full of blood at the onset of ventricular systolic contraction, when most of the mitral valve leakage occurs. For example, the implant 10 may be sized to restrict outward displacement of the annulus during late ventricular diastolic relaxation as the annulus dilates.

The mechanical force applied by the implant 10 across the left atrium can restore to the heart valve annulus and leaflets a more normal anatomic shape and tension. The more normal anatomic shape and tension are conducive to coaptation of the leaflets during late ventricular diastole and early ventricular systole, which, in turn, reduces mitral regurgitation.

In its most basic form, the implant 10 is made from a biocompatible metallic or polymer material, or a metallic or polymer material that is suitably coated, impregnated, or otherwise treated with a material to impart biocompatibility, or a combination of such materials. The material is also desirably radio-opaque or incorporates radio-opaque features to facilitate fluoroscopic visualization.

The implant 10 can be formed by bending, shaping, joining, machining, molding, or extrusion of a metallic or polymer wire form structure, which can have flexible or rigid, or inelastic or elastic mechanical properties, or combinations thereof. Alternatively, the implant 10 can be formed from metallic or polymer thread-like or suture material. Materials from which the implant 10 can be formed include, but are not limited to, stainless steel, Nitinol, titanium, silicone, plated metals, Elgilcy™, NP55, and NP57.

The implant 10 can take various shapes and have various cross-sectional geometries. The implant 10 can have, e.g., a generally curvilinear (i.e., round or oval) cross-section, or a generally rectilinear cross section (i.e., Square or rectangular), or combinations thereof. Shapes that promote laminar flow and therefore reduce hemolysis are contemplated, with features such as smoother surfaces and longer and narrower leading and trailing edges in the direction of blood flow.

B. The Posterior Bridge Stop Region

The posterior bridge stop region 14 is sized and configured to be located within or at the left atrium at a supra-annular position, i.e., positioned within or near the left atrium wall above the posterior mitral annulus.

In the illustrated embodiment, the posterior bridge stop region 14 is shown to be located generally at the level of the great cardiac vein, which travels adjacent to and parallel to the majority of the posterior mitral valve annulus. This tributary of the coronary sinus can provide a strong and reliable fluoroscopic landmark when a radio-opaque device is placed within it or contrast dye is injected into it. As previously described, securing the bridging element 12 at this supra-annular location also lessens the risk of encroachment of and risk of injury to the circumflex coronary artery compared to procedures applied to the mitral annulus directly. Furthermore, the supra-annular position assures no contact with the valve leaflets therefore allowing for coaptation and reduces the risk of mechanical damage.

The great cardiac vein also provides a site where relatively thin, non-fibrous atrial tissue can be readily augmented and consolidated. To enhance hold or purchase of the posterior bridge stop region 14 in what is essentially non-fibrous heart tissue, and to improve distribution of the forces applied by the implant 10, the posterior bridge stop region 14 may include a posterior bridge stop 18 placed within the great cardiac vein and abutting venous tissue. This makes possible the securing of the posterior bridge stop region 14 in a non-fibrous portion of the heart in a manner that can nevertheless sustain appreciable hold or purchase on that tissue for a substantial period of time, without dehiscence, expressed in a clinically relevant timeframe.

C. The Anterior Bridge Stop Region

The anterior bridge stop region 16 is sized and configured to allow the bridging element 12 to remain firmly in position adjacent or near the fibrous tissue and the surrounding tissues in the right atrium side of the atrial septum. The fibrous tissue in this region provides superior mechanical strength and integrity compared with muscle and can better resist a device pulling through. The septum is the most fibrous tissue structure in its own extent in the heart. Surgically handled, it is usually one of the only heart tissues into which sutures actually can be placed and can be expected to hold without pledgets or deep grasps into muscle tissue, where the latter are required.

As FIGS. 10A to 10D show, the anterior bridge stop region 16 passes through the septal wall at a supra-annular location above the plane of the anterior mitral valve annulus. The supra-annular distance on the anterior side can be generally at or above the supra-annular distance on the posterior side. As before pointed out, the anterior bridge stop region 16 is shown in FIG. 10A to 10D at or near the inferior rim of the fossa ovalis, although other more inferior or more superior sites can be used within or outside the fossa ovalis, taking into account the need to prevent harm to the septal tissue and surrounding structures.

By locating the bridging element 12 at this supra-annular level within the right atrium, which is fully outside the left atrium and spaced well above the anterior mitral annulus, the implant 10 avoids the impracticalities of endovascular attachment at or adjacent to the anterior mitral annulus, where there is just a very thin rim of annulus tissue that is bounded anteriorly by the anterior leaflet, inferiorly by the aortic outflow tract, and medially by the atrioventricular node of the conduction system. The anterior mitral annulus is where the non-coronary leaflet of the aortic valve attaches to the mitral annulus through the central fibrous body. Anterior location of the implant 10 in the supra-annular level within the right atrium (either in the septum or in a vena cava) avoids encroachment of and risk of injury to both the aortic valve and the AV node.

Figure 10A:
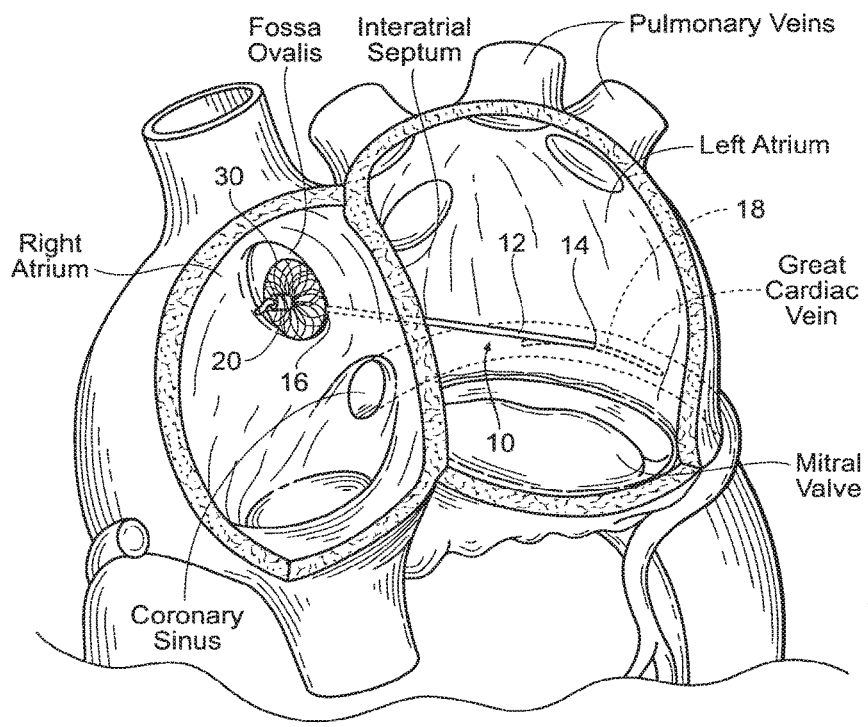
FIGS. 10A and 10B are anatomic anterior perspective views of the left and right atriums, with portions broken away and in section to show the presence of an implant system that includes an inter-atrial bridging element that spans the mitral valve annulus, with a posterior bridge stop positioned in the great cardiac vein and an anterior bridge stop, including a septal member, positioned on the inter-atrial septum, the inter-atrial bridging element extending in an essentially straight path generally from a mid-region of the annulus to the inter-atrial septum.
Figure 10B:
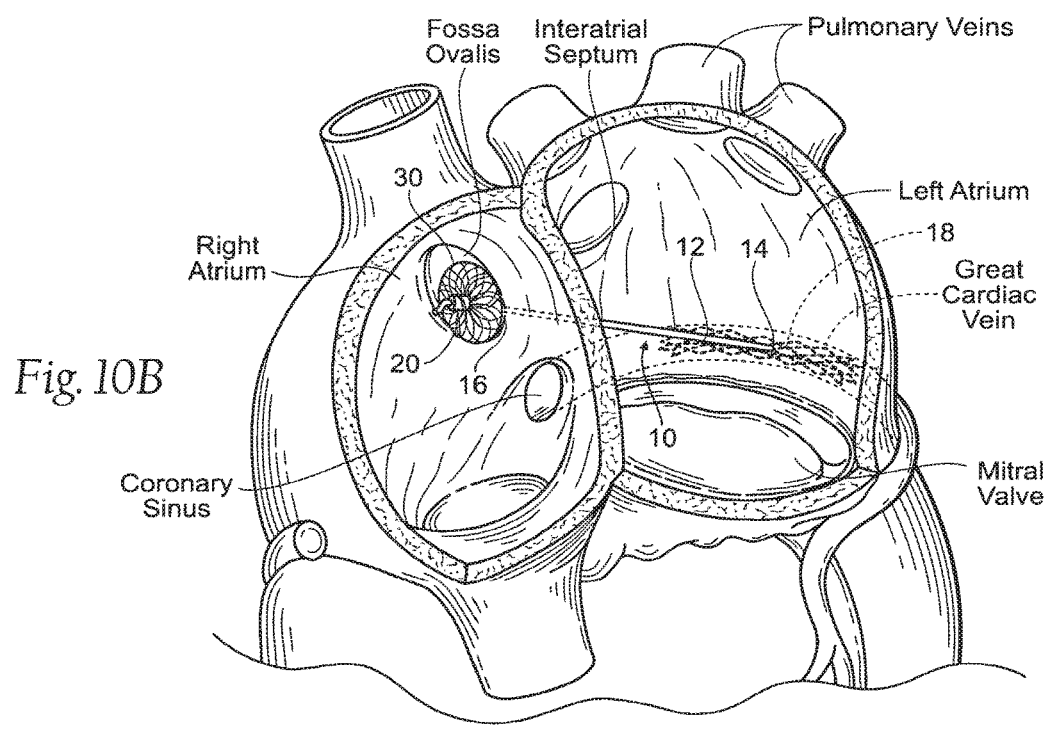
Figure 10C:
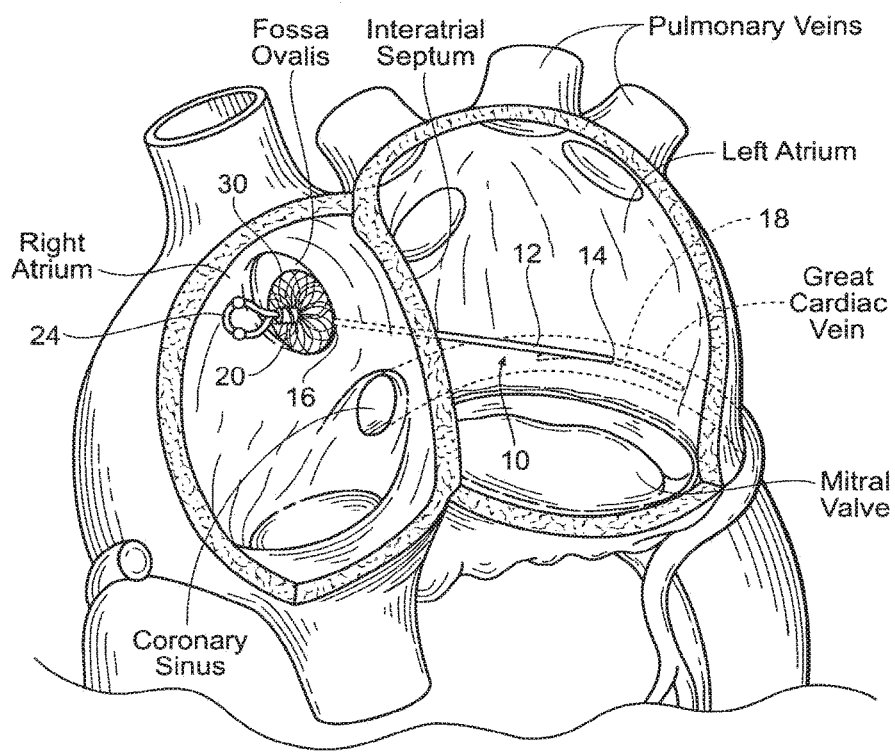
FIG. 10C is an anatomic anterior perspective view of an alternative embodiment of the implant system shown in FIGS. 10A and 10B, showing a relocation loop positioned at the anterior side of the implant for removal or adjustment of the implant system days, months, or years after the initial procedure or adjustment.
Figure 10D:
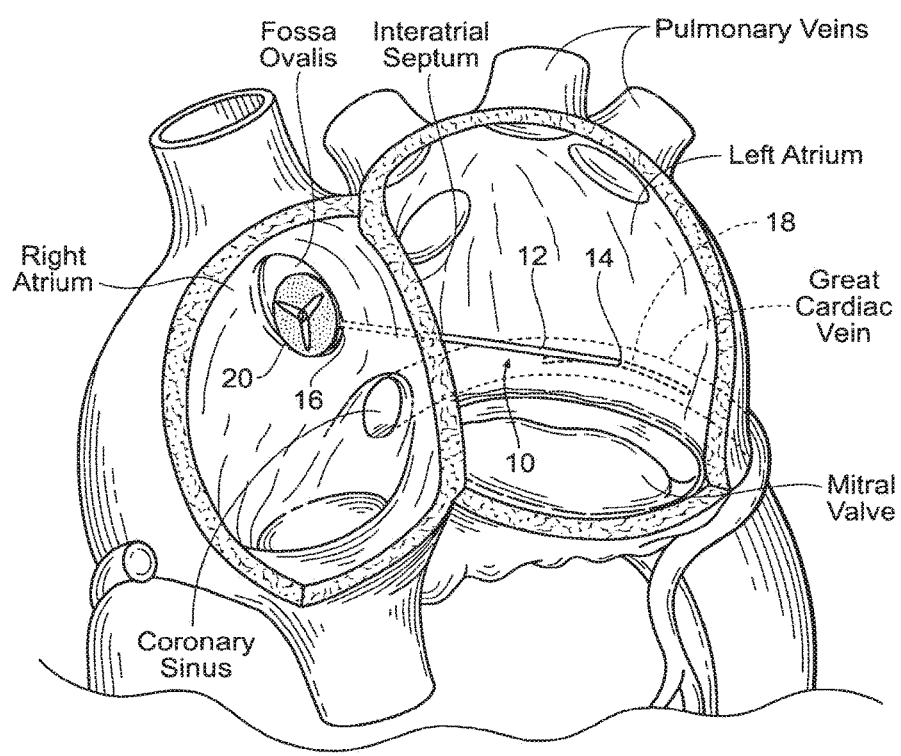
FIG. 10D is an anatomic anterior perspective view of an alternative embodiment of the implant system shown in FIGS. 10A and 10B, showing an anterior bridge stop without the addition of a septal member.
Figure 12A:
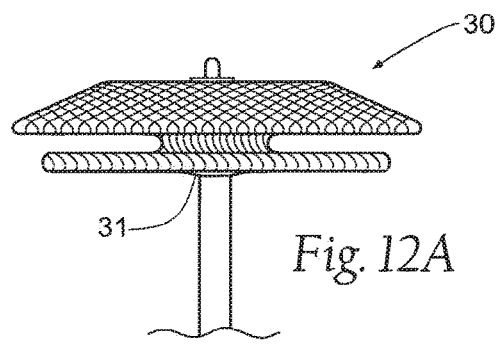
FIG. 12A is a side view of a septal member which may be used as part of the implant system of the type shown in FIGS. 10A and 10B.
Figure 12B:
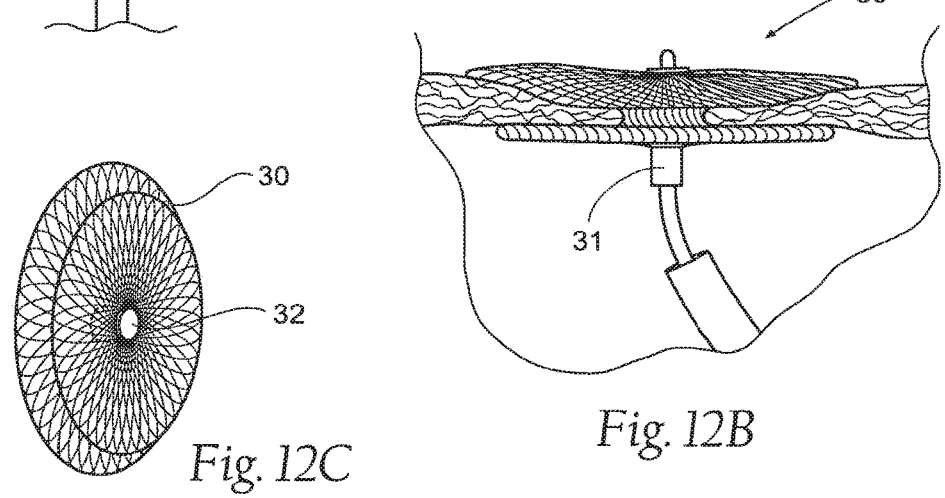
FIG. 12B is a side view of a deployed septal member of the type shown in FIG. 21A, showing the member sandwiching portions of the septum through an existing hole.

The purchase of the anterior bridge stop region 16 in fibrous septal tissue is desirably enhanced by a septal member 30 or an anterior bridge stop 20, or a combination of both. FIGS. 10A through 10C show the anterior bridge stop region including a septal member 30. FIG. 10D shows the anterior bridge stop region without a septal member. The septal member 30 may be an expandable device and also may be a commercially available device such as a septal occluder, e.g., Amplatzer® PFO Occluder (see FIGS. 12A and 12B). The septal member 30 preferably mechanically amplifies the hold or purchase of the anterior bridge stop region 16 in the fibrous tissue site. The septal member 30 also desirably increases reliance, at least partly, on neighboring anatomic structures of the septum to make firm the position of the implant 10. In addition, the septal member 30 may also serve to plug or occlude the small aperture that was created in the fossa ovalis or surrounding area during the implantation procedure.

Figure 12C:
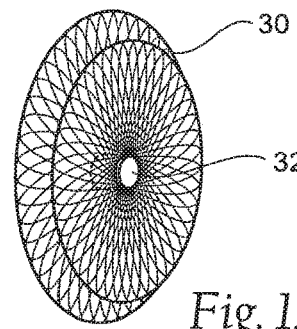
FIG. 12C is a perspective view of an alternative embodiment of the septal member shown in FIG. 12A, showing a grommet or similar protective device positioned at or near the center of the septal member.

Anticipating that pinpoint pulling forces will be applied by the anterior bridge stop region 16 to the septum, the forces acting on the septal member 30 should be spread over a moderate area, without causing impingement on valve, vessels or conduction tissues. With the pulling or tensioning forces being transmitted down to the annulus, shortening of the minor axis is achieved. A flexurally stiff septal member is preferred because it will tend to cause less focal narrowing in the direction of bridge element tension of the left atrium as tension on the bridging element is increased. The septal member 30 should also have a low profile configuration and highly washable surfaces to diminish thrombus formation for devices deployed inside the heart. The septal member may also have a collapsed configuration and a deployed configuration. The septal member 30 may also include a hub 31 (see FIGS. 12A and 12B) to allow attachment of the bridge stop 20. The septal member 30 may also include a grommet or similar protective device 32 positioned at or near the center of the septal member to allow unobstructed movement of the bridging element 12 through the septal member, such as during adjustment of the bridging element 12 (see FIG. 12C). The hub 31 may provide this feature as well.

Figure 11C:
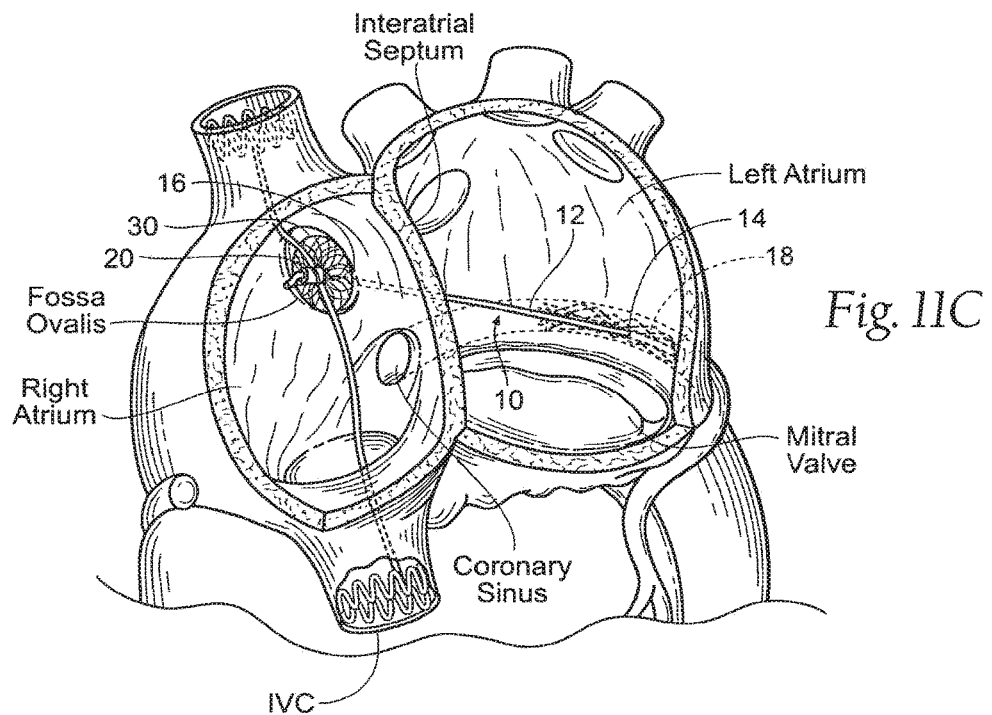
FIG. 11C is an anatomic anterior perspective view of the left and right atriums, with portions broken away and in section to show the presence of an implant system of the type shown in FIGS. 10A to 10C, with the anterior region of the implant situated on the inter-atrial septum, as well as in the superior vena cava and the inferior vena cava.

A septal brace may also be used in combination with the septal member 30 and anterior bridge stop 20 to distribute forces uniformly along the septum (see FIG. 11C). Alternatively, devices in the IVC or the SVC can be used as bridge stop sites (see FIGS. 11A and 11B), instead of confined to the septum.

Location of the posterior and anterior bridge stop regions 14 and 16 having radio-opaque bridge locks and well demarcated fluoroscopic landmarks respectively at the supra-annular tissue sites just described, not only provides freedom from key vital structure damage or local impingement—e.g., to the circumflex artery, AV node, and the left coronary and non-coronary cusps of the aortic valve— but the supra-annular focused sites are also not reliant on purchase between tissue and direct tension-loaded penetrating/biting/holding tissue attachment mechanisms. Instead, physical structures and force distribution mechanisms such as stents, T-shaped members, and septal members can be used, which better accommodate the attachment or abutment of mechanical levers and bridge locks, and through which potential tissue tearing forces can be better distributed. Further, the bridge stop sites 14, 16 do not require the operator to use complex imaging.

Adjustment of implant position after or during implantation is also facilitated, free of these constraints. The bridge stop sites 14, 16 also make possible full intra-atrial retrieval of the implant 10 by endovascularly snaring and then cutting the bridging element 12 at either side of the left atrial wall, from which it emerges. As seen in FIG. 10C, relocation means, such as a hook or loop 24, may be provided to aid in redocking to the bridge stop sites 14, 16 to allow for future adjustment or for implant removal, for example. The relocation means allows for adjustment or removal of the implant days, months, or even years after the initial procedure or after an adjustment.

D. Orientation of the Bridging Element

In the embodiments shown in FIGS. 10A to 10D, the implant 10 is shown to span the left atrium beginning at a posterior point of focus superior to the approximate mid-point of the mitral valve annulus, and proceeding in an anterior direction in a generally straight path directly to the region of anterior focus in the septum. As shown in FIGS. 10A to 10D, the spanning region or bridging element 12 of the implant 10 may be preformed or otherwise configured to extend in this essentially straight path above the plane of the valve, without significant deviation in elevation toward or away from the plane of the annulus, other than as dictated by any difference in elevation between the posterior and anterior regions of placement.

Lateral or medial deviations and/or superior or inferior deviations in this path can be imparted, if desired, to affect the nature and direction of the force vector or vectors that the implant 10 applies. It should be appreciated that the spanning region or bridging element 12 can be preformed or otherwise configured with various medial/lateral and/or inferior/superior deviations to achieve targeted annulus and/or atrial structure remodeling, which takes into account the particular therapeutic needs and morphology of the patient. In addition, deviations in the path of the bridging element may also be imparted in order to avoid the high velocity blood path within a heart chamber, such as the left atrium.

Figure 13:
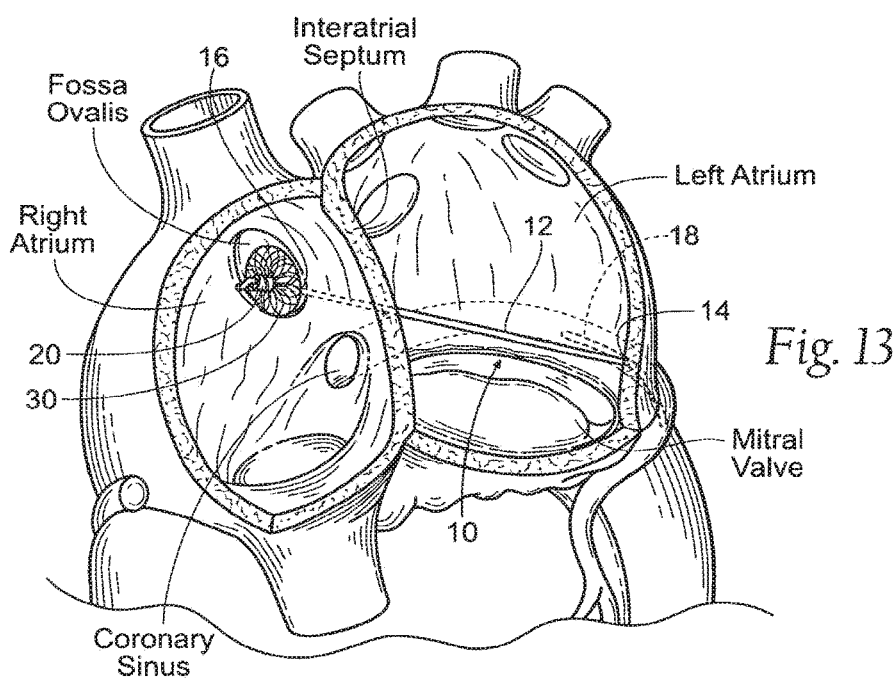
FIG. 13 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in an essentially straight path generally from a lateral region of the annulus.

For example, as shown in FIG. 13, the implant 10 is shown to span the left atrium beginning at a posterior region that is closer to a lateral trigone of the annulus (i.e., farther from the septum). Alternatively, the posterior region can be at a position that is closer to a medial trigone of the annulus (i.e., closer to the septum). From either one of these posterior regions, the implant 10 can extend in an anterior direction in a straight path directly to the anterior region in the septum. As shown in FIG. 13, like FIG. 10A, the spanning region or bridging element 12 of the implant 10 is preformed or otherwise configured to extend in an essentially straight path above the plane of the valve, without significant deviation in elevation toward or away from the plane of the annulus, other than as dictated by the difference in elevation, if any, between the posterior and anterior regions.

Figure 14:
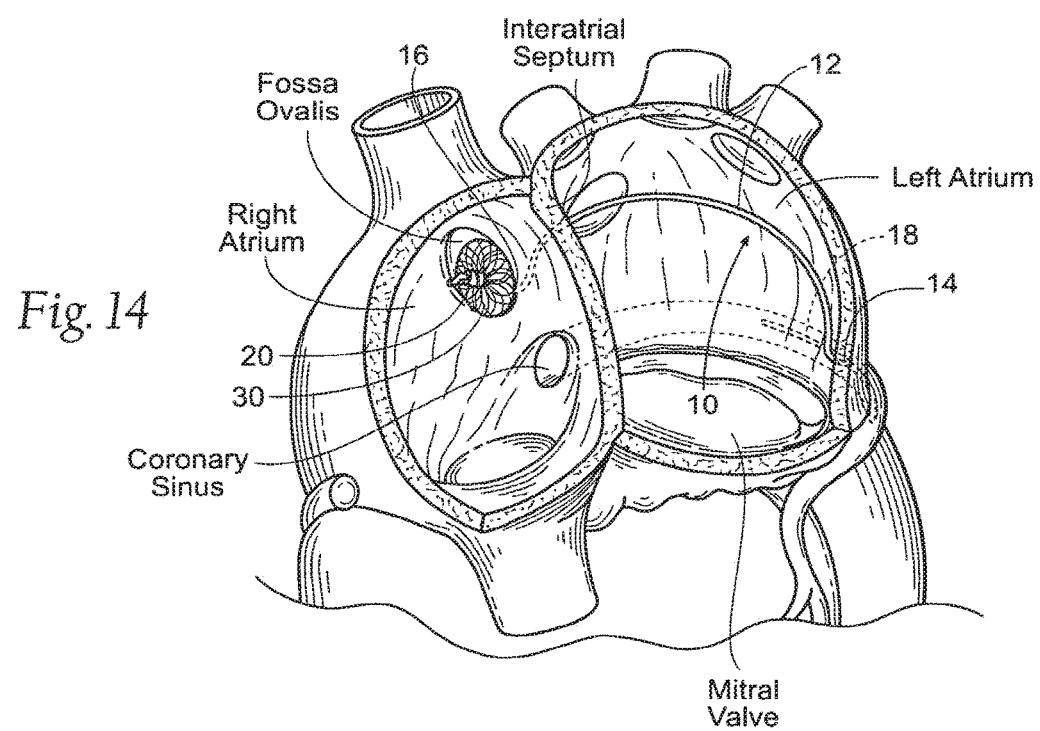
FIG. 14 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in an upwardly curved or domed path generally from a lateral region of the annulus.

Regardless of the particular location of the posterior region. (see FIG. 14), the spanning region or bridging element 12 of the implant 10 can be preformed or otherwise configured to arch upward above the plane of the valve toward the dome of the left atrium Alternatively (see FIG. 15), the spanning region or bridging element 12 of the implant 10 can be preformed or otherwise configured to dip downward toward the plane of the valve toward the annulus, extending close to the plane of the valve, but otherwise avoiding interference with the valve leaflets. Or, still alternatively (see FIG. 16), the spanning region or bridging element 12 of the implant 10 can be preformed or otherwise configured to follow a curvilinear path, bending towards a trigone (medial or lateral) of the annulus before passage to the anterior region.

Figure 17:
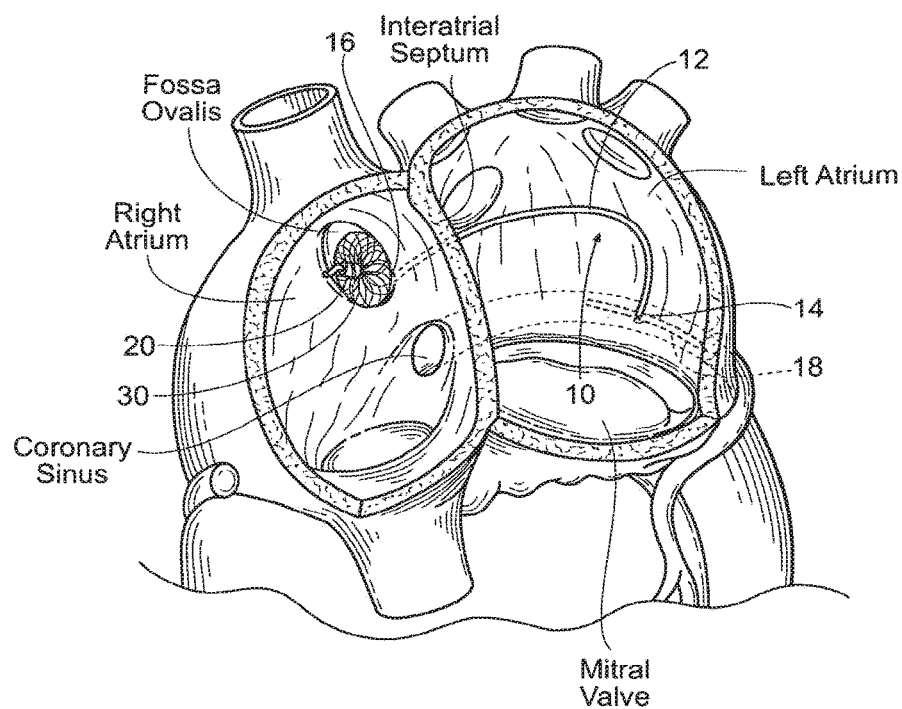
FIG. 17 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a curvilinear path, bending around a trigone of the annulus generally from a mid-region region of the annulus, as well as elevating in an arch toward the dome of the left atrium.
Figure 18:
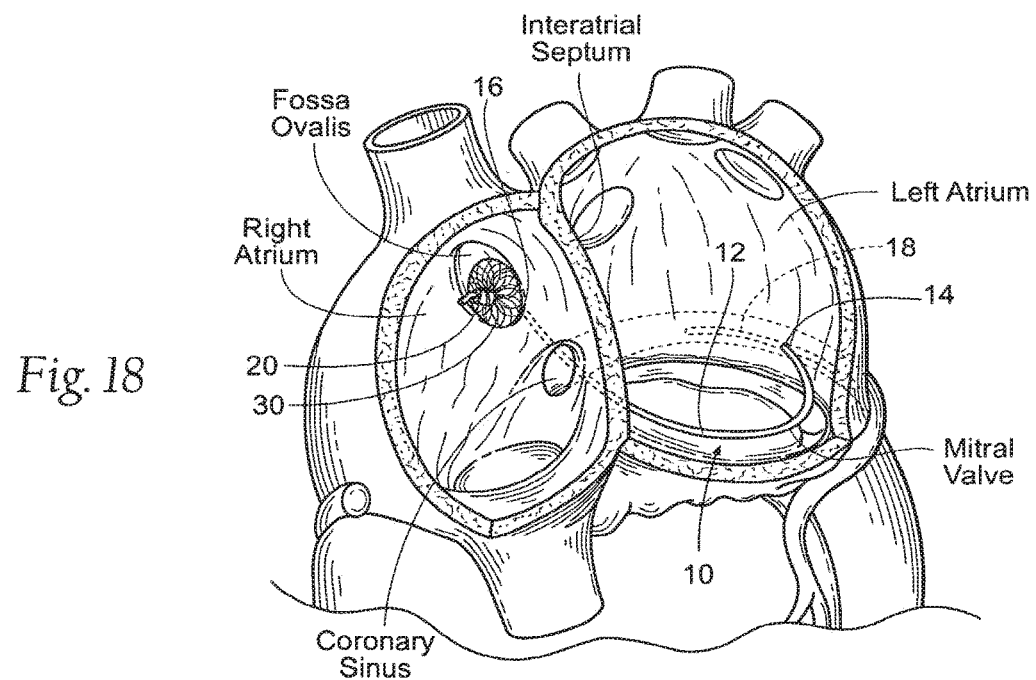
FIG. 18 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a curvilinear path, bending around a trigone of the annulus generally from a mid-region region of the annulus, as well as dipping downward toward the plane of the valve.

Various combinations of lateral/medial deviations and superior/inferior deviations of the spanning region or bridging element 12 of the implant 10 are of course possible. For example, as shown in FIG. 17, the spanning region or bridging element 12 can follow a curvilinear path bending around a trigone (medial or lateral) of the annulus as well as elevate in an arch away from the plane of the valve. Or, as shown in FIG. 18, the spanning region or bridging element 12 can follow a curvilinear path bending around a trigone (medial or lateral) of the annulus as well as dip toward the plane of the valve.

Figure 19:
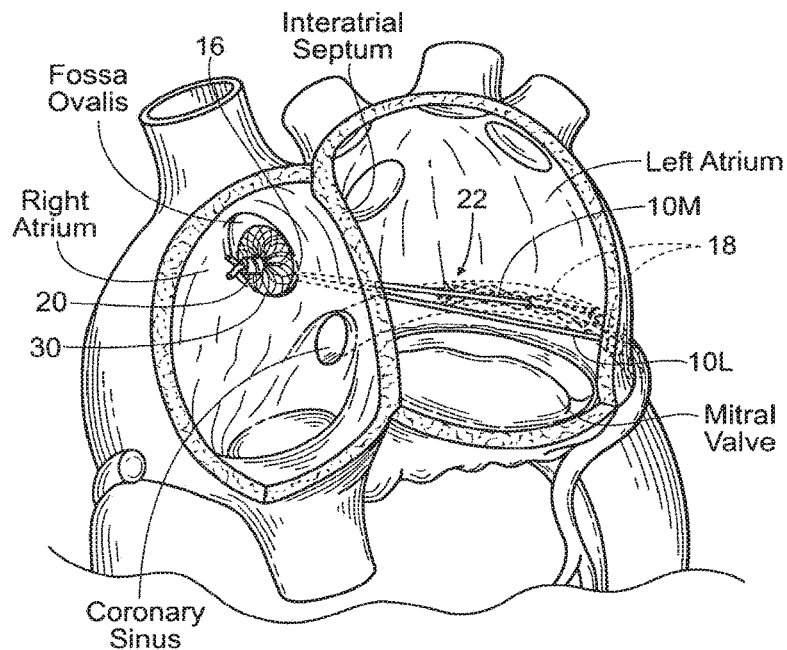
FIG. 19 is an anatomic anterior perspective view of the left and right atriums, with portions broken away and in section to show the presence of an implant system that includes two inter-atrial bridging elements that span the mitral valve annulus, each with a posterior bridge stop in the great cardiac vein and an anterior bridge stop on the inter-atrial septum, the inter-atrial bridging elements both extending in generally straight paths from different regions of the annulus.

Regardless of the orientation, more than one implant 10 can be installed to form an implant system 22. For example, FIG. 19 shows a system 22 comprising a lateral implant 10L and a medial implant 10M of a type consistent with the implant 10 as described. FIG. 19 shows the implants 10L and 10M being located at a common anterior bridge stop region 16. It should be appreciated that the implants 10L and 10M can also include spaced apart anterior bridge stop regions.

Figure 15:
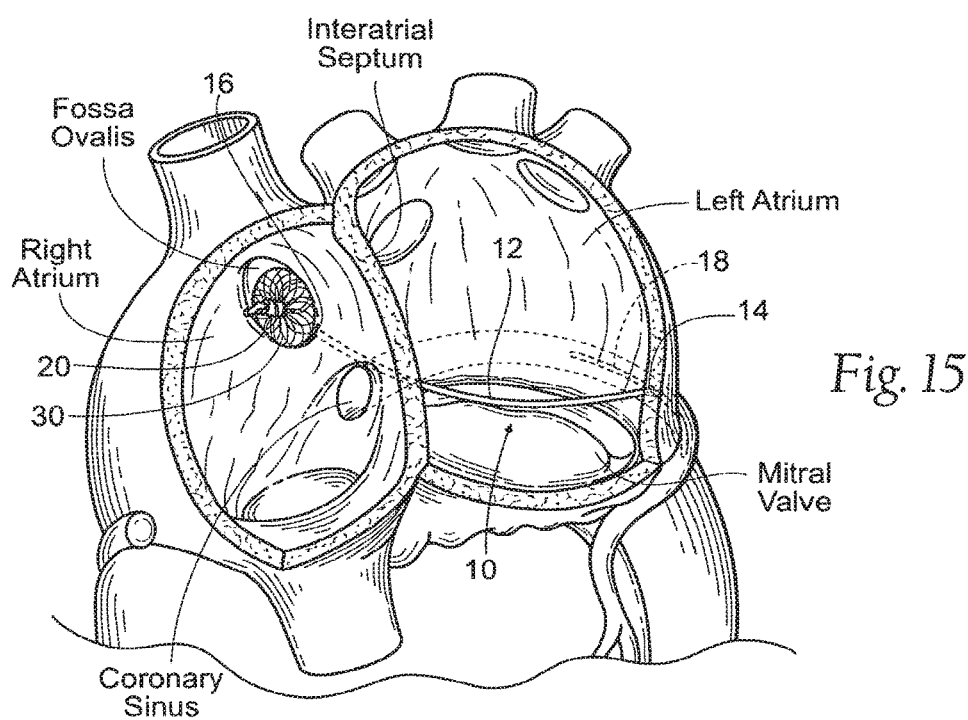
FIG. 15 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a downwardly curved path generally from a lateral region of the annulus.

One or both of the implants 10L and 10M can be straight (as in FIG. 13), or arch upward (as in FIG. 14), or bend downward (as in FIG. 15). A given system 10 can comprise lateral and medial implants 10L and 10M of different configurations. Also, a given system 22 can comprise more than two implants 10.

Figure 16:
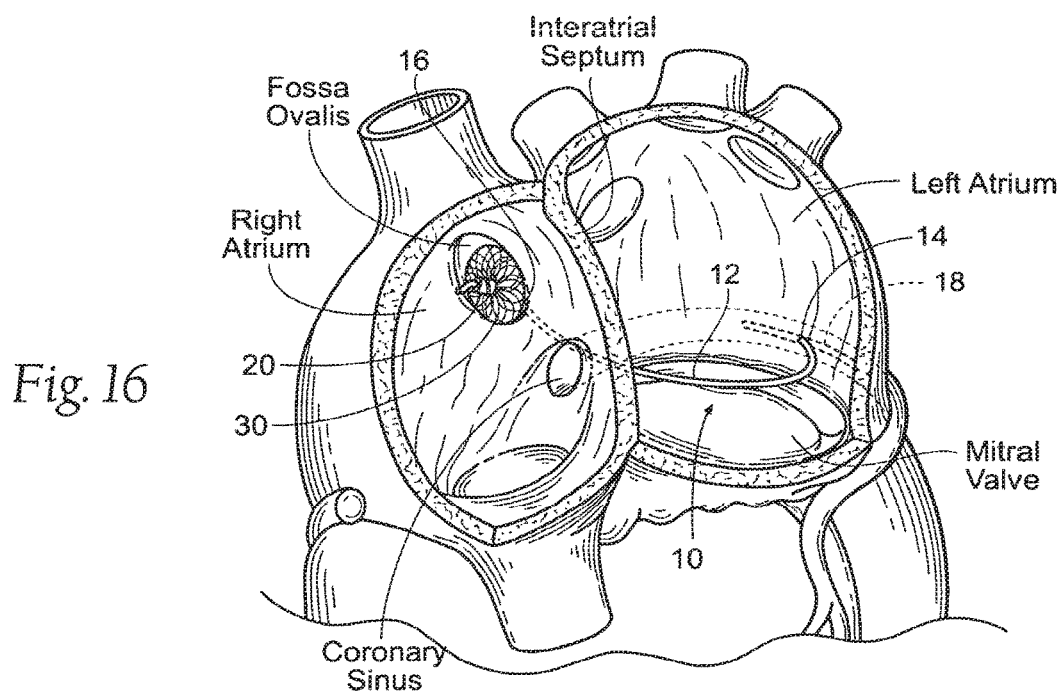
FIG. 16 is an anatomic anterior perspective view of the left and right atriums, with portions broken away and in section to show the presence of an implant system that includes an inter-atrial bridging element that spans the mitral valve annulus, with a posterior region situated in the great cardiac vein and an anterior region situated on the interatrial septum, the inter-atrial bridging element extending in a curvilinear path, bending around a trigone of the annulus generally from a mid-region region of the annulus.
Figure 20:
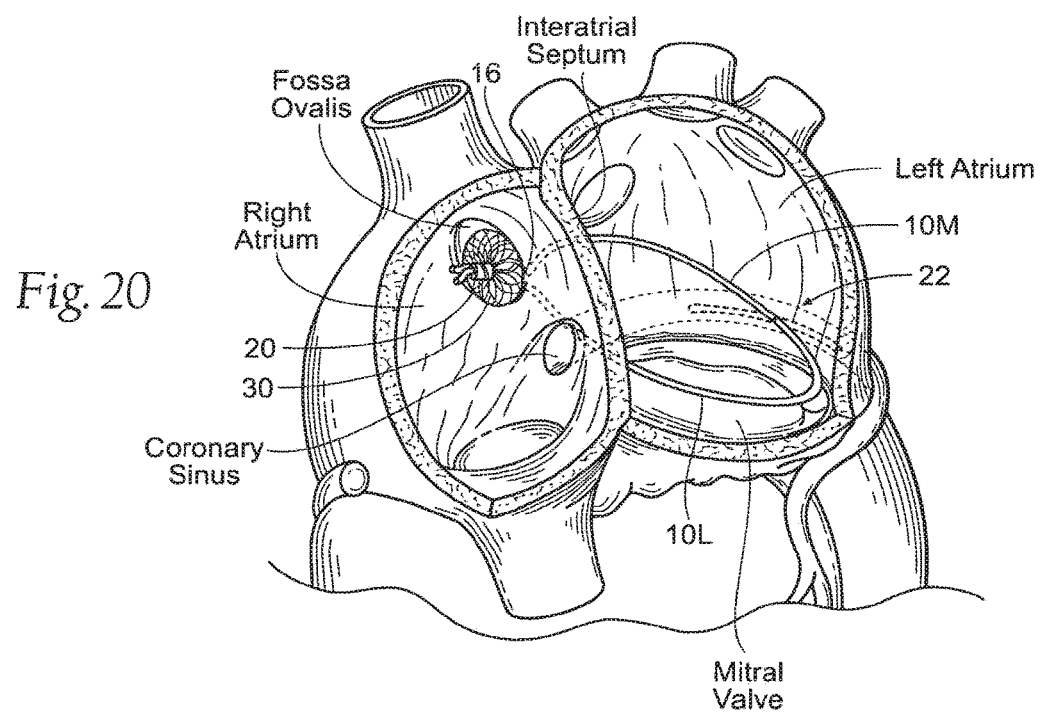
FIG. 20 is an anatomic anterior perspective view of the left and right atriums, with portions broken away and in section to show the presence of an implant system that includes two inter-atrial bridging elements that span the mitral valve annulus, each with a posterior region situated in the great cardiac vein and an anterior region situated on the interatrial septum, the inter-atrial bridging elements both extending in generally curvilinear paths from adjacent regions of the annulus.

FIG. 20 shows a system 22 comprising two curvilinear implants 10L and 10M of the type shown in FIG. 16. In FIG. 20, the curvilinear implants 10L and 10M are shown to be situated at a common posterior region, but the implants 10 can proceed from spaced apart posterior regions, as well. One or both of the curvilinear implants 10L and 10M can be parallel with respect to the plane of the valve (as in FIG. 16), or arch upward (as in FIG. 17), or bend downward (as in FIG. 18). A given system 22 can comprise curvilinear implants 10L and 10M of different configurations.

Figure 21:
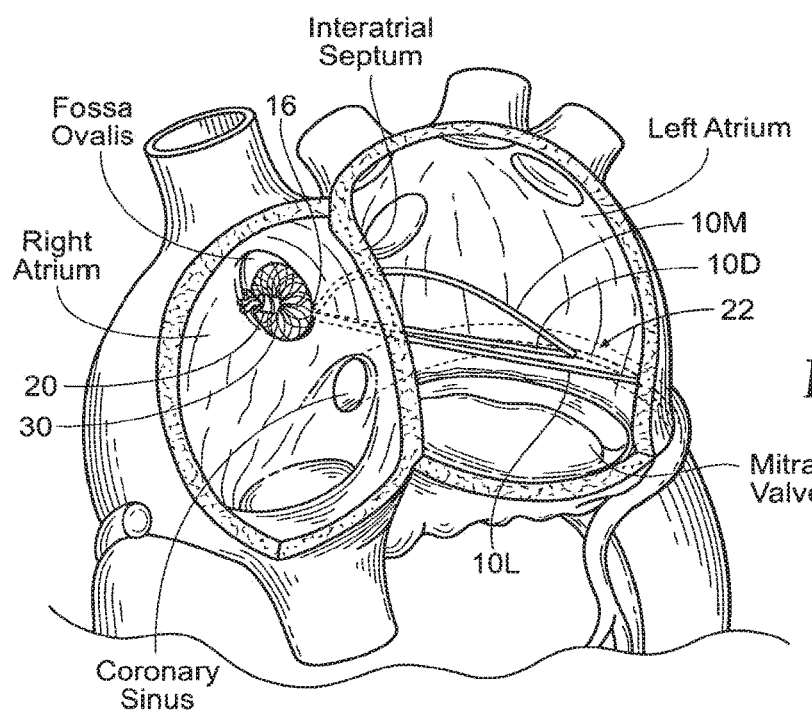
FIG. 21 is an anatomic anterior perspective view of the left and right atriums, with portions broken away and in section to show the presence of an implant system that includes three inter-atrial bridging elements that span the mitral valve annulus, each with a posterior region situated in the great cardiac vein and an anterior region situated on the interatrial septum, two of the inter-atrial bridging elements extending in generally straight paths from different regions of the annulus, and the third inter-atrial bridging elements extending in a generally curvilinear path toward a trigone of the annulus.

FIG. 21 shows a system 22 comprising a direct middle implant 10D, a medial curvilinear implant 10M, and a direct lateral implant 10L. One, two, or all of the implants 10 can be parallel to the valve, or arch upward, or bend downward, as previously described.

E. Posterior and Anterior Bridge Stop

Figure 22A:
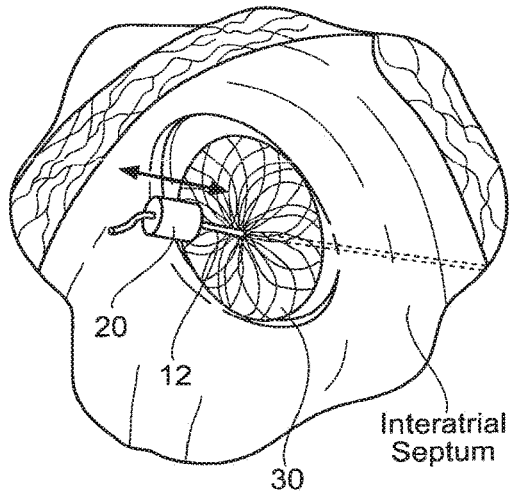
FIGS. 22A and 22B are sectional views showing the ability of a bridge stop used in conjunction with the implant shown in FIGS. 10A to 10C to move back and forth independent of the septal wall and inner wall of the great cardiac vein.
Figure 22B:
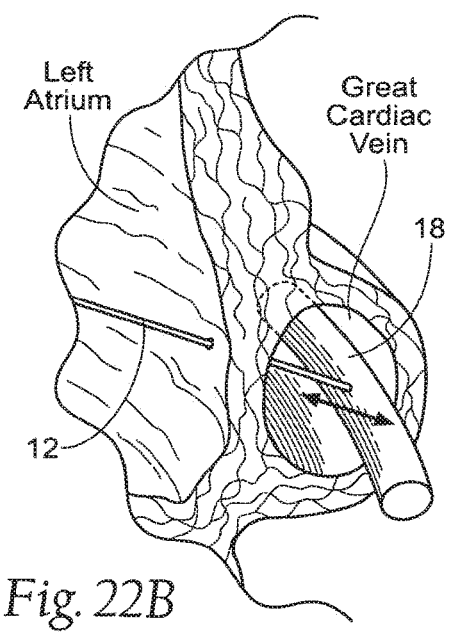

It is to be appreciated that a bridge stop as described herein, including a posterior or anterior bridge stop, describes an apparatus that may releasably hold the bridging element 12 in a tensioned state. As can be seen in FIGS. 22A and 22B, bridge stops 20 and 18 respectively are shown releasably secured to the bridging element 12, allowing the bridge stop structure to move back and forth independent of the inter-atrial septum and inner wall of the great cardiac vein during a portion of the cardiac cycle when the tension force may be reduced or becomes zero. Alternative embodiments are also described, all of which may provide this function. It is also to be appreciated that the general descriptions of posterior and anterior are non-limiting to the bridge stop function, i.e., a posterior bridge stop may be used anterior, and an anterior bridge stop may be used posterior.

When the bridge stop is in an abutting relationship to a septal member or a T-shaped member, for example, the bridge stop allows the bridging element to move freely within or around the septal member or T-shaped member, i.e., the bridging element is not connected to the septal member or T-shaped member. In this configuration, the bridging element is held in tension by the bridge stop, whereby the septal member or T-shaped member serves to distribute the force applied by the bridging element across a larger surface area. Alternatively, the bridge stop may be mechanically connected to the septal member or T-shaped member, e.g., when the bridge stop is positioned over and secured to the septal member hub. In this configuration, the bridging element is fixed relative to the septal member position and is not free to move about the septal member.

II. General Methods of Trans-Septal Implantation

The implants 10 or implant systems 22 as just described lend themselves to implantation in a heart valve annulus in various ways. The implants 10 or implant systems 22 can be implanted, e.g., in an open heart surgical procedure. Alternatively, the implant 10 or implant systems 22 can be implanted using catheter-based technology via a peripheral venous access site, such as in the femoral jugular vein (via the IVC or SVC) under image guidance, or trans-arterial retrograde approaches to the left atrium through the aorta from the femoral artery also under image guidance.

Alternatively, the implants 10 or implant systems 22 can be implanted using thoracoscopic means through the chest, or by means of other surgical access through the right atrium, also under image guidance. Image guidance includes but is not limited to fluoroscopy, ultrasound, magnetic resonance, computed tomography, or combinations thereof.

The implants 10 or implant systems 22 may comprise independent components that are assembled within the body to form an implant, or alternatively, independent components that are assembled exterior the body and implanted as a whole.

FIGS. 23 to 30 show a representative embodiment of the deployment of an implant 10 of the type shown in FIGS. 10A to 10D by a percutaneous, catheter-based procedure, under image guidance.

Figure 23:
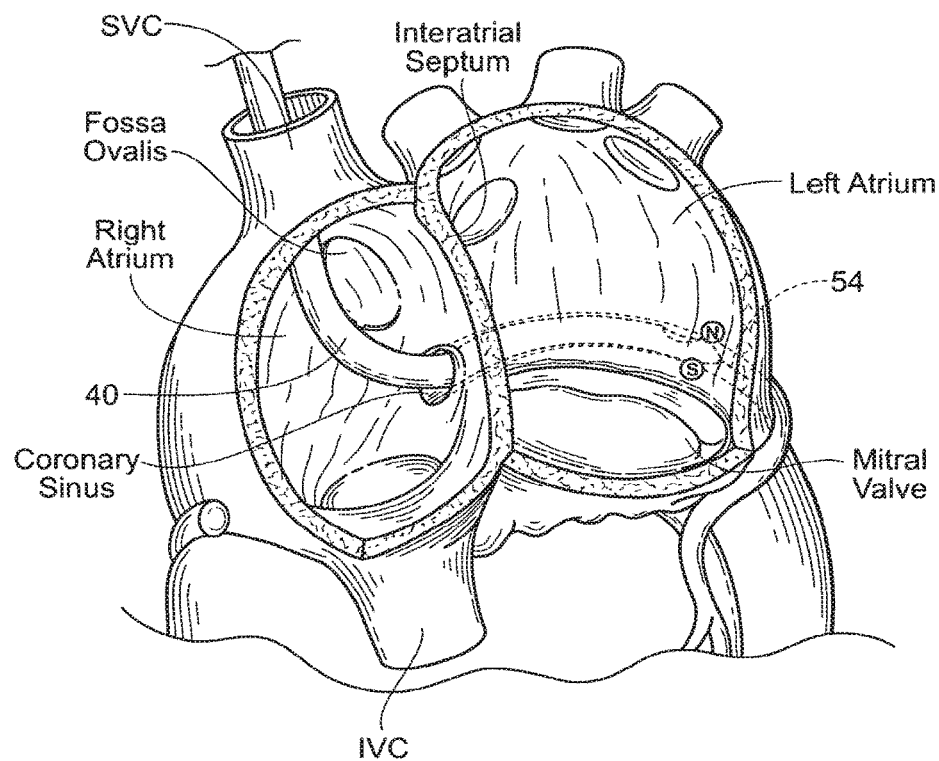
FIGS. 23 to 30 are anatomic views depicting representative catheter-based devices and steps for implanting an implant system of the type shown in FIGS. 10A to 10C.
Figure 24:
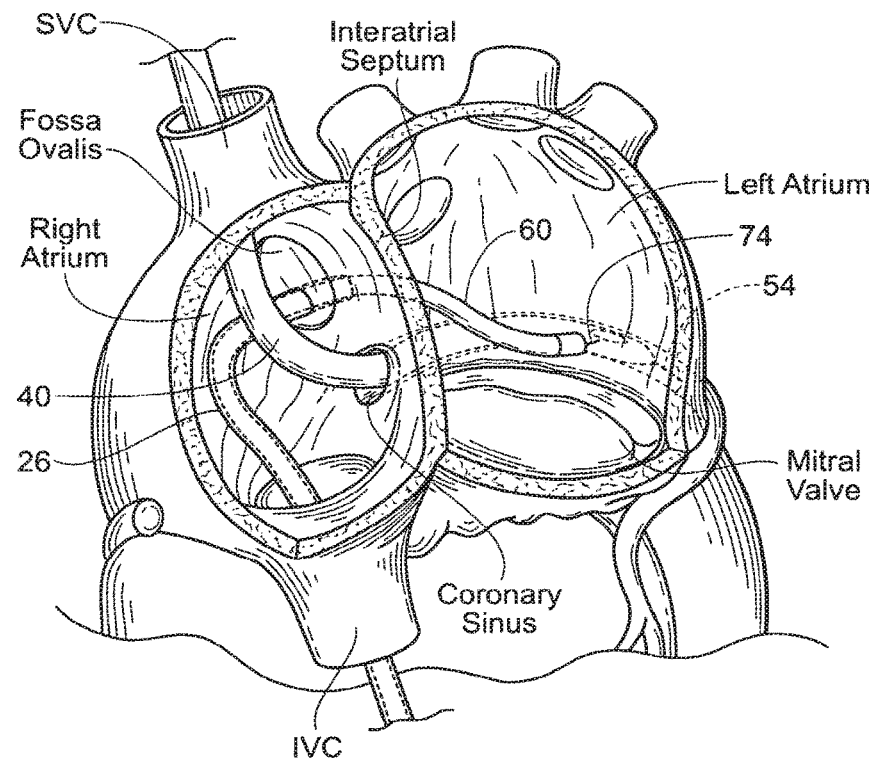

Percutaneous vascular access is achieved by conventional methods into the femoral or jugular vein, or a combination of both. As FIGS. 23 and 24 show, under image guidance, a first catheter, or great cardiac vein catheter 40, and a second catheter, or left atrium catheter 60, are steered through the vasculature into the right atrium. It is a function of the great cardiac vein (GCV) catheter 40 and left atrium (LA) catheter 60 to establish the posterior bridge end stop region. Catheter access to the right and left atriums can be achieved through either a femoral vein to IVC or SVC route (in the latter case, for a naval brace) or an upper extremity or neck vein to SVC or IVC route (in the latter case, for a caval brace). In the case of the SVC, the easiest access is from the upper extremity or neck venous system; however, the IVC can also be accessed by passing through the SVC and right atrium. Similarly the easiest access to the IVC is through the femoral vein; however the SVC can also be accessed by passing through the IVC and right atrium. FIGS. 23, 24, 27, 28 and 29 show access through both a SVC route and an IVC route for purposes of illustration.

The implantation of the implant 10 or implant systems 22 are first described here in four general steps. Each of these steps, and the various tools used, is then described with additional detail below in section III. Additionally, alternative implantation steps may be used and are described in section IV. Additional alternative embodiments of a bridge stop are described in section V, additional alternative embodiments of a T-shaped member or bridge stop are described in section VI, and additional alternative embodiments of a bridging element are described in section VII.

A first implantation step can be generally described as establishing the posterior bridge stop region 14. As can be seen in FIG. 24, the GCV catheter 40 is steered through the vasculature into the right atrium. The GCV catheter 40 is then steered through the coronary sinus and into the great cardiac vein. The second catheter, or LA catheter 60, is also steered through the vasculature and into the right atrium. The LA catheter 60 then passes through the septal wall at or near the fossa ovalis and enters the left atrium. A Mullins™ catheter 26 may be provided to assist the guidance of the LA catheter 60 into the left atrium. Once the GCV catheter 40 and the LA catheter 60 are in their respective positions in the great cardiac vein and left atrium, it is a function of the GCV and LA catheters 40, 60 to configure the posterior bridge stop region 14.

A second step can be generally described as establishing the trans-septal bridging element 12. A deployment catheter 24 via the LA catheter 60 is used to position a posterior bridge stop 18 and a preferably preattached and predetermined length of bridging element 12 within the great cardiac vein (see FIG. 27). The predetermined length of bridging element 12, e.g., two meters, extends from the posterior bridge stop 18, through the left atrium, through the fossa ovalis, through the vasculature, and preferably remains accessible exterior the body. The predetermined length of bridging element may be cut or detached in a future step, leaving implanted the portion extending from the posterior bridge stop 18 to the anterior bridge stop 20. Alternatively, the bridging element 20 may not be cut or detached at the anterior bridge stop 20, but instead the bridging element 20 may be allowed to extend into the IVC for possible future retrieval.

Figure 29:
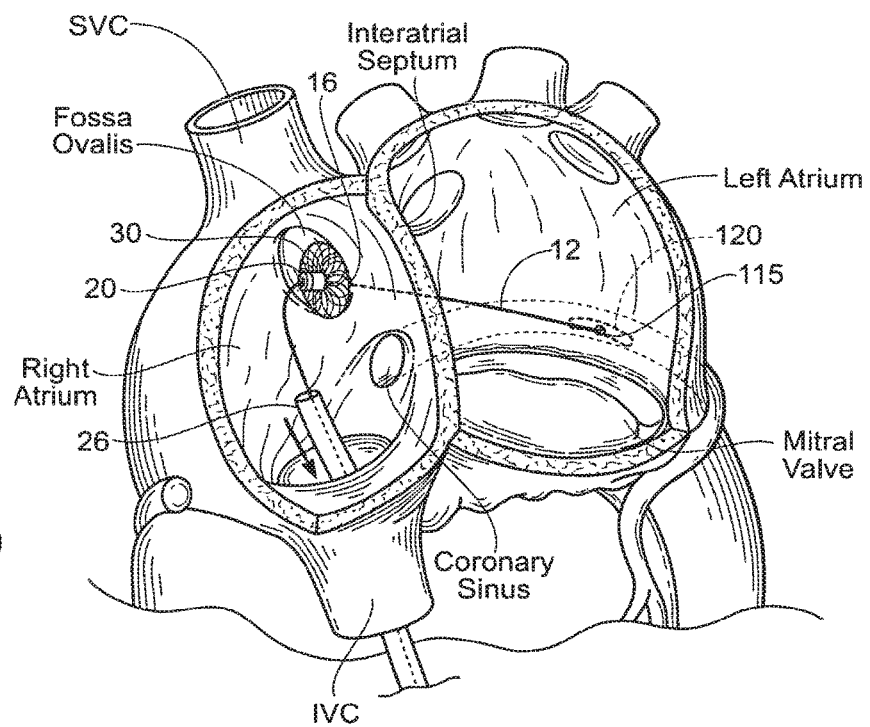

A third step can be generally described as establishing the anterior bridge stop region 16 (see. FIG. 29). The bridging element 12 is first threaded through the septal member 30. The septal member 30 is then advanced over the bridging element 12 in a collapsed condition through Mullins catheter 26, and is positioned and deployed at or near the fossa ovalis within the right atrium. A bridge stop 20 may be attached to the bridging element 12 and advanced with the septal member 30, or alternatively, the bridge stop 20 may be advanced to the right atrium side of the septal member 30 after the septal member has been positioned or deployed.

A fourth step can be generally described as adjusting the bridging element 12 for proper therapeutic effects. With the posterior bridge stop region 14, bridging element 12, and anterior bridge stop region 16 configured as previously described, a tension is placed on the bridging element 12. The implant 10 and associated regions may be allowed to settle for a predetermined amount of time, e.g., five or more seconds. The mitral valve and mitral valve regurgitation are observed for desired therapeutic effects. The tension on the bridging element 12 may be adjusted or readjusted until a desired result is achieved. The bridge stop 20 is then allowed to secure the bridging element 12 when the desired tension or measured length or degree of mitral regurgitation reduction is achieved.

III. Detailed Methods and Implantation Apparatus

The four generally described steps of implantation will now be described in greater detail, including the various tools and apparatus used in the implantation of the implant 10 or implant systems 22. An exemplary embodiment will describe the methods and tools for implanting an implant 10. These same or similar methods and tools may be used to implant an implant system 22 as well.

A. Establish Posterior Bridge Stop Region

1. Implantation Tools

Various tools may be used to establish the posterior bridge stop region 14. For emple, the great cardiac vein (GCV) catheter 40, the left atrium (LA) catheter 60, and a cutting catheter 80 may be used.

FIG. 37A shows one embodiment of the GCV catheter 40 in accordance with the present invention. The GCV catheter 40 preferably includes a magnetic or ferromagnetic head 42 positioned on the distal end of the catheter shaft 45, and a hub 46 positioned on the proximal end. The catheter shaft 45 may include a first section 48 and a second section 50. The first section 48 may be generally stiff to allow for torquability of the shaft 45, and may be of a solid or braided construction. The first section 48 includes a predetermined length, e.g., fifty centimeters, to allow positioning of the shaft 45 within the vasculature structure. The second section 50 may be generally flexible to allow for steerability within the vasculature, i.e., into the coronary sinus. The second section 50 may also include a predetermined length, e.g., ten centimeters. The inner diameter or lumen 52 of the catheter shaft 45 is preferably sized to allow passage of a GCV guide wire 54, and additionally an LA guide wire 74 (see FIGS. 39 and 40). Both the GCV guide wire 54 and the LA guide wire 74 may be pre-bent, and both may be steerable. The GCV catheter 40 preferably includes a radio-opaque marker 56 to facilitate adjusting the catheter under image guidance to align with the LA catheter 60.

Figure 25:
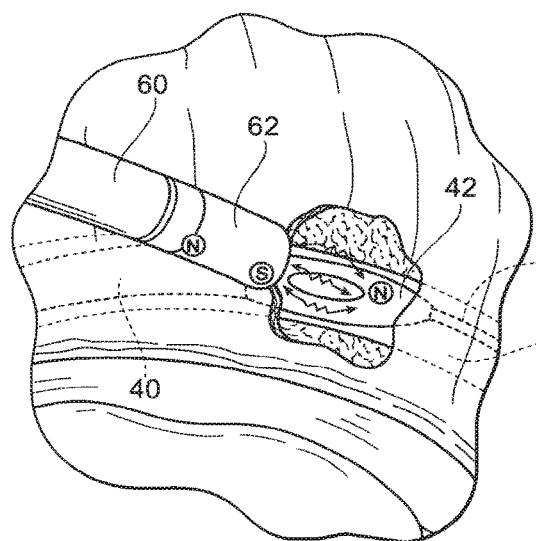

The magnetic or ferromagnetic head 42 is preferably polarized to magnetically attract or couple the distal end of the LA catheter 60 (see FIGS. 37B and 25). The head 42 includes a side hole 58 formed therein to allow for passage of the LA guide wire 74. As shown in FIG. 40, the left atrial side 43 of the head 42 has an attracting magnetic force, and the exterior of the heart side 44 of the head 42 has a repelling magnetic force. It should be appreciated that these magnetic forces may be reversed, as long as the magnetic forces in each catheter coincide with proper magnetic attraction. The magnetic head 42 preferably includes a bullet or coned shaped tip 55 to allow the catheter to track into the vasculature system. Within the tip 55 is an end hole 59, configured to allow for passage of the GCV guide wire 54.

FIG. 38 shows one embodiment of the LA catheter 60. Similar to the GCV catheter 40, the LA catheter 60 preferably includes a magnetic or ferromagnetic head 62 positioned on the distal end of the catheter shaft 65 and a hub 66 positioned on the proximal end. The catheter shaft 65 may include a first section 68 and a second section 70. The first section 68 may be generally stiff to allow for torquability of the shaft 65, and may be of a solid or braided construction. The first section 68 includes a predetermined length, e.g., ninety centimeters, to allow positioning of the shaft 65 within the vasculature structure. The second section 70 may be generally flexible and anatomically shaped to allow for steerability through the fossa ovalis and into the left atrium. The second section 70 may also include a predetermined length, e.g., ten centimeters. The inner diameter or lumen 72 of the catheter shaft 65 is preferably sized to allow passage of an LA guide wire 74, and additionally may accept the guide wire 54 passed from the GCV. The LA catheter 60 may include a radio-opaque marker 76 to facilitate adjusting the catheter 60 under image guidance to align with the GCV catheter 40.

The magnetic or ferromagnetic head 62 of the LA catheter 60 is polarized to magnetically attract or couple the distal end of the GCV catheter 40. As shown in FIG. 40, end side 64 of the head 62 is polarized to attract the GCV catheter head 42. The magnetic forces in the head 62 may be reversed, as long as attracting magnetic poles in the LA catheter 60 and the GCV catheter 40 are aligned. The magnetic head 62 preferably includes a generally planar tip 75, and also includes a center bore 78 sized for passage of the cutting catheter 80 and the LA guide wire 74 (see FIG. 38).

FIG. 41 shows the cutting catheter 80 preferably sized to be positioned within the inner diameter or lumen 72 of the LA catheter 60. Alternatively, the cutting catheter 80 may be positioned over the LA guide wire 74 with the LA catheter 60 removed.

The cutting catheter 80 preferably includes a hollow cutting tip 82 positioned on the distal end of the catheter shaft 85, and a hub 86 positioned on the proximal end. The catheter shaft 85 may include a first section 88 and a second section 90. The first section 88 may be generally stiff to allow for torquability of the shaft 85, and may be of a solid or braided construction. The first section 88 includes a predetermined length, e.g., ninety centimeters, to allow positioning of the shaft 85 within the vasculature structure and the LA catheter. The second section 90 may be generally flexible to allow for steerability through the fossa ovalis and into the left atrium. The second section 90 may also include a predetermined length, e.g., twenty centimeters. The inner diameter 92 of the catheter shaft 85 is preferably sized to allow passage of the LA guide wire 74. The cutting catheter 80 preferably includes a radio-opaque marker 96 positioned on the shaft 85 so as to mark the depth of cut against the radio-opaque magnet head 62 or marker 76 of the LA catheter 60.

The hollow cutting or penetrating tip 82 includes a sharpened distal end 98 and is preferably sized to fit through the LA catheter 60 and magnetic head 62 (see FIG. 42A). Alternatively, as seen in FIGS. 42B and 42C, cutting or penetrating tips 100 and 105 may be used in place of, or in combination with, the hollow cutting tip 82. The tri-blade 100 of FIG. 42B includes a sharp distal tip 101 and three cutting blades 102, although any number of blades may be used. The tri-blade 100 may be used to avoid producing cored tissue, which may be a product of the hollow cutting tip 82. The elimination of cored tissue helps to reduce the possibility of an embolic complication. The sharp tipped guide wire 105 shown in FIG. 42C may also be used. The sharp tip 106 is positioned on the end of a guide wire to pierce the wall of the left atrium and great cardiac vein.

2. Implantation Methods

Access to the vascular system is commonly provided through the use of introducers known in the art. A 16 F or less hemostasis introducer sheath (not shown), for example, may be first positioned in the superior vena cava (SVC), providing access for the GCV catheter 40. Alternatively, the introducer may be positioned in the subclavian vein. A second 16 F or less introducer sheath (not shown) may then be positioned in the right femoral vein, providing access for the LA catheter 60. Access at both the SVC and the right femoral vein, for example, also allows the implantation methods to utilize a loop guide wire. For instance, in a procedure to be described later, a loop guide wire is generated by advancing the LA guide wire 74 through the vasculature until it exits the body and extends external the body at both the superior vena cava sheath and femoral sheath. The LA guide wire 74 may follow an intravascular path that extends at least from the superior vena cava sheath through the interatrial septum into the left atrium and from the left atrium through atrial tissue and through a great cardiac vein to the femoral sheath. The loop guide wire enables the physician to both push and pull devices into the vasculature during the implantation procedure (see FIGS. 35A and 36A).

An optional step may include the positioning of a catheter or catheters within the vascular system to provide baseline measurements. An AcuNav™ intracardiac echocardiography (ICE) catheter (not shown), or similar device, may be positioned via the right femoral artery or vein to provide measurements such as, by way of non-limiting examples, a baseline septal-lateral. (S-L) separation distance measurement, atrial wall separation, and a mitral regurgitation measurement. Additionally, the ICE catheter may be used to evaluate aortic, tricuspid, and pulmonary valves, IVC, SVC, pulmonary veins, and left atrium access.

The GCV catheter is then deployed in the great cardiac vein adjacent a posterior annulus of the mitral valve. From the SVC, under image guidance, the 0.035 inch GCV guide wire 54, for example, is advanced into the coronary sinus and to the great cardiac vein. Optionally, an injection of contrast with an angiographic catheter may be made into the left main artery from the aorta and an image taken of the left coronary sinus system to evaluate the position of vital coronary arterial structures. Additionally, an injection of contrast may be made to the great cardiac vein in order to provide an image and a measurement. If the great cardiac vein is too small, the great cardiac vein may be dilated with a 5 to 12 millimeter balloon, for example, to midway the posterior leaflet. The GCV catheter 40 is then advanced over the GCV guide wire 54 to a location in the great cardiac vein, for example near the center of the posterior leaflet or posterior mitral valve annulus (see FIG. 23). The desired position for the GCV catheter 40 may also be viewed as approximately 2 to 6 centimeters from the anterior intraventricular vein takeoff. Once the GCV catheter 40 is positioned, an injection may be made to confirm sufficient blood flow around the GCV catheter 40. If blood flow is low or non-existent, the GCV catheter 40 may be pulled back into the coronary sinus until needed.

The LA catheter 60 is then deployed in the left atrium. From the femoral vein, under image guidance, the 0.035 inch LA guide wire 74, for example, is advanced into the right atrium. A 7 F Mullins™ dilator with a trans-septal needle is deployed into the right atrium (not shown). An injection is made within the right atrium to locate the fossa ovalis on the septal wall. The septal wall at the fossa ovalis is then punctured with the trans-septal needle and the guide wire 74 is advanced into the left atrium. The trans-septal needle is then removed and the dilator is advanced into the left atrium. An injection is made to confirm position relative to the left ventricle. The 7 F Mullins system is removed and then replaced with a 12 F or other appropriately sized Mullins system 26. The 12 F Mullins system 26 is positioned within the right atrium and extends a short distance into the left atrium.

As seen in FIG. 21, the LA catheter 60 is next advanced over the LA guide wire 74 and positioned within the left atrium. If the GCV catheter 40 had been backed out to allow for blood flow, it is now advanced back into position. The GCV catheter 40 is then grossly rotated to magnetically align with the LA catheter 60. Referring now to FIG. 25, preferably under image guidance, the LA catheter 60 is advanced and rotated if necessary until the magnetically attractant head 62 of the LA catheter 60 magnetically attracts to the magnetically attractant head 42 of the GCV catheter 40. The left atrial wall and the great cardiac vein venous tissue separate the LA catheter 60 and the GCV catheter 40. The magnetic attachment is preferably confirmed via imaging from several viewing angles, if necessary.

Figure 26:
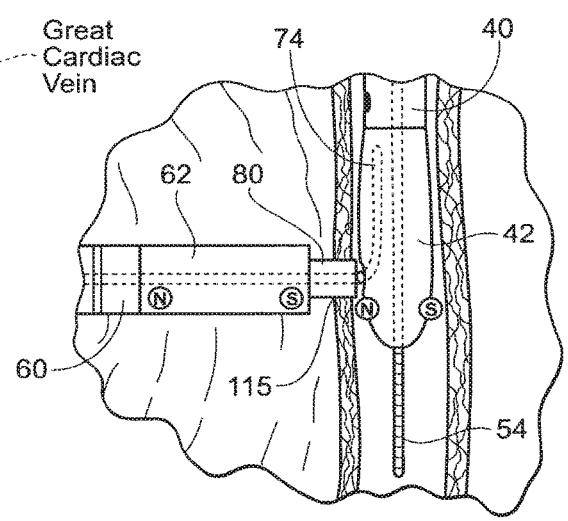

Next, an access lumen 115 is created into the great cardiac vein (see FIG. 26). The cutting catheter 80 is first placed over the LA guide wire 74 inside of the LA catheter 60. The cutting catheter 80 and the LA guide wire 74 are advanced until resistance is felt against the wall of the left atrium. The LA guide wire 74 is slightly retracted, and while a forward pressure is applied to the cutting catheter 80, the cutting catheter 80 is rotated and/or pushed. Under image guidance, penetration of the cutting catheter 80 into the great cardiac vein is confirmed. The LA guide wire 74 is then advanced into the great cardiac vein and further into the GCV catheter 40 toward the coronary sinus, eventually exiting the body at the sheath in the neck. The LA catheter 60 and the GCV catheter 40 may now be removed. Both the LA guide wire 74 and the GCV guide wire 54 are now in position for the next step of establishing the trans-septal bridging element 12.

B. Establish Trans-Septal Bridging Element

Now that the posterior bridge stop region 14 has been established, the trans-septal bridging element 12 is positioned to extend from the posterior bridge stop region 14 in a posterior to anterior direction across the left atrium and to the anterior bridge stop region 16.

In this exemplary embodiment of the methods of implantation, the trans-septal bridging element 12 is implanted via a left atrium to GCV approach. In this approach, the GCV guide wire 54 is not utilized and may be removed. Alternatively, a GCV to left atrium approach is also described. In this approach, the GCV guide wire 54 is utilized. The alternative GCV to left atrium approach for establishing the trans-septal bridging element 12 will be described in detail in section IV.

The bridging element 12 may be composed of a suture material or suture equivalent known in the art. Common examples may include, but are not limited to, 1-0, 2-0, and 3-0 polyester suture, stainless steel braid (e.g., 0.022 inch diameter), and NiTi wire (e.g., 0.008 inch diameter). Alternatively, the bridging element 12 may be composed of biological tissue such as bovine, equine or porcine pericardium, or preserved mammalian tissue, preferably in a gluteraldehyde fixed condition. Alternatively the bridging element 12 may be encased by pericardium, or polyester fabric or equivalent. Additional alternative bridging elements are described in section VII.

A bridge stop, such as a T-shaped bridge stop 120 is preferably connected to the predetermined length of the bridging element 12. The bridging element 12 may be secured to the T-shaped bridge stop 120 through the use of a bridge stop 170 (see FIG. 44A), or may be connected to the T-shaped bridge stop 120 by securing means 121, such as tying, welding, or gluing, or any combination thereof. As seen in FIGS. 43A and 43B, the T-shaped bridge stop 120 may be symmetrically shaped or asymmetrically shaped, may be curved or straight, and preferably includes a flexible tube 122 having a predetermined length, e.g., three to eight centimeters, and an inner diameter 124 sized to allow at least a guide wire to pass through. The tube 122 is preferably braided, but may be solid as well, and may also be coated with a polymer material. Each end 126 of the tube 122 preferably includes a radio-opaque marker 128 to aid in locating and positioning the T-shaped bridge stop 120. The tube 122 also preferably includes atraumatic ends 130 to protect the vessel walls. The T-shaped bridge stop 120 may be flexurally curved or preshaped so as to generally conform to the curved shape of the great cardiac vein or interatrial septum and be less traumatic to surrounding tissue. The overall shape of the T-shaped bridge stop 120 may be predetermined and based on a number of factors, including, but not limited to the length of the bridge stop, the material composition of the bridge stop, and the loading to be applied to the bridge stop.

A reinforcing center tube 132 may also be included with the T-shaped bridge stop 120. The reinforcing tube 132 may be positioned over the flexible tube 122, as shown, or, alternatively, may be positioned within the flexible tube 122. The reinforcing tube 132 is preferably solid, but may be braided as well, and may be shorter in length, e.g., one centimeter, than the flexible tube 122. The reinforcing center tube 132 adds stiffness to the T-shaped bridge stop 120 and aids in preventing egress of the T-shaped member 120 through the cored or pierced lumen 115 in the great cardiac vein and left atrium well.

Alternative T-shaped members or bridge locks and means for connecting the bridging element 12 to the T-shaped bridge locks are described in section VI.

Figure 27:
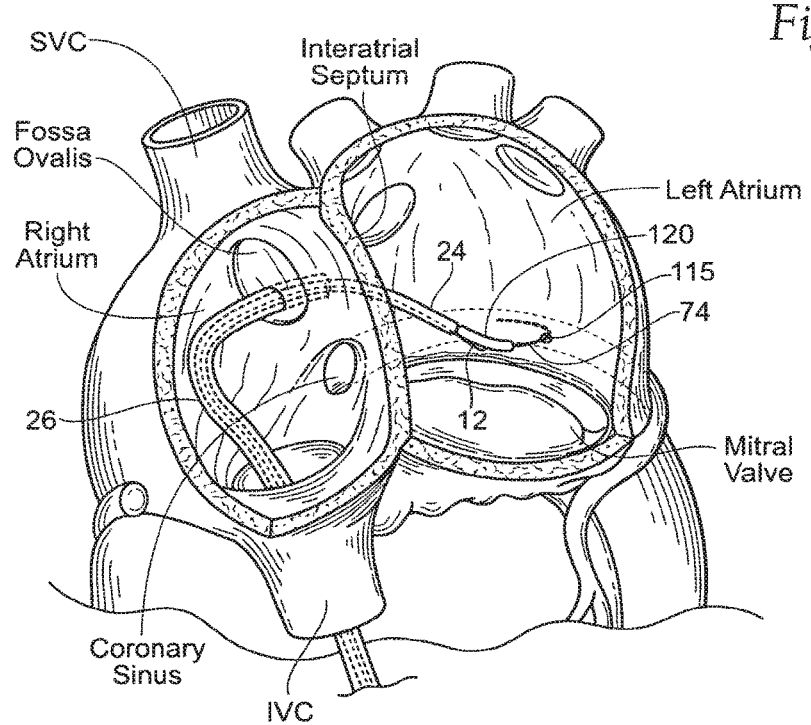

As can be seen in FIG. 27, the T-shaped bridge stop 120 (connected to the leading end of the bridging element 12) is first positioned onto or over the LA guide wire 74. The deployment catheter 24 is then positioned onto the LA guide wire 74 (which remains in position and extends into the great cardiac vein) and is used to push the T-shaped bridge stop 120 through the Mullins catheter 26 and into the right atrium, and from the right atrium through the interatrial septum into the left atrium, and from the left atrium through atrial tissue into a region of the great cardiac vein adjacent the posterior mitral valve annulus. The LA guide wire 74 is then withdrawn proximal to the tip of the deployment catheter 24. The deployment catheter 24 and the guide wire 74 are then withdrawn just to the left atrium wall. The T-shaped bridge stop 120 and the attached bridging element 12 remain within the great cardiac vein. The length of bridging element 12 extends from the posterior T-shaped bridge stop 120, through the left atrium, through the fossa ovalis, through the vasculature, and preferably the trailing end remains accessible exterior the body. Preferably under image guidance, the trailing end of the bridging element 12 is gently pulled, letting the T-shaped bridge stop 120 separate from the deployment catheter 24. Once separation is confirmed, again the bridging element 12 is gently pulled to position the T-shaped bridge stop 120 against the venous tissue within the region of the great cardiac vein and centered over the great cardiac vein access lumen 115. The deployment catheter 24 and the guide wire 74 may then be removed (see FIG. 28).

The trans-septal bridging element 12 is now in position and extends in a posterior to anterior direction from the posterior bridge stop region 14, across the left atrium, and to the anterior bridge stop region 16. The bridging element 12 preferably extends through the vasculature structure and extends exterior the body.

C. Establish Anterior Bridge Stop Region

Now that the trans-septal bridging element 12 is in position, the anterior bridge stop region 16 is next to be established.

In one embodiment, the proximal portion or trailing end of the bridging element 12 extending exterior the body is then threaded through or around an anterior bridge stop, such as the septal member 30. Preferably, the bridging element 12 is passed through the septal member 30 outside of the body nearest its center so that, when later deployed over the fossa ovalis, the bridging element 12 transmits its force to a central point on the septal member 30, thereby reducing twisting or rocking of the septal member. The septal member is advanced over the bridging element 12 in a collapsed configuration through the Mullins catheter 26, and is positioned within the right atrium and deployed at the fossa ovalis and in abutment with interatrial septum tissue. The bridging element 12 may then be held in tension by way of a bridge stop 20 (see FIGS. 29 and 30). The anterior bridge stop 20 may be attached to or positioned over the bridging element 12 and advanced with the septal member 30, or alternatively, the bridge stop 20 may be advanced over the bridging element 12 to the right atrium side of the septal member 30 after the septal member has been positioned or deployed. Alternatively, the bridge stop 20 may also be positioned over the LA guide wire 74 and pushed by the deployment catheter 24 into the right atrium. Once in the right atrium, the bridge stop 20 may then be attached to or positioned over the bridging element 12, and the LA guide wire 74 and deployment catheter 24 may then be completely removed from the body.

Figure 44A:
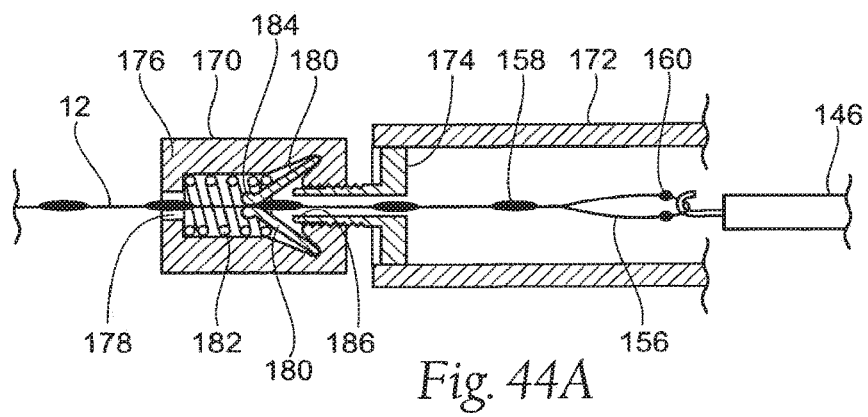
FIG. 44A is a sectional view of a bridge stop which may be used with the implant system of the type shown in FIGS. 10A to 10D, showing the bridging element adjustment feature in the closed position.

FIG. 44A shows a sectional view of a bridge stop 170. The bridge stop 170 is shown coupled to a catheter 172 having a bridge lock adjustment screw 174 at the catheter tip. In one embodiment, the bridge lock adjustment screw 174 remains coupled to the bridge stop 170 after an adjustment has been completed. In an alternative embodiment, the bridge lock adjustment screw 174 remains coupled to the catheter 172 for removal after an adjustment has been completed. The bridge stop 170 comprises a housing 176 having a lumen 178 extending axially therethrough. Within the lumen 178 is provided space for means for holding and adjusting the bridging element, such as clamp or law element 180 and a closing spring 182. As can be seen, the clamp element 180 is in a closed position. The clamp tip(s) 184 are urged together by the force applied to the clamp 180 by the closing spring 182. In this closed position, the closing spring 182 exerts a predetermined force on the clamp tips 184, which in turn exert a clamping force on the bridging element 12 to maintain the bridging element's position. The discrete stop elements 158 provide an additional barrier to maintain the bridging element 12 in place and to allow for adjustment of the bridging element 12 to match the predefined spacing of the stop elements.

Alternatively, the catheter 172 may be used to shorten the length (increase tension) of the bridging element 12 while the clamp 180 is closed. A catheter having a hooked tip 146 may be used to snag the exposed loop 156. The adjustment screw 174 is then screwed partially into the bridge stop 170 so as to couple the catheter 172 to the bridge stop 170. While the catheter 172 is held stationary, the bridging element 12 is tugged to a point where the force exerted on the bridging element 12 and associated discrete stop elements 158 is strong enough to overcome the retentive force of the clamp 180, allowing the bridging element 12 and stop element 158 to pass through the clamp tips 184.

As described herein for bridge stop 170 and for alternative bridge stops described below, a relocation readjustment means (i.e., relocation loop 156) may be included to provide the ability to relocate and/or readjust the implant days, months, or even years later. This may be done after the initial implant procedure, or after a previous adjustment.

Figure 44B:
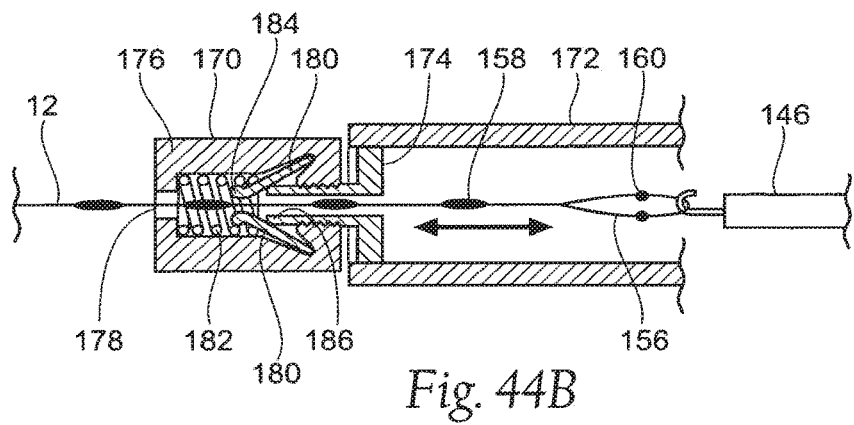
FIG. 44B is a sectional view of the bridge stop of the type shown in FIG. 14A, showing the bridging element adjustment feature in the open position.

FIG. 44B is a sectional view of the bridge stop 170 shown in FIG. 44A, showing the bridge element adjustment feature in the open position. As can be seen, the adjustment screw 174 is shown threaded into the lumen 178 of the bridge lock housing 176. As the adjustment screw 174 is threaded into the bridge stop 170, the tip 186 of the adjustment screw 174 exerts a force on the clamp 180 sufficient to overcome the force of the closing spring 182. The clamp tips 184 open to allow for both shortening and lengthening of the bridging element 12.

The bridge stop 170, and alternative embodiments to be described later, have a predetermined size, e.g., eight millimeters by eight millimeters, allowing them to be positioned adjacent a septal member or a T-shaped member, for example. The bridge locks are also preferably made of stainless steel or other biocompatible metallic or polymer materials suitable for implantation.

Additional alternative bridge stop embodiments are described in section V.

D. Bridging Element Adjustment

The anterior bridge stop 20 is preferably positioned in an abutting relationship to the septal member 30, or optionally may be positioned over the septal member hub 31. The bridge stop 20 serves to adjustably stop or hold the bridging element 12 in a tensioned state to achieve proper therapeutic effects.

With the posterior bridge stop region 14, bridging element 12, and anterior bridge stop region 16 configured as previously described, a tension may be applied to the bridging element 12, either external to the body at the proximal portion of the bridging element 12, or internally, including within the vasculature structure and the heart structure. After first putting tension on the bridging element 12, the implant 10 and associated regions may be allowed to settle for a predetermined amount of time, e.g., five seconds. The mitral valve and its associated mitral valve regurgitation are then observed for desired therapeutic effects. The tension on the bridging element 12 may be repeatably adjusted (as described for each bridge stop embodiment) following these steps until a desired result is achieved. The bridge stop 20 is then allowed to secure the desired tension of the bridging element 12. The bridging element 12 may then be cut or detached at a predetermined distance away from the bridge stop 20, e.g., zero to three centimeters into the right atrium. The remaining length of bridging element 12 may then be removed from the vasculature structure. Alternatively, the bridging element 12 may include a relocation means, such as a hook or loop, or other configurations, to allow for redocking to the bridge stop sites 14, 16, for future adjustment, retrieval, or removal of the implant system 10.

Alternatively, the bridging element 12 may be allowed to extend into the IVC and into the femoral vein, possibly extending all the way to the femoral access point. Allowing the bridging element to extend into the IVC and into the femoral vein would allow for retrieval of the bridging element in the future, for example, if adjustment of the bridging element is necessary or desired.

The bridging element adjustment procedure as just described including the steps of placing a tension, waiting, observing, and readjusting if necessary is preferred over a procedure including adjusting while at the same time—or real-time—observing and adjusting, such as where a physician places a tension while at the same time observes a real-time ultrasound image and continues to adjust based on the real-time ultrasound image. The waiting step is beneficial because it allows for the heart and the implant to go through a quiescent period. This quiescent period allows the heart and implant to settle down and allows the tension forces and devices in the posterior and anterior bridge stop regions to begin to reach an equilibrium state. The desired results are better maintained when the heart and implant are allowed to settle prior to securing the tension compared to when the mitral valve is viewed and tension adjusted realtime with no settle time provided before securing the tension.

Figure 31:
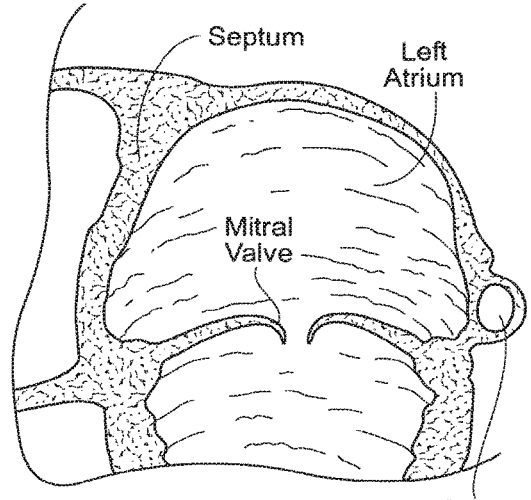
FIG. 31 is an anatomic section view of the left atrium and associated mitral valve structure, showing mitral dysfunction.
Figure 32:
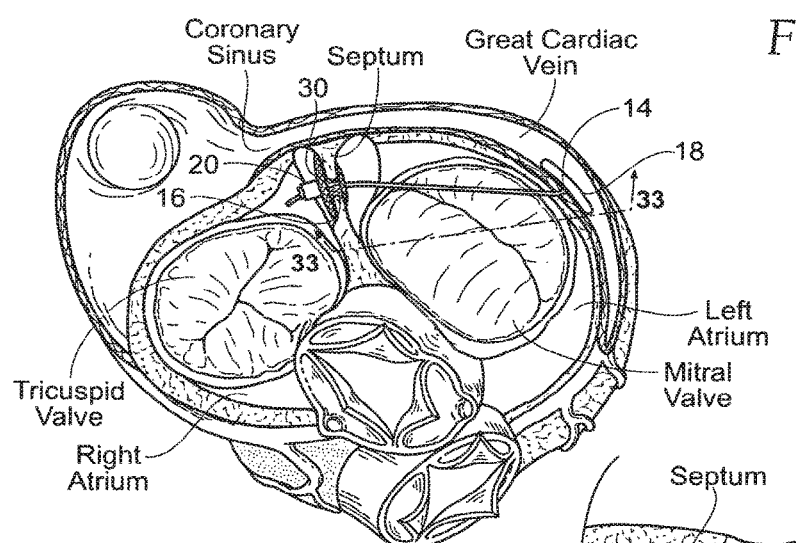
FIG. 32 is an anatomic superior view of a section of the human heart, showing the presence of an implant system of the type shown in FIGS. 10A and 10B.
Figure 33:
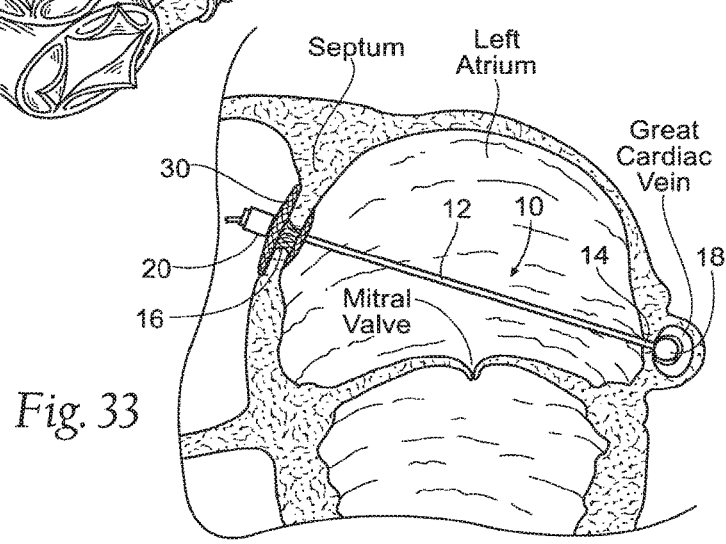
FIG. 33 is an anatomic section view of the implant system taken generally along line 33-33 in FIG. 32, showing the presence of an implant system of the type shown in FIGS. 10A and 10B, and showing proper coaptation of the mitral valve leaflets.

FIG. 31 shows an anatomical view of mitral valve dysfunction prior to the implantation of the implant 10. As can be seen, the two leaflets are not coapting, and as a result the undesirable back flow of blood from, the left ventricle into the left atrium can occur. After the implant 10 has been implanted as just described, the implant 10 serves to shorten the minor axis of the annulus, thereby allowing the two leaflets to coapt and reducing the undesirable mitral regurgitation (see FIGS. 32 and 33). As can be seen, the implant 10 is positioned within the heart, including the bridging element 12 that spans the mitral valve annulus, the anterior bridge stop 20 and septal member 30 on or near the fossa ovalis, and the posterior bridge stop 18 within the great cardiac vein.

IV. Alternative Implantation Steps

The steps of implantation as previously described may be altered due to any number of reasons, such as age, health, and physical size of patient, and desired therapeutic effects. In one alternative embodiment, the posterior T-shaped bridge stop 120 (or alternative embodiments) is implanted via a GCV approach, instead of the left atrial approach as previously described. In an additional alternative embodiment, the coring procedure of the left atrial wall is replaced with a piercing procedure from the great cardiac vein to the left atrium.

A. GCV Approach

As previously described, penetration of the cutting catheter 80 into the great cardiac vein is confirmed under image guidance (see FIG. 26). Once penetration is confirmed, the LA guide wire 74 is advanced into the great cardiac vein and into the GCV catheter 40. The LA guide wire 74 is further advanced through the GCV catheter 40 until its end exits the body (preferably at the superior vena cava sheath). The LA catheter 60 and the GCV catheter 40 may now be removed. Both the LA guide wire 74 and the GCV guide wire 54 are now in position for the next step of establishing the transseptal bridging element 12 (see FIG. 35A). At this point, an optional exchange catheter 28 may be advanced over the LA guide wire 74, starting at either end of the guide wire 74 and entering the body at either the femoral sheath or superior vena cava sheath, and advancing the exchange catheter 28 until it exits the body at the other end of the guide wire 74. The purpose of this exchange catheter is to facilitate passage of the LA guidewire 74 and bridging element 12, in a procedure to be described below, without cutting or injuring the vascular and heart tissues. In a preferred embodiment, the exchange catheter 28 is about 0.040 to 0.060 inch ID, about 0.070 to 0.090 inch OD, about 150 cm in length, has a lubricious ID surface, and has an atraumatic soft tip on at least one end so that it can be advanced through the vasculature without injuring tissues. It is to be appreciated that the ID, OD, and length may vary depending on the specific procedure to be performed.

In the GCV approach, the trans-septal bridging element 12 is implanted via a GCV to left atrium approach. A predetermined length, e.g., two meters, of bridging element 12 (having a leading end and a trailing end) is connected at the leading end to the tip of the LA guide wire 74 that had previously exited the body at the superior vena cava sheath and the femoral sheath. In this embodiment, the LA guide wire 74 serves as the loop guide wire, allowing the bridging element to be gently pulled or retracted into and through at least a portion of the vasculature structure and into a heart chamber. The vascular path of the bridging element may extend from the superior vena cava sheath through the coronary sinus into a region of the great cardiac vein adjacent the posterior mitral valve annulus, and from the great cardiac vein through atrial tissue into the left atrium, and from the left atrium into the right atrium through the interatrial septum, and from the right atrium to the femoral sheath.

Figure 34A:
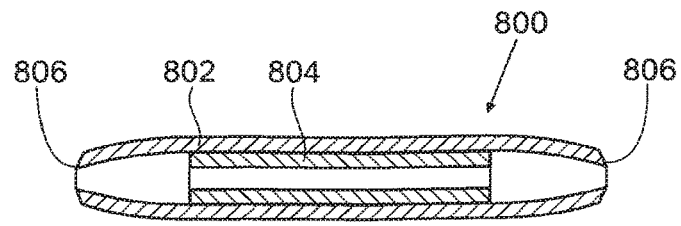
FIGS. 34A to 34D are sectional views of a crimp tube for connecting a guide wire to a bridging element, and showing the variations in the crimps used.
Figure 34B:
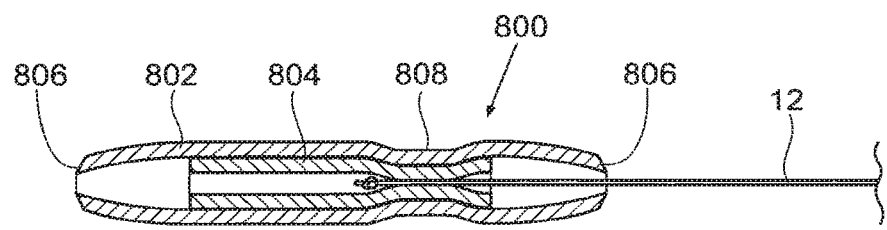

As can be seen in FIGS. 34A to 34D, a crimp tube or connector 800 may be used to connect the bridging element 12 to at least one end of the LA guide wire 74. FIG. 34A shows a crimp tube 800 preferably having an outer protective shell 802 and an inner tube 804. The outer protective shell 802 is preferably made of a polymeric material to provide atraumatic softness to the crimp tube, although other crimpable materials may be used. The inner tube 804 may be made of a ductile or malleable material such as a soft metal so as to allow a crimp to hold the bridging element 12 and guide wire 74 in place. The crimp tube ends 806 may be gently curved inward to aid in the movement of the crimp tube as the tube 800 moves through the vasculature. It is to be appreciated that the crimp tube may simply comprise a single tube made of a ductile or malleable material.

Figure 34C:
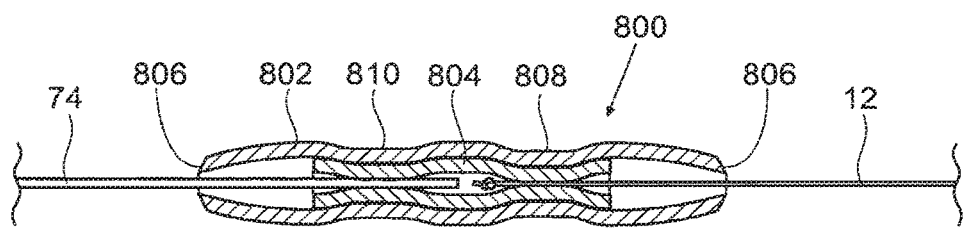
Figure 34D:
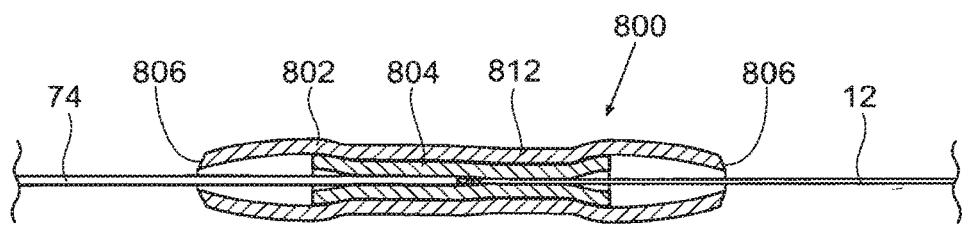

The bridging element 12 is positioned partially within the crimp tube 800. A force is applied with a pliers or similar crimping tool to create a first crimp 808 (see FIG. 34B). The end of the bridging element may include a knot, such as a single overhand knot, to aid in the retention of the bridging element 12 within the crimp tube. Next, the LA guide wire 74 is positioned partially within the crimp tube 800 opposite the bridging element 12, A force is again applied with a pliers or similar crimping tool to create a second crimp 810 (see. FIG. 34C). Alternatively, both the bridging element 12 and the guide wire 74 may be placed within the crimp tube 800 at opposite ends and a single crimp 812 may be used to secure both the bridging element 12 and the guide wire 74 within the crimp tube (see FIG. 34D). It is to be appreciated that the crimp tube 800 may be attached to the bridging element 12 or guide wire prior to the implantation procedure so as to eliminate the step of crimping the bridging element 12 within the crimp tube 800 during the implantation procedure. The guide wire 74 is now ready to be gently retracted. It can also be appreciated that apparatus that uses adhesives or alternatively pre-attached mechanisms that snap together may also be used for connecting bridge elements to guidewires.

Figure 35A:
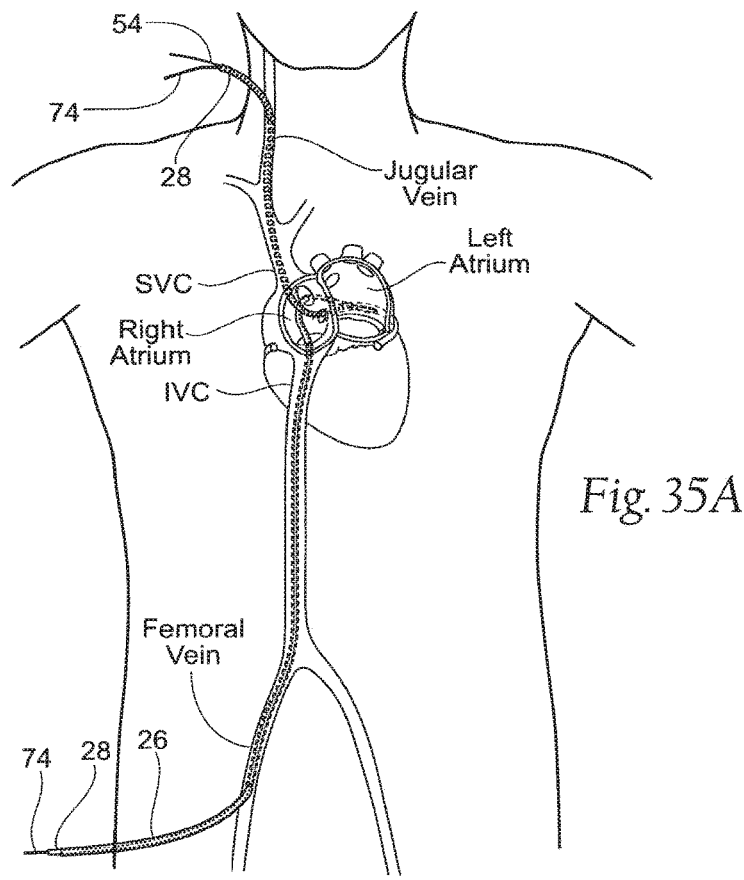
FIG. 35A is an anatomic partial view of a patient depicting access points used for implantation of an implant system, and also showing a loop guide wire accessible to the exterior the body at two locations.
Figure 35B:
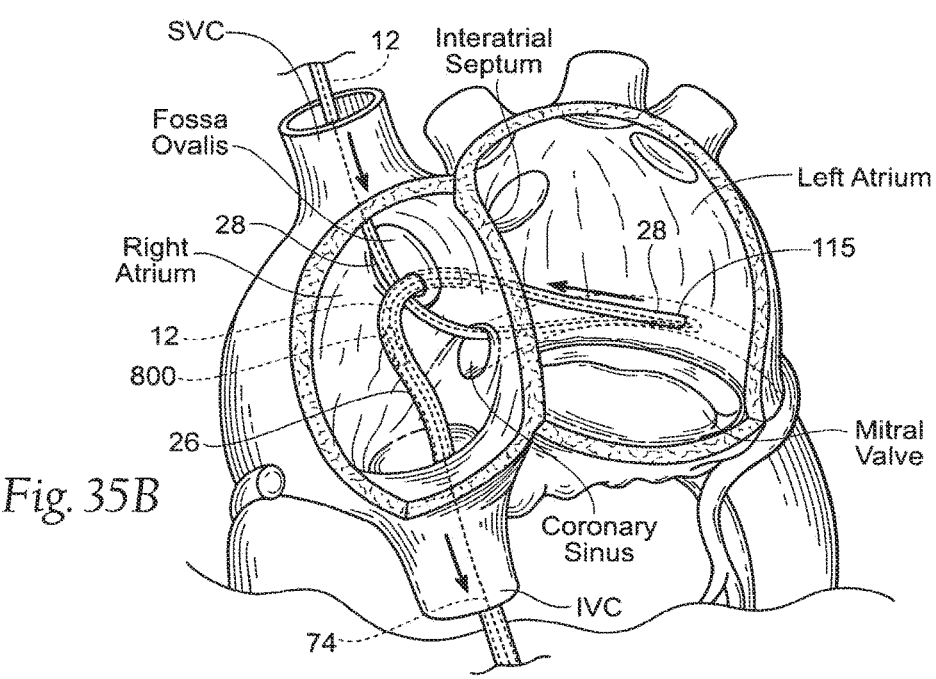
FIG. 35B is an anatomic view depicting a representative alternative catheter-based device for implanting an implant system of the type shown in FIGS. 10A to 10C, and showing a bridging element being pulled through the vasculature structure by a loop guide wire.
Figure 36A:
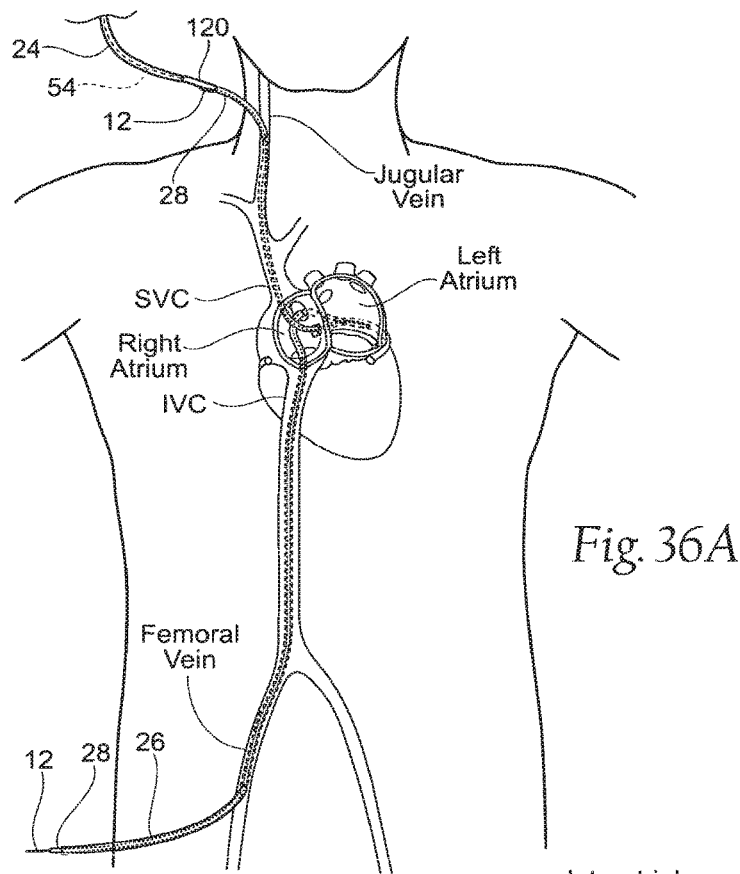
FIG. 36A is an anatomic partial view of a patient showing a bridge stop connected to a bridging element in preparation to be pulled and/or pushed through the vasculature structure and positioned within the great cardiac vein.

As can be seen in FIG. 35B, the LA guide wire 74 is gently retracted, causing the bridging element 12 to follow through the vasculature structure. If the optional exchange catheter 28 is used (as shown in FIGS. 35A and 35B), the LA guidewire 74 retracts through the lumen of the exchange catheter 28 without injuring tissues. The LA guide wire 74 is completely removed from the body at the femoral vein sheath, leaving the bridging element 12 extending from eater or the body (preferably at the femoral sheath), through the vasculature structure, and again exiting at the superior vena cava sheath. The LA guide wire 74 may then be removed from the bridging element 12 by cutting or detaching the bridging element 12 at or near the crimp tube 800.

Figure 36B:
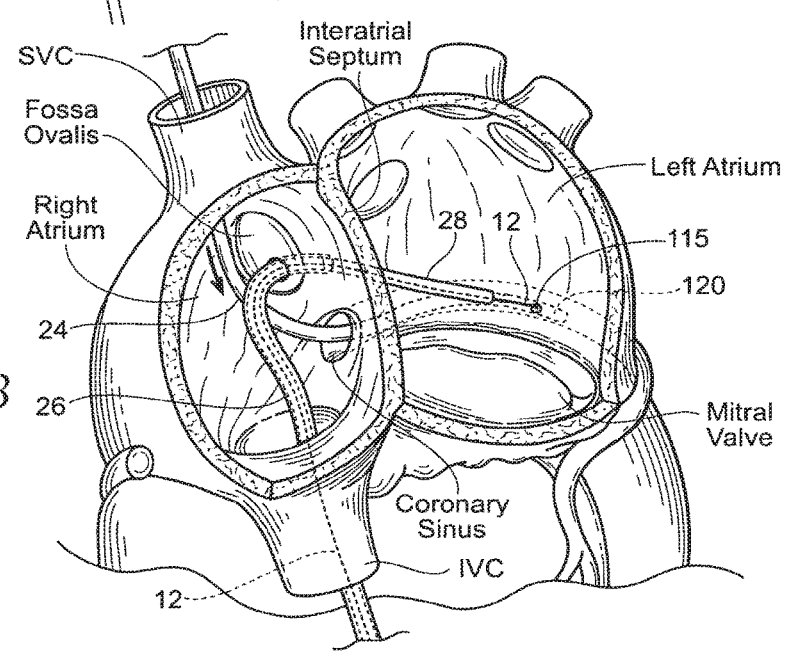
FIG. 36B is an anatomic view depicting a representative alternative catheter-based device for implanting a system of the type shown in FIGS. 10A to 10C, and showing a bridge stop being positioned within the great cardiac vein.

A posterior bridge stop, such as a T-shaped bridge stop 120 is preferably connected to the trailing end of bridging element 12 extending from the superior vena cava sheath. The T-shaped bridge stop 120 is then positioned onto or over the GCV guide wire 54. A deployment catheter 24 is then positioned onto or over the GCV guide wire 54 and is used to advance or push the T-shaped bridge stop 120 and bridging element 12 through the right atrium, through the coronary sinus, and into the great cardiac vein. If the optional exchange catheter 28 is used, the exchange catheter is gently retracted with the bridging element 12 or slightly ahead of it (see FIGS. 36A and 36B). Optionally, the bridging element 12 may be pulled from the femoral vein region, either individually, or in combination with the deployment catheter 24, to advance the T-shaped bridge stop 120 and bridging element 12 into position in the great cardiac vein. The GCV guide wire 54 is then retracted letting the T-shaped bridge stop 120 separate from the GCV guide wire 54 and deployment catheter 24. Preferably under image guidance, and once separation is confirmed, the bridging element 12 is gently pulled to position the T-shaped bridge stop 120 in abutment against the venous tissue within the great cardiac vein and centered over the GCV access lumen 115. The deployment catheter 24 and optional exchange catheter 28 may then be removed.

Figure 28:
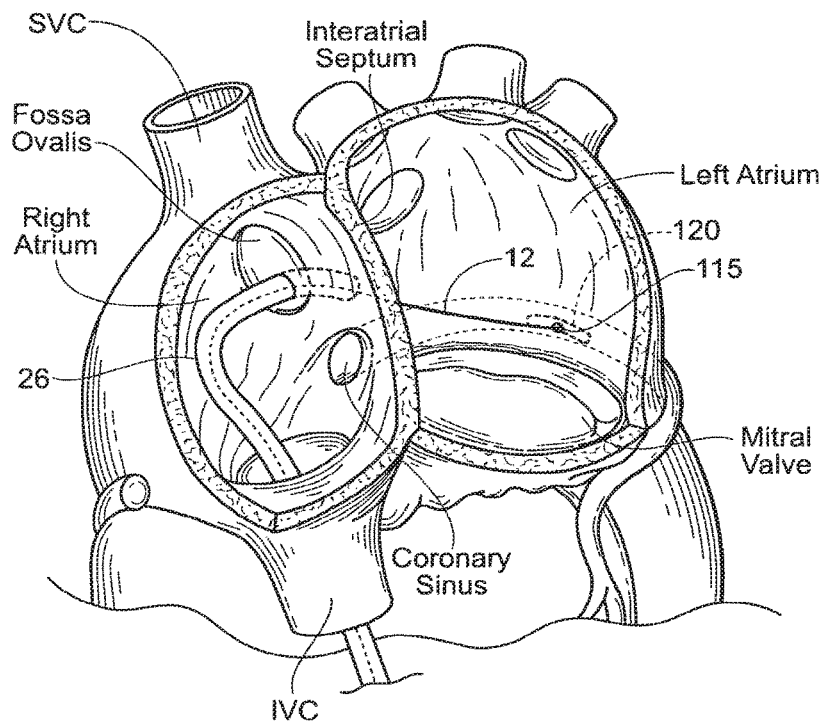
Figure 30:
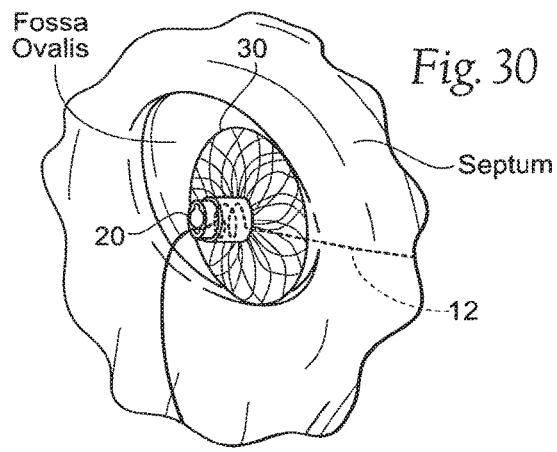

The T-shaped bridge stop 120 and the attached bridging element 12 remain within the great cardiac vein. The length of bridging element 12 extends from the posterior T-shaped bridge stop 120, through the left atrium, through the fossa ovalis, through the vasculature, and preferably remains accessible exterior the body. The bridging element 12 is now ready for the next step of establishing the anterior bridge stop region 16, as previously described, and as shown in FIGS. 28 to 30.

B. Piercing Procedure

In this alternative embodiment, the procedure to core a lumen from the left atrium into the great cardiac vein is replaced with a procedure where a sharp-tipped guide wire within the great cardiac vein is used to create a passage from the great cardiac vein into the left atrium. Alternative embodiments for the magnetic head of both the GCV catheter 40 and the LA catheter 60 are preferably used for this procedure.

Figure 45A:
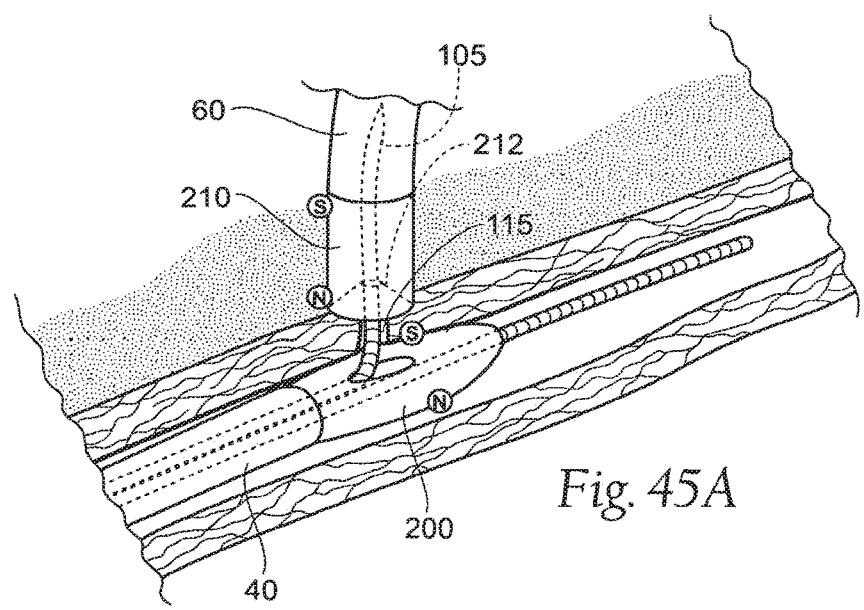
FIG. 45A is an anatomic partial perspective view of alternative magnetic catheter heads, with one catheter shown in the left atrium and one catheter shown in the great cardiac vein, and showing a side to end configuration.

FIGS. 45A and 45B show an end to side polarity embodiment for the GCV catheter magnetic head 200 and the LA catheter magnetic head 210. Alternatively, a side to side polarity may be used. The GCV catheter magnetic head 200 can maintain the same configuration for both the end to side polarity and the end to end polarity, while the LA catheter magnetic head 215 is shown essentially rotated ninety degrees for the side to side polarity embodiment (See FIG. 46).

As seen in FIG. 45B, the GCV catheter magnetic head 200 includes a dual lumen configuration. A navigation guide wire lumen 202 allows the GCV guide wire 54 to extend through the cone or bullet shaped end 204 of the head 200 in order to steer the GCV catheter 40 into position. A second radially curved side hole lumen 206 allows the sharp tipped guide wire 105 (or tri-blade 100, for example) to extend through the head 200 and directs the sharp tipped guide wire 105 into the LA catheter magnetic head 210. The LA catheter magnetic head 210 includes a funneled end 212 and a guide wire lumen 214 (see FIG. 45C). The funneled end 212 directs the sharp tipped guide wire 105 into the lumen 214 and into the LA catheter shaft 65.

FIG. 46 shows the alternative embodiment of the LA catheter magnetic head 215 used with the side to side polarity embodiment. The head 215 may have the same configuration as the GCV catheter magnetic head 42 shown in FIGS. 39 and 40 and described in section III. The head 215 includes a navigation guide wire lumen 216 at the cone or bullet shaped end 218, and a side hole 220. The side hole 220 funnels the sharp tipped guide wire 105 (or tri-blade 100, for example), from the GCV catheter 40 to the LA catheter 60 and directs the guide wire 105 into the LA catheter shaft 65.

In use, both the GCV catheter 40 and the LA catheter 60 are advanced into the great cardiac vein and left atrium as previously described. The GCV catheter 40 and the LA catheter 60 each includes the alternative magnetically attractant head portions as just described. As best seen in FIGS. 45A and 45B, a sharp-tipped guide wire 105 is advanced through the GCV catheter 40 to the internal wall of the great cardiac vein. The sharp-tipped guide wire 105 is further advanced until it punctures or pierces the wall of the great cardiac vein and the left atrium, and enters the funneled end 212 within the LA catheter head 210. The sharp-tipped guide wire 105 is advanced further until it exits the proximal end of the LA catheter 60. Both the GCV catheter 40 and the LA catheter 60 may now be removed, leaving the GCV guide wire 54 and the sharp-tipped guide wire 105 in place. The posterior T-shaped bridge stop 120 is now implanted via the GCV approach, as previously described, and as shown in FIGS. 35A to 36B.

V. Alternative Bridge Stop Embodiments

Alternative embodiments of bridge stops may be used and are herein described. The bridge stop may serve to secure the bridging element 12 at the anterior bridge stop region 16 or the posterior bridge stop region 14, or both. It is to be appreciated that the alternative embodiments of the bridge stop may comprise a single element, or may also comprise multiple elements. In addition, the alternative embodiments of the bridge stop may feature adjustment of the bridging element to tighten only, or to loosen only, or to loosen and tighten.

FIG. 47 shows a perspective view of an alternative embodiment of an implant system 10 of the type shown in FIGS. 10A to 10D. The implant system 10 of FIG. 47 shows the use of an exposed loop 156 allowing for adjustment or removal of the implant system, for example. As can be seen, a catheter having a hooked tip 146 may be used to snag the exposed loop 156. Radio-opaque markers 160 may be used to facilitate the grasping or snagging of the exposed loop 156. The bridging element 12 also is shown including the use of discrete stop elements 158 in conjunction with the anterior bridge stop 170.

FIG. 48 is a perspective view of an alternative embodiment of a bridge stop 390 in accordance with the present invention. The alternative bridge stop 390 preferably includes a toothed ribbon 392 and a bridge stop housing 394. The toothed ribbon 392 comprises all or a portion of the bridging element 12 and includes at least one row of spaced apart teeth 396 positioned along at least one edge of the ribbon. The housing includes a locking collar 398 at one end. The locking collar 398 includes a rectangular shaped opening 400 so as to allow for free movement of the toothed ribbon 392 when the collar is in an open position (see FIG. 48), and to engage the teeth 396 when the collar 398 is in a locked position (see FIG. 49). Additional bridging element or a suture type material 402 may be coupled to the toothed ribbon 492 so as to allow the housing 494 and locking collar 398 to be positioned onto the toothed ribbon.

In use, the bridge stop 390 allows the length of the bridging element, including the toothed ribbon 392, to be adjusted by rotating the locking collar 398 to the open position (see FIG. 48). A catheter (not shown) is desirably used to grasp the locking collar 398 and to provide the rotation function. Once the locking collar is in the open position, the ribbon 392 may be freely moved thereby adjusting the length of the bridging element 12. Once a desired tension is established, the catheter is again used to rotate the locking collar 398 ninety degrees so as to engage the teeth 396 and hold the ribbon 392 in place (see FIG. 49).

FIG. 50 is a perspective view of an alternative embodiment of a bridge stop 410 in accordance with the present invention. The alternative bridge stop 410 preferably includes an adjusting collar or nut 414, a locking collar or nut 416, and a threaded shaft 412, the threaded shaft 412 comprising all or a portion of the bridging element 12, As can be seen, both the adjusting nut 414 and the locking nut 416 may include features to facilitate rotation. Adjusting nut 414 is shown with a rod or rods 418 extending radially from the nut. Locking nut 416 is shown with one or more recesses 420 on the perimeter of the nut. These rotation features allow a catheter to be placed over the threaded shaft 412 and both the adjusting nut 414 and locking nut 416 so as to loosen the locking nut 416, adjust the position of the adjusting nut 414, thereby adjusting the tension on the bridging element 12, and then retighten the locking nut 416. Additional bridging element or a suture material 402 may be coupled to the threaded shaft 412 so as to allow the adjusting nut 414 and locking nut 416 to be positioned onto the threaded shaft.

Alternatively, a single nut 422 may be used having self locking threads, such as nylon threads (see FIG. 51). A single nut has an advantage of reducing the number of steps necessary to adjust the bridging element 12.

FIG. 52 is a perspective view of an alternative embodiment of a bridge stop 430 in accordance with the present, invention. The alternative bridge stop 430 preferably includes a perforated ribbon 432 and a bridge stop housing 434. The perforated ribbon 432 comprises all or a portion of the bridging element 12 and includes at least one row of spaced apart perforations 436 positioned along a length of the ribbon. Additional bridging element or a suture material 402 may be coupled to the perforated ribbon 432 so as to allow the bridge stop housing 434 to be positioned onto the perforated ribbon.

Figure 53:
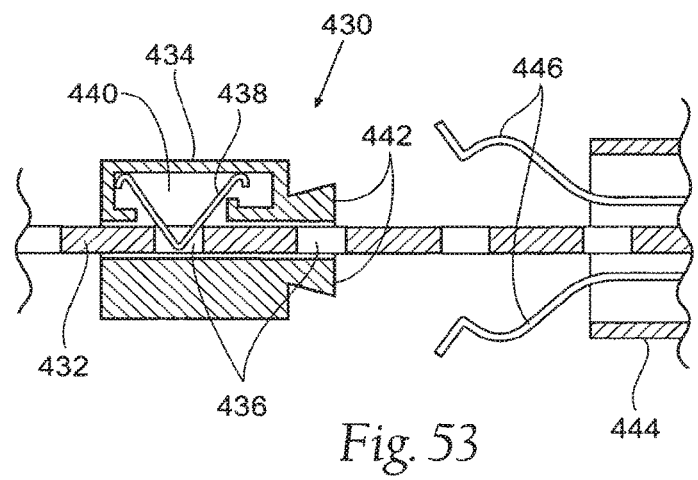
FIG. 53 is a sectional view of the bridge stop of the type shown in FIG. 52, showing the bridging element adjustment feature in the closed position and showing an adjustment catheter tip prior to coupling to the bridge stop for bridging element adjustment.
Figure 54:
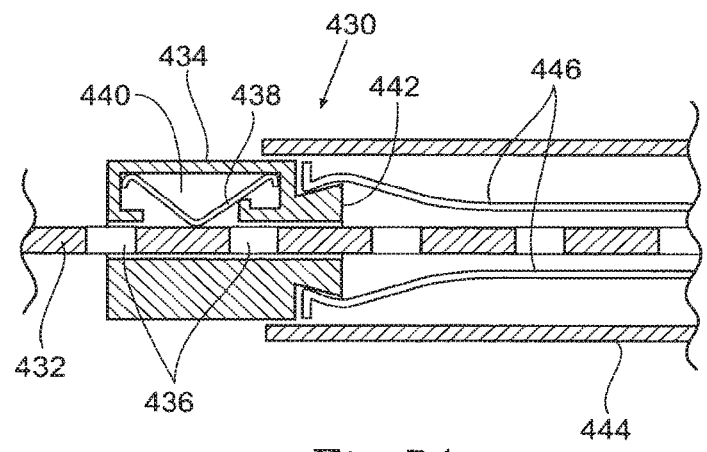
FIG. 54 is a sectional view of the bridge stop of the type shown in FIG. 52, showing the bridging element adjustment feature in the open position and showing the adjustment catheter tip coupled to the bridge stop for bridging element adjustment.

Referring to FIGS. 53 and 54, the housing includes a locking spring 438 positioned within recess 440. The housing 434 may also include a tab or tabs 442 to allow coupling of adjustment catheter 444. As can be seen, the catheter 444 includes a coupling arm or arms 446 to couple to the housing tabs 442 (see FIG. 54). This coupling between the housing and the adjustment catheter maintains the position of the bridge stop housing 434 so as to allow the perforated ribbon 432 to be adjusted to increase or decrease the length of the bridging element.

FIG. 53 shows the bridge stop 430 in a locked configuration. The locking spring 438 is shown extending into a perforation 436 within the ribbon 432. In order to adjust the bridging element, the catheter 444 is first coupled to the bridge stop housing tabs 442 by engaging the catheter coupling arms 446. As can be seen in FIG. 54, the adjusting catheter 444 is coupled to the bridge stop 430. In this adjustment configuration, the perforated ribbon 432 is able to be pulled or pushed, causing the locking spring 438 to temporarily flex out of the perforation 436 and into the available recess 440. The perforations 436 may have rounded edges so as to facilitate the locking spring 438 to flex out of the perforation 436 when the ribbon 432 is adjusted. The ribbon is adjusted to a point where the locking spring 438 again flexes into the perforation 436 to maintain the position of the bridging element 12.

Figure 55:
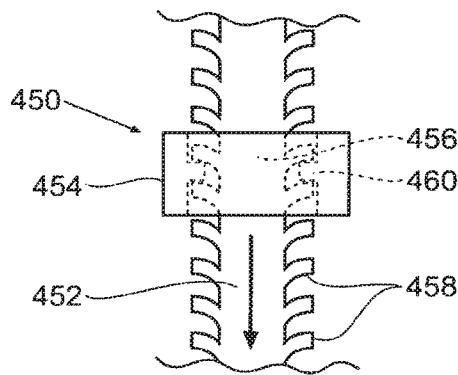
FIG. 55 is a top view depicting an alternative embodiment of a bridge stop having a bridging element adjustment feature.
Figure 56:
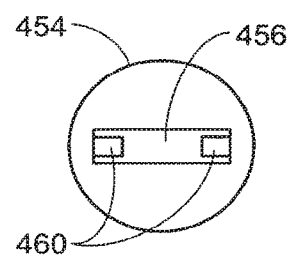
FIG. 56 is a front view of the bridge stop shown in FIG. 55, showing retentive tabs within the bridge stop.

FIGS. 55 and 56 show an alternative embodiment of a bridge stop 450 in accordance with the present invention. The alternative bridge stop 450 preferably includes a one way toothed ribbon 452 and a bridge stop housing 454 having a lumen 456 extending axially therethrough. The one way toothed ribbon 452 comprises all or a portion of the bridging element 12 and includes at least one row of spaced apart teeth 458 positioned along at least one edge of the ribbon. In one embodiment, the teeth 158 may be slanted to allow for one way adjustment of the ribbon 452 (see FIG. 55) Within the housing lumen 456 is provided means for holding in place the one way toothed ribbon 452. As can be seen in FIGS. 55 and 56, tab(s) 460 or the like are positioned within the housing lumen 456 to engage the slanted teeth 458 and allow the teeth to pass in one direction but not bi-directionally. In one embodiment, the slanted teeth 458 are generally pliable while the tabs 460 are generally rigid, so as to allow the housing to be pushed over the teeth 458 in one direction but resist movement of the housing 454 in the opposite direction. In an alternative embodiment, the slanted teeth 458 are generally rigid while the tabs 460 are generally pliable. It is to be appreciated that bridge stop 450 could also be modified to include generally pliable teeth 458 and tabs 460 to allow for bi-directional movement of the toothed ribbon 452.

FIGS. 57A through 582 show an additional alternative embodiment of a bridge stop 470 in accordance with the present invention. FIGS. 57A through 57C show the bridge stop 470 including a bridging element 12 in a restrained configuration, while FIGS. 58A through 58C show the bridge stop 470 including a bridging element 12 in an unrestrained configuration. The alternative bridge stop 470 preferably includes a housing 472, which may be tubular in shape, although not necessary; the housing including a top side 474, bottom side 476, inner surface 478, and outer surface 480. Within the housing is positioned a slanted wall or ramp 482 extending from at or near the top side 474 to the inner surface 478 generally at or near the bottom side 476. Positioned within the ramp 482 is a groove or slot 484 extending to an offset circular opening 486. The slot 484 is positioned at or near the top side 474 and extends to the circular opening 486 positioned at or near the bottom side 476.

FIGS. 57A through 57C show the bridging element 12 and associated discrete stop elements 158 in the restrained position. As can be seen, the slot 484 is sized so as to allow only the bridging element 12 to move within the slot. Tension applied to the bridging element 12 in an upward direction (toward the housing top side 474) allows the ramp 482 to facilitate the movement of the stop element 158 and bridging element 12 into the slot 484 and to the restrained position, as shown. The stop element 158 prevents the bridging element 12 from substantially moving in the upward direction.

FIGS. 58A through 58C show the bridging element 12 and associated discrete stop elements 158 in the unrestrained position. In this configuration, the length (tension) of the bridging element 12 may be adjusted. As can be seen, the circular opening 486 is sized and configured to allow the bridging element 12, including the discrete stop elements 158, to pass through the opening 486. It is to be appreciated that the opening can take on any shape which associates with the shape of the stop elements 158. Tension applied to the bridging element 12 (toward the housing bottom side 476) allows the ramp 482 to facilitate the movement of the stop element 158 and bridging element 12 down the ramp 482 (i.e., out of the slot 484 and into the opening 486) and to the unrestrained position, as shown. The stop elements 158 (and bridging element 12) are free to pass through the circular opening 486. It is to be appreciated that the bridging element 12 and the discrete stop elements 158 may comprise a single element, or may comprise individual stop elements coupled to the bridging element, for example.

FIGS. 59A through 60C show an alternative embodiment of the bridge stop 470. The alternative bridge stop 970 preferably includes the addition of a rotating gate 988. The rotating gate 988 provides a convenient mechanism to allow the bridging element 12 and the discrete stop elements 158 to be reset allowing for adjustment during a procedure. FIGS. 59A through 59C show the bridge stop 970 including a bridging element 12 in a restrained configuration, while FIGS. 60A through 60C show the bridge stop 970 including a bridging element 12 in an unrestrained configuration.

The alternative bridge stop 970 preferably includes a housing 972, which may be tubular in shape, although not necessary; the housing including a top side 974, bottom side 976, inner surface 978, and outer surface 980. Within the housing is positioned a slanted wall or ramp 982 extending from at or near the top side 974 to the inner surface 978 generally at or near the bottom side 976. Positioned within the ramp 982 is a groove or slot 984 extending to an offset circular opening 986. The slot 984 is positioned at or near the top side 974 and extends to the circular opening 986 positioned at or near the bottom side 976.

The rotating gate 988 positioned within the housing 972 includes a slot 989 sized and configured to generally match the length and width of slot 984 positioned within the ramp 982. The rotating gate 988 may be hinged or otherwise rotatably coupled to the housing 972 or ramp 982. As shown, the rotating gate 988 includes pins or tabs 990 positioned within apertures 991 to allow the gate 988 to pivot or rotate about the tabs 990. The apertures 991 are positioned within the housing 972 so as to allow the rotating gate 988 to pivot or rotate at or near where the slot 984 within the ramp 982 meets the offset circular opening 986. The rotating gate 988 may be held in a restrained position (as shown in FIGS. 59A through 59C) by way of a spring 994, for example, or the gate may be allowed to move freely, its movement dependant on the tension of the bridging element 12 and the discrete stop elements 158. Coupled to the outer edge 992 of the rotating gate 988 may be a reset loop 993 having radio-opaque markers 160.

FIGS. 59A through 59C show the bridging element 12 and associated discrete stop elements 158 in the restrained position. As can be seen, the slot 984 in the ramp 982 and the slot 989 in the gate 988 are sized so as to allow only the bridging element 12 to move within each slot. Tension applied to the bridging element 12 in an upward direction (toward the housing top side 974) allows the gate 988 to facilitate the movement of the stop element 158 and bridging element 12 into the slot 988 (and slot 984) and to the restrained position, as shown. The stop element 158 prevents the bridging element 12 from substantially moving in the upward direction.

FIGS. 60A through 60C show the bridging element 12 and associated discrete stop elements 158 in the unrestrained position. In this configuration, the length (tension) of the bridging element 12 may be adjusted. As can be seen, the circular opening 986 is sized and configured to allow the bridging element 12, including the discrete stop elements 158, to pass through the opening 986. It is to be appreciated that the opening can take on any shape which associates with the shape of the stop elements 158. With the aid of a catheter (not shown) the reset loop 993 is pulled in a downward direction (toward the housing bottom side 976) to urge the bridging element 12 and the discrete stop elements 158 down the rotating gate 988 (i.e., out of the slot 989) and into the offset circular opening 986 and to the unrestrained position for adjustment, as shown. The stop elements 158 (and bridging element 12) are free to pass through the circular opening 986. It is to be appreciated that the bridging element 12 and the discrete stop elements 158 may comprise a single element, or may comprise individual stop elements coupled to the bridging element, for example.

FIG. 61 is a perspective view of an additional alternative embodiment of a bridge stop 500 in accordance with the present invention. The alternative slideable bridge stop 500 preferably includes a toothed ribbon 502 and a bridge stop slider component 504. The toothed ribbon 502 comprises all or a portion of the bridging element 12 and includes at least one row of spaced apart teeth 506 positioned along at least one edge of the ribbon. As shown, the toothed ribbon 502 includes a row of spaced apart teeth 506 on each side of the ribbon. The teeth 506 are shown positioned in a non-staggered saw tooth pattern. In one embodiment, the toothed ribbon 502 has a height H1 of about 0.060 inches, although the height H1 may vary. The slider component 504 may comprise a grooved component 508 and a snap component 510.

FIGS. 62 and 63 show the grooved component 508 (FIG. 63 showing the grooved component in section). As can be seen, the grooved component may be generally tubular in shape and includes a lumen 512 extending therethrough. Positioned generally midway between a first end 514 and a second end 516, on the outer surface 518, is a groove or channel 520 extending circumjacent the outer surface 518. Positioned within the channel 520 may be a dimple or depression 522. Desirably the channel 520 may include four dimples 522 positioned ninety degrees apart from each other. The grooved component 508 may also include a torquing pin or pins 524 extending radially from the outer surface 518.

Within the lumen 512 of the grooved component 508 are positioned axisymmetric grooves 526 (seen particularly in FIG. 63). The grooves 526 may not extend completely around the inner diameter of the lumen 512. At least one bridging element channel 528, and desirably two parallel channels, extends the length of the grooved component 508.

FIG. 64 shows the snap component 510 which is rotatably positioned partially over and through the grooved component 508. The snap component 510 comprises a base 530, at least one finger 532 extending from the base 530, and a base extension 534. The base 530 and base extension include a channel 536 extending therethrough. The at least one finger desirably comprises four fingers 532, one finger per dimple 522 on the grooved component 508. At the tip of each finger 532 may be positioned a tab 538 that works in cooperation with dimples 522 to act as a detent to restrict rotational movement of the snap component 510 about the grooved component 508.

Figure 65:
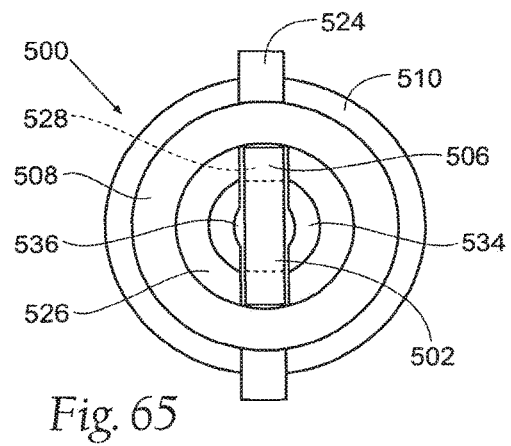
FIG. 65 is a front view of the bridge lock shown in FIG. 61, and showing the bridging element adjustment feature in the unlocked position.

In use, the snap component 510 is positioned over the grooved component 508, as can be seen in FIG. 61. The toothed ribbon 502 is allowed to be adjusted (lengthening or shortening of the bridging element) when the channel 528 in the grooved component 508 lines up with the channel 536 in the snap component. In this adjustment configuration (see FIG. 65), the spaced apart teeth 506 on the toothed ribbon 502 are not restrained by the grooves 526 positioned with the grooved component 508, and the ribbon 502 is free to slide within the bridge stop 500. The detent feature (dimples 522 and tabs 538) provide predefined adjustment and restrained positions for the bridge stop 500 to more simply convert between the adjustment configuration and the restrained configuration.

Figure 66:
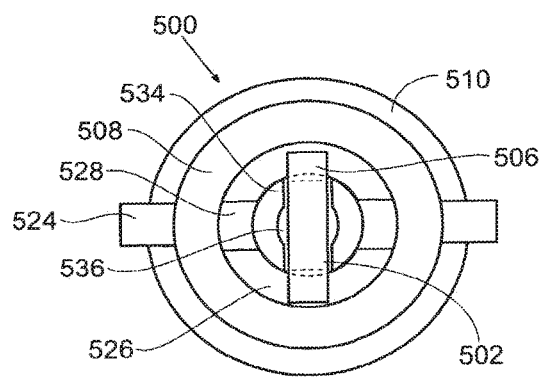
FIG. 66 is a front view of the bridge lock shown in FIG. 61, and showing the bridging element adjustment feature in the locked position.

When a desired tension is achieved on the bridging element 12, a catheter having a torquing tool 540 (see FIG. 67) on its distal end is used to rotate the grooved component 508 in either a clockwise or counter-clockwise direction while maintaining the position of the toothed ribbon (and snap component 510) so as to engage the spaced apart teeth 306 within the matching grooves 526 of the grooved component 508, thereby restraining the toothed ribbon 502 (see FIG. 66). Again, the detent feature (dimples 522 and tabs 538) provides a predefined restrained position to maintain the bridge stop 500 in this restrained configuration after the torquing tool 540 has been removed.

Figure 67:
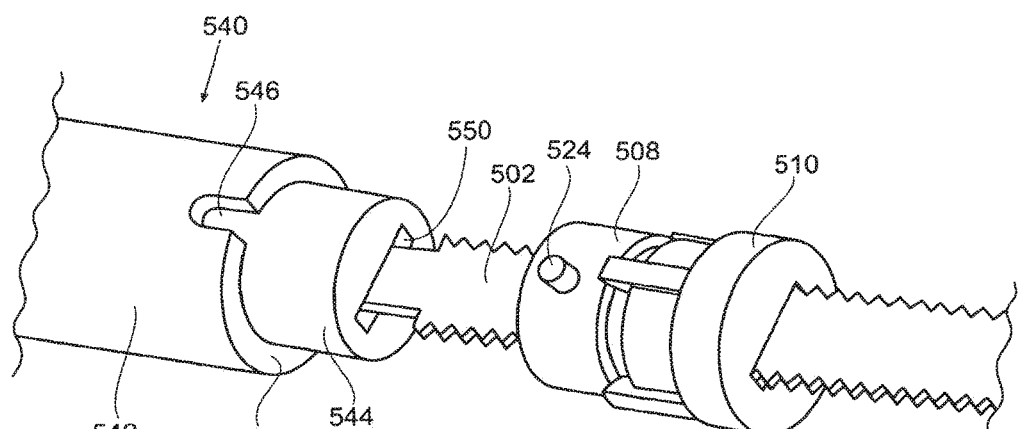
FIG. 67 is a perspective view of the bridge lock shown in FIG. 61, and showing an adjustment catheter having a pair of interacting catheter tips, the inner torquer tip being positioned on the toothed bridging element, with the outer torquer tip yet to be positioned on the bridge lock.

As can be seen in FIG. 67, the torquing tool 540 may comprise an outer torquer 542 and an inner torquer 544. The outer torquer 542 includes at least one recess 546 at its distal end 548 to engage the torquing pin or pins 524 on the grooved component 508. The inner torquer 544 (positioned within the outer torquer 542) includes a channel 550 sized and configured to allow the toothed ribbon to extend within the inner torquer 544.

In an alternative embodiment of the slideable bridge stop 500, the screw threaded bridge stop 560 (see FIG. 68) preferably includes a toothed ribbon 562 and a bridge stop screw threaded component 564. The toothed ribbon 562 comprises all or a portion of the bridging element 12 and includes at least one row of spaced apart teeth 566 positioned along at least one edge of the ribbon. As shown, the toothed ribbon 562 includes a row of spaced apart teeth 566 on each side of the ribbon. The teeth 566 are shown positioned in a staggered saw tooth pattern. In one embodiment, the toothed ribbon 562 has a height H2 of about 0.060 inches, although the height H2 tray vary. The screw threaded component 564 may comprise a threaded component 568 and a base component 570.

FIGS. 69 and 70 show the threaded component 568 (FIG. 70 showing the threaded component in section). As can be seen, the threaded component may be generally tubular in shape and includes a lumen 572 extending therethrough. Positioned generally midway between a first end 574 and a second end 576, on the outer surface 578, is a groove or channel 580 extending circumjacent the outer surface 578. The threaded component 568 may also include a pin or pins 584 extending radially from the outer surface 578.

Within the lumen 572 of the threaded component 578 are positioned helical (threaded) grooves 586 (seen particularly in FIG. 70). The grooves 586 extend completely around the inner diameter of the lumen 572.

FIG. 71 shows the base component 570 which is rotatably positioned partially over and through the threaded component 568. The base component 570 comprises a base or hub 590 and a base extension 594. The hub 590 and base extension 594 include a channel 596 extending therethrough. One or more bores 598 are positioned within the hub 590 and are sized and configured to restrain a pin 600. Two bores 598 are shown in FIG. 71. After the threaded component 568 is coupled to the base component 570, the pins 600 are inserted into the bores 598. The bores 598 are positioned to allow the inserted pins 600 to be positioned within the channel 580 on the threaded component 568. The pins 600 retain the base component 570 on the threaded component 568 yet allow for rotation of the threaded component 568 relative to the base component 570.

In use, the base component 570 is positioned over the grooved component 568, as can be seen in FIG. 68. When the bridging element 12 is to be adjusted, a catheter having a torquing tool 540 (as can be seen in FIG. 67 and described above) on its distal end is used to rotate the threaded component 568 in either a clockwise or counter-clockwise direction. The helical grooves 586 of the threaded component 568 engage the teeth 566 of the toothed ribbon 562, causing the toothed ribbon to thread through the bridge stop 560, which in turn lengthens or shortens the toothed ribbon 562 (bridging element). When a desired tension of the bridging element is achieved, the torquing tool 540 is removed.

It is to be appreciated that each embodiment of the bridge stop may be configured to have a bridge securing configuration in a static state, so as to require a positive actuation force necessary to allow the bridging element to move freely within or around the bridge stop. When a desirable tension in the bridge element is achieved, the actuation force may be removed, thereby returning the bridge stop back to its static state and securing the bridge stop to the bridging element. Alternatively, the bridge stop may be configured to allow free movement of the bridging element 12 in its static state, thereby requiring a positive securing force to be maintained on the bridge stop necessary to secure the bridging element within the bridge stop.

Preferably, the bridge securing feature is unambiguous via tactile or fluoroscopic feedback. The securing function preferably may be locked and unlocked several times, thereby allowing the bridging element to be readjusted. The bridge stop material is also desirably radio-opaque or incorporates radio-opaque features to enable the bridge stop to be located with fluoroscopy.

Figure 72:
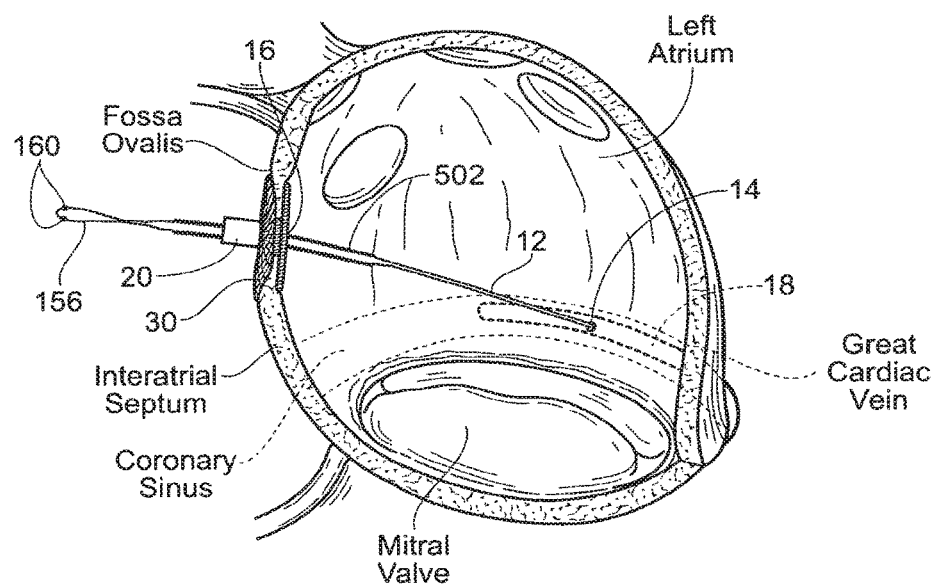
FIG. 72 is an anatomic anterior perspective view of the left atrium and a portion of the right atrium, with portions broken away and in section to show the presence of an alternative implant system of the type shown in FIGS. 10A to 10D, the alternative implant system includes a multiple element bridging element that spans the mitral valve annulus, and a relocation loop for removal or adjustment of the implant system.

As previously described, the bridging element 12 may comprise a single element, or may also comprise multiple elements. In numerous embodiments described above, the bridging element comprised multiple elements. FIG. 72 shows an example where the toothed ribbon 502 of the bridge stop 500 comprises a portion of the bridging element 12. As can be seen, the toothed ribbon 502, for example, extends through the bridge stop 500 and through a septal member 30, and is then coupled to a segment of bridging element 12. The toothed ribbon 502 may be coupled to the bridging element 12 by way of tying, gluing, crimping, welding, or machined from a single piece of material, as non-limiting examples.

Figure 73:
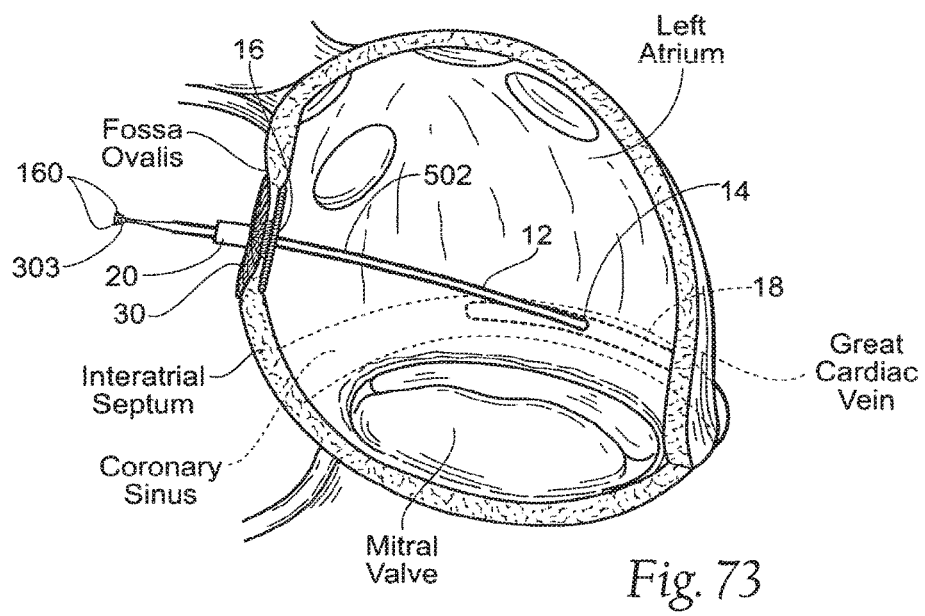
FIG. 73 is an anatomic anterior perspective view of the left atrium and a portion of the right atrium, with portions broken away and in section to show the presence of an alternative implant system of the type shown in FIGS. 10A to 10D, the alternative implant system includes toothed ribbon bridging element that spans the mitral valve annulus, and a relocation loop for removal or adjustment of the implant system.

In an alternative embodiment, the toothed ribbon 502, for example, may comprise the entire bridging element, as shown in FIG. 73. As can be seen, the toothed ribbon 502 extends through the bridge stop 500 and through a septal member 30, and continues through the left atrium to the posterior bridge stop region 14, where it is coupled to the posterior bridge stop 18.

A segment of bridging element 12 may also extend into the right atrium as shown in FIG. 72 to allow for retrieval of the implant system or adjustment of the bridging element. As can be seen, a segment of bridging element comprising an exposed loop 156 extends from the toothed ribbon 502. Radio-opaque markers 160 may be used to facilitate the grasping or snagging of the exposed loop 156.

In an alternative embodiment, the toothed ribbon 502 may comprise an in integral hook or loop 303 to allow for retrieval of the implant system or adjustment of the bridging element. Radio-opaque markers 160 may be used to facilitate the grasping or snagging of the exposed loop 303.

VI. Alternative T-Shaped Bridge Stop Embodiments

Alternative embodiments of T-shaped bridge stops may be used and are herein described. The T-shaped bridge stop may serve to secure the bridging element 12 (or alternative bridging element embodiments) at the anterior bridge stop region 16 or the posterior bridge stop region 14, or both. It is to be appreciated that the alternative embodiments of the T-shaped bridge stop may comprise a single element, or may also comprise multiple elements, as shown and described in FIGS. 43A and 43B, for example. It is also to be appreciated that the alternative embodiments of the T-shaped bridge stop devices may be symmetrical, or may also be asymmetrically shaped. In addition, the alternative embodiments of the T-shaped bridge stop may feature adjustment of the bridging element to tighten only, or to loosen and tighten.

Figure 74:
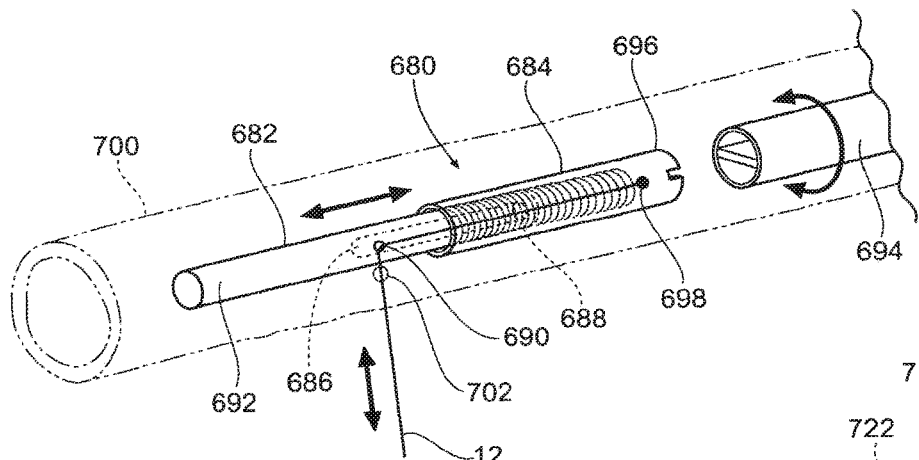
FIGS. 74 and 75 are perspective views of alternative embodiments of a T-shaped bridge stop or member of the type shown in FIGS. 10A to 10D, showing T-shaped bridge stops having a bridge element adjustment feature.

FIG. 74 is a perspective view of an alternative embodiment of a T-shaped bridge stop 680 in accordance with the present invention. The alternative T-shaped bridge stop 680 preferably includes an externally threaded male member 682 nested partially within an internally threaded female member 684. The male member 682 includes a tubular portion 686 extending from the end 688 that is positioned within the female member to about the middle of the male member 682, although the tubular portion 686 may extend past the middle of the male member, including extending the full length of the male member 682, or may extend less than to the middle of the male member. An aperture 690 is positioned in the male member 682 and extends from the outside surface 692 of the male member to the tubular portion 686.

In use, the T-shaped bridge stop 680 allows the length of the bridging element 12 to be adjusted by rotating the female member in either a clockwise or counterclockwise direction. As can be seen in FIG. 74, a catheter 694 may be used to couple to the end 696 of the female member 684 to provide rotation of the female member. Bridging element 12 is fixed at 698 within the female member 684, such that rotation of the female member 684 causes the overall length of the T-shaped bridge stop 680 to expand or contract, thereby adjusting the length of the bridging element 12. The T-shaped bridge stop 680 is shown positioned within the lumen of a vessel 700. The bridging element 12 extends from fixation point 698 through the tubular portion 686 of the male member, then through the aperture 690, and through the vessel wall at 702. The penetration of the bridging element 12 through the vessel wall at 702 and through aperture 690 stops the male portion 682 from rotating, thereby allowing rotation of the female member 684 to adjust the length of the bridging element 12.

Figure 75:
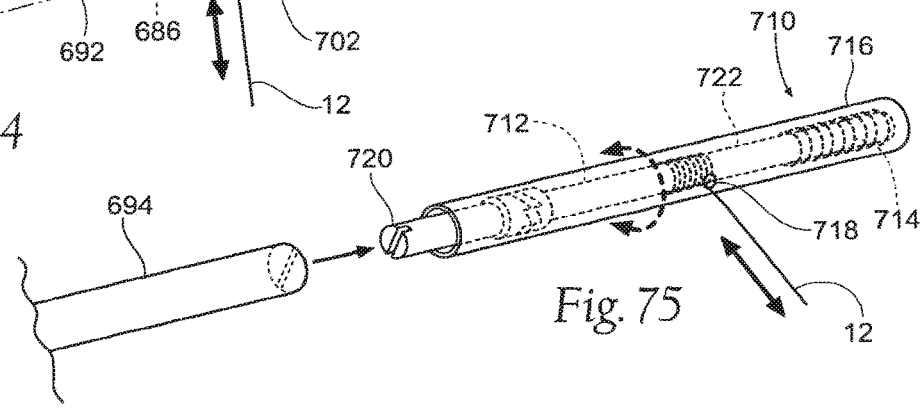

FIG. 75 is a perspective view of an alternative embodiment of a T-shaped bridge stop 710 in accordance with the present invention. The alternative T-shaped bridge stop 710 preferably includes a ratcheting mechanism 712 having a first member 720 and a second member 722 (e.g., ball point pen style mechanism), and a compression spring 714 working in cooperation with the ratcheting mechanism 712, both of which may be positioned within a tubular member 716. An aperture 718 is positioned generally midway the tubular member 716 (although other positions along the length of the bridge stop are possible) that allows the bridging element 12 to pass through the wall of the tubular member 716 and couple to the ratcheting mechanism 712.

In use, the T-shaped bridge stop 710 allows the length of the bridging element 12 to be adjusted by operation of the ratcheting mechanism 712. As can be seen in FIG. 75, a catheter 694 may be used to couple to the first member 720 of the ratcheting mechanism 712 to provide an axial force to the ratcheting mechanism, which in turn rotates the second member 722 of the ratcheting mechanism. Discrete segments of the bridging element 12 are allowed to be dispensed or retracted through aperture 718 when the first end 720 is pushed with the catheter 694. The catheter 694 may also release and reset any tension on the bridging element 12 by rotating the ratcheting mechanism 712. Rotation of the second member 722 causes the bridging element 12 to wrap around the second member 722, thereby adjusting the length of the bridging element 12. As shown in FIG. 74, the T-shaped bridge stop 710 may be positioned within a vessel or against an organ wall. The penetration of the bridging element 12 through the vessel wall and through aperture 718 stop the tubular member 716 from rotating, thereby allowing rotation of the second member 722 to adjust the length of the bridging element 12.

Figure 76:
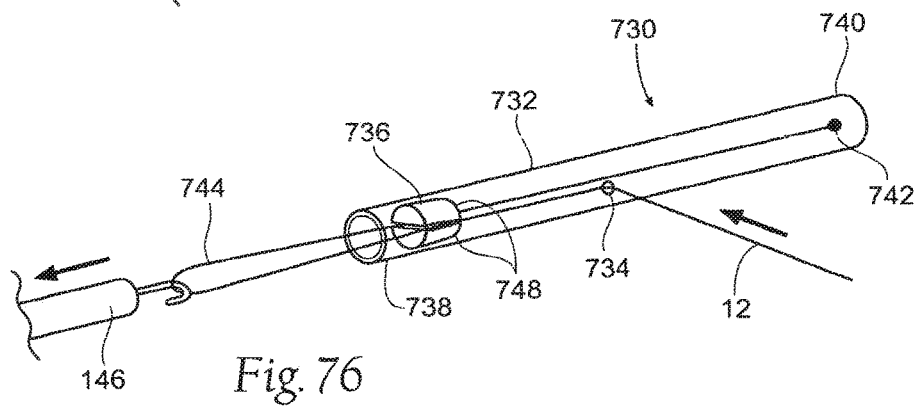
FIGS. 76 and 77 are perspective views of alternative embodiments of a T-shaped bridge stop or member of the type shown in FIGS. 10A to 10D, showing T-shaped bridge stops having a bridging element tensioning only feature.

FIG. 76 is a perspective view of an alternative embodiment of a T-shaped bridge stop 730 in accordance with the present invention. The alternative T-shaped bridge stop 730 preferably includes a tubular member 732 having an aperture 734, and a clamp 736 positioned within the tubular member 732. The aperture 734 is positioned generally midway the tubular member 732 (although other positions along the length of the bridge stop are possible) and the clamp 736 is positioned generally near a first end 738 of the tubular member. Within the tubular member 732, generally near the second end 740, the bridging element is coupled to the tubular member at fixation point 742.

In use, the T-shaped bridge stop 730 allows the length of the bridging element 12 to be shortened (increase in tension) by pulling on the exposed loop 744 of the bridging element 12 with a catheter having means for adjustment, such as a hooked tip 746. It is to be appreciated that additional means to couple to the exposed end of the bridging element 12 are contemplated as well, such as a clamp, loop, or magnetics, for example. As can be seen in FIG. 76, the catheter 746 is used to snag and then pull on the exposed loop 744. By pulling on the exposed loop, one leg of the bridging element 12 is pulled through the clamp 736. The pulling force must be greater than the clamping force of the clamp 736 so as to maintain the position of the bridging element within the clamp when the exposed loop 744 is released. The clamp 736 may include serrated jaws 748 to improve the ability of the clamp 736 to allow the bridging element 12 to be pulled through it for increasing tension, yet not allow the tension on the bridging element 12 to pull the bridging element back through the clamp 736 (which would cause a decrease in tension).

Figure 77:
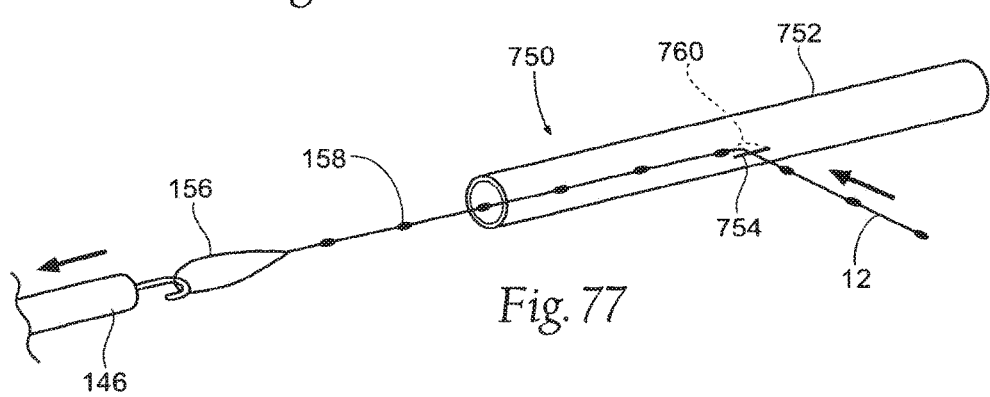

FIG. 77 is a perspective view of an alternative embodiment of a T-shaped bridge stop 750 in accordance with the present invention. The alternative T-shaped bridge stop 750 preferably includes a tubular member 752 having a slit 754. The slit 754 is positioned generally midway the tubular member 752, although other positions along the length of the bridge stop are possible.

In use, the T-shaped bridge stop 750 allows the length of the bridging element 12 to be shortened (increase in tension) by pulling on the exposed loop 756 of the bridging element 12 with an adjustment catheter having a hooked tip 146, for example. As can be seen in FIG. 77, in this embodiment, the bridging element 12 includes discrete bead or stop elements 158. The catheter 146 is used to snag and then pull on the exposed loop 156. By pulling on the exposed loop, the bridging element 12, including the discrete stop elements 158, is pulled through the slit 754. The slit 754 allows the beads to be pulled into the tubular member 752, but not out of the tubular member. The slit 754 may include flaps 760 (e.g., as in a duck bill valve) to help maintain the tension on the bridging element 12 and to keep the discrete stop elements 158 from being pulled out of the tubular member 752 by the tension on the bridging element 12. The discrete stop elements 158 may be positioned apart from each other at predefined lengths (e.g., about 2 mm to about 5 mm), so as to allow shortening of the bridging element at these predefined lengths.

VII. Alternative Bridging Element Embodiments

Alternative embodiments of bridging elements may be used and are herein described. The bridging element may serve to secure the anterior bridge stop region 16 to the posterior bridge stop region 14. It is to be appreciated that the alternative embodiments of the bridging element may comprise a single element, or may also comprise multiple elements.

Figure 78:
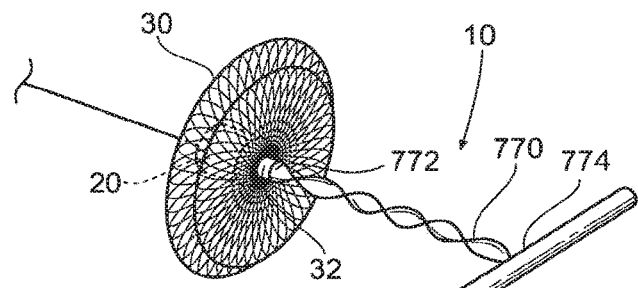
FIG. 78 is a perspective view depicting an alternative embodiment of an implant system of the type shown in FIGS. 10A to 10D, showing the use a ribbon bridging element.

FIG. 78 is a perspective view of an alternative embodiment of an implant system 10 having a bridging element 770 in accordance with the present invention. The bridging element 770 having a first end 772 and a second end 774 is shown extending through a septal member 30 and coupled to a posterior bridge stop 18. The bridging element may also couple to the septal member 30. Bridging element 770 desirably comprises a ribbon of material having ductile properties (i.e., capable of being shaped, bent, or drawn out), such as stainless steel. By twisting the bridging element 770, which may be accomplished at the posterior bridge stop region 14 and/or the anterior bridge stop region 16, the bridging element shortens or lengthens, and because the bridging element yields, it stays at the desired length. The twisting force necessary to adjust the bridging element 770 is greater than the tension force on the bridging element. The twisting may be accomplishes with an adjustment catheter (not shown).

Figure 79:
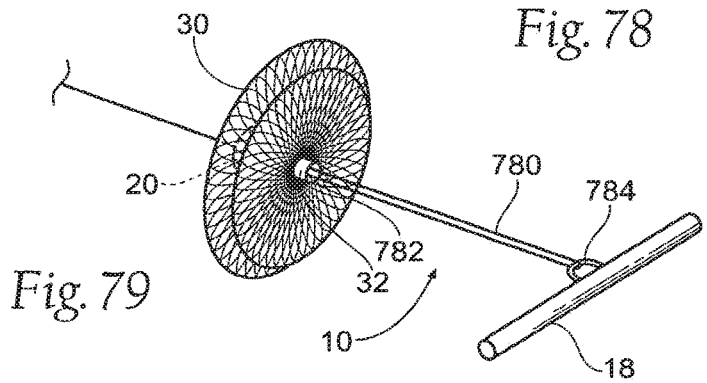
FIG. 79 a perspective view depicting an alternative embodiment of an implant system of the type shown in FIGS. 10A to 10D, showing the use a looped bridging element.

FIG. 79 is a perspective view of an additional alternative embodiment of an implant system 10 having a bridging element 780 in accordance with the present invention. The bridging element 780 is shown extending through a septal member 30 and coupled to a posterior bridge stop 18. The bridging element may also couple to the septal member 30. Bridging element 780 desirably comprises at least one loop of bridging element. The first end 782 of bridging element 780 may be coupled to the septal member 30, or alternatively coupled to the anterior bridge stop 20, or alternatively, coupled to the grommet 32. From the first end 782, the bridging element loops around a hook or retainer 784 coupled to the posterior bridge stop 18 and then extends back to and through the septal member 30. The looped bridging element 780 doubles the length of the bridging element, and in doing so allows for a finer adjustment of the implant system 10 because of the improved pulling ratio of ½ unit to 1 unit.

Figure 80A:
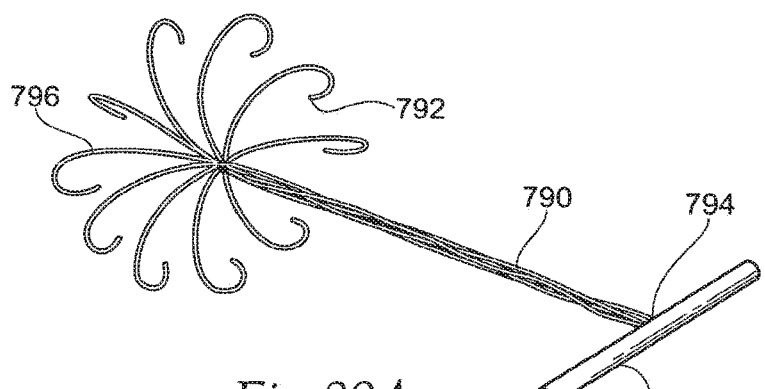
FIG. 80A is a perspective view depicting an alternative embodiment of an implant system of the type shown in FIGS. 10A to 10D, showing the use a braided bridging element including curved ends on the anterior side and forming an anterior bridge stop.
Figure 80B:
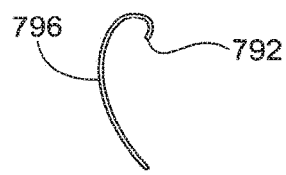
FIG. 80B is a side view of a curved end of the braided bridging element of FIG. 80A, showing the curved end in one state of curvature.
Figure 80C:
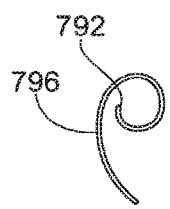
FIG. 80C is a side view of the curved end of the braided bridging element of FIG. 80A, showing the curved end in an additional state of curvature.

FIG. 80A is a perspective view of an additional alternative embodiment of an implant system 10 having a bridging element 790 in accordance with the present invention. The bridging element 790 having a first end 792 and a second end 794 is shown having an integral anterior bridge stop 26 and also coupled to a posterior bridge stop 18. It is to be appreciated that the bridging element 790 may have an integral posterior bridge stop, or may have both an integral anterior and posterior bridge stop as well. Bridging element 790 desirably comprises braided Nitinol wires having a predefined length. The braided Nitinol wires are desirably left straight for a predefined range (e.g., about 8 cm to about 10 cm). A predefined portion of the braided Nitinol wires (e.g., about 1 cm to about 3 cm), are pre-shaped to curl into an anterior bridge stop 796 when released from a delivery catheter in the right atrium. FIGS. 80B and 80C show varying configurations of the first end 792 (i.e., the anterior bridge stop 796), as tension on the bridging element 790 increases (see FIG. 80B) or decreases (see FIG. 80C).

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of adjusting a length of a bridging element of an implant comprising:
providing a bridge stop having a housing with a length and a width and an aperture extending through the length of the bridge stop housing, the aperture sized and configured to allow a bridging element to extend through at least a portion of the length of the aperture, and an adjustment mechanism coupled to the bridge stop to allow adjustment of the length of the bridging element;
operating the adjustment mechanism to lengthen or to shorten the bridging element;
repeating the operating the adjustment mechanism to lengthen or shorten the bridging element until a desired length of the bridging element is achieved; and
allowing the bridging element to settle for at least a predetermined time before repeating the operating the adjustment mechanism step.

2. The method of claim 1 further including:
repeating the operating the adjustment mechanism to lengthen or shorten the bridging element until a desired length of the bridging element is achieved.

3. The method of claim 1 further comprising:
placing the bridging element across a chamber of a human heart; and
adjusting the bridge stop to place the bridging element in tension.

4. A method of adjusting a length of a bridging element of an implant comprising:
providing a bridge stop having a housing with a length and a width and an aperture extending through the length of the bridge stop housing, the aperture sized and configured to allow a bridging element to extend through at least a portion of the length of the aperture, and an adjustment mechanism coupled to the bridge stop to allow adjustment of the length of the bridging element;
operating the adjustment mechanism to lengthen or to shorten the bridging element; and
coupling a catheter to the bridge stop, the catheter being used to operate the adjustment mechanism.

5. A method of adjusting a length of a bridging element of an implant comprising:
providing a bridge stop having a housing with a length and a width and an aperture extending through the length of the bridge stop housing, the aperture sized and configured to allow a bridging element to extend through at least a portion of the length of the aperture, and an adjustment mechanism coupled to the bridge stop to allow adjustment of the length of the bridging element;
operating the adjustment mechanism to lengthen or to shorten the bridging element;
placing the bridging element across a chamber of a human heart;

adjusting the bridge stop to place the bridging element in tension;
allowing the heart to settle for at least a period of time after adjusting the bridge stop to place the bridging element in tension; and
imaging the heart to determine heart function.

6. The method of claim 5 further comprising:
securing the adjustment mechanism to fix the bridge stop to the bridging element based on the imaging of the heart indicating a desired heart function.

7. The method of claim 5 further comprising:
adjusting the bridge stop to shorten or lengthen the bridging element based on the imaging of the heart; and
allowing the heart to settle for at least the period of time after adjusting the bridge stop to shorten or lengthen the bridging element; and
imaging the heart to determine heart function after allowing the heart to settle for at least the period of time.

8. The method of claim 7 further comprising:
secure the adjustment mechanism to fix the bridge stop to the bridging element based on the imaging of the heart indicating a desired heart function.

9. The method of claim 5 wherein imaging the heart comprises any of: fluoroscopy, ultrasound, magnetic resonance, computed tomography, or any combination thereof.

10. A method of adjusting a bridge stop in deployment of an implant in a heart of a patient, the heart having a valve annulus, the method comprising:
placing the implant in the heart of the patient such that a bridging element spans at least a portion of a chamber of the patient's heart between a posterior anchor and an anterior anchor, the anterior anchor having the bridge stop with an adjustment mechanism being operable between a restrained configuration that restrains movement of the bridging element through the bridge stop and an unrestrained configuration that allows movement of the bridging element through the bridge stop;
adjusting a length of the bridging element between the anterior and posterior anchors while the adjustment mechanism is in the unrestrained configuration;
activating the adjustment mechanism from the unrestrained configuration to the restrained configuration while the bridging element is in tension to fix the length of the bridging element at a first length;
allowing passage of at least a period of time for the heart to settle after adjusting the length of the bridging element to the first length while the adjustment mechanism is in the restrained configuration; and
imaging the heart after the period of time while the adjustment mechanism is in the restrained configuration at the first length of the bridging element so as to determine heart function.

11. The method of claim 10, further comprising:
locking the bridge stop when the determined heart function corresponds to a desired heart function.

12. The method of claim 10, further comprising:
releasing the adjustment mechanism from the restrained to the unrestrained configuration, re-adjusting the length of the bridging element to a second length different from the first length when the determined heart function does not correspond to a desired heart function;
allowing passage of at least the period of time for the heart to settle after adjusting the length of the bridging element to the second length while the adjustment mechanism is in the restrained configuration; and
imaging the heart after the period of time while the adjustment mechanism is in the restrained configuration at the second length of the bridging element so as to determine heart function.

13. The method of claim 10 wherein activating the adjustment mechanism comprises operating a catheter releasably coupled to the bridge stop.

14. The method of claim 10 further comprising deploying the bridge stop, at least in part, in a chamber adjacent to the chamber which the bridging element spans.

15. The method of claim 10 further comprising:
deploying the bridge stop at least in part in the right atrium and deploying the posterior anchor at least in part within the great cardiac vein so that the bridging mechanism spans at least a portion of the left atrium so as to reshape the left atrium for treatment of a mitral valve annulus.

16. The method of claim 15 wherein the bridge stop is deployed at least in part in contact with a septum between the left and the right atrium.

17. The method of claim 16 wherein the bridge stop is deployed in contact with a fossa ovalis portion of the septum.

18. The method of claim 10 wherein the adjustment mechanism comprises a clamp engageable with a plurality of stop elements disposed along an anterior portion of the bridging element such that activating the adjustment mechanism from the unrestrained configuration to the restrained configuration comprises activating the clamp to clamp down on the anterior portion of the bridging element posterior along or adjacent to at least one stop element of the plurality of stop elements.

19. The method of claim 18 further comprising:
releasing the adjustment mechanism from the restrained configuration to the unrestrained configuration by releasing the clamp from the anterior portion of the bridging element to facilitate re-adjusting the length of the bridging element.

20. The method of claim 10 wherein the adjustment mechanism comprises a toothed ribbon in conjunction with a locking collar, the locking collar being adjustable between a locked position wherein the collar is locked against the teeth in the ribbon and an unlocked position wherein the ribbon is free to slide within the locking collar.

21. The method of claim 10 wherein the adjustment mechanism comprises a locking collar engageable with a plurality of discrete stops of an anterior portion of the bridging element, the locking collar having a ramp therein with a slot therethrough, the slot having a narrow section and an enlarged section, the enlarged section sized for passage of the discrete to allow shortening or lengthening of the bridging element and the narrow section sized to inhibit passage of the discrete stops to lock the length of the bridging element, wherein the step of activating the adjustment mechanism from the unrestrained configuration to the restrained configuration comprising moving the anterior portion of the bridging element from the enlarged section to the narrow section.

22. The method of claim 10 wherein the heart of the patient includes a great cardiac vein, and the posterior anchor comprises a T-bar such that placing the implant in the heart of the patient comprises placing the posterior anchor within the great cardiac vein.

23. The method of claim 10 wherein the heart of the patient has a great cardiac vein, and the posterior anchor comprises a stent such placing the implant in the heart comprises deploying the stent in the great cardiac vein.

24. A method of adjusting a bridge stop in deployment of an implant in a heart of a patient, the heart having a valve annulus, the method comprising:

placing the implant in the heart of the patient such that a bridging element spans at least a portion of a chamber of the patient's heart between a posterior anchor and an anterior anchor, the anterior anchor having the bridge stop with an adjustment mechanism being operable between a restrained configuration that restrains movement of the bridging element through the bridge stop and an unrestrained configuration that allows movement of the bridging element through the bridge stop;

adjusting a length of the bridging element between the anterior and posterior anchors while the adjustment mechanism is in the unrestrained configuration; and activating the adjustment mechanism from the unrestrained configuration to the restrained configuration while the bridging element is in tension to fix the length of the bridging element at a first length, wherein the adjustment mechanism comprises a toothed ribbon in conjunction with a locking collar, the locking collar being adjustable between a locked position wherein the collar is locked against the teeth in the ribbon and an unlocked position wherein the ribbon is free to slide within the locking collar, wherein the locking collar is changed from the unlocked position to the locked position by means of rotating at least a portion of the locking collar.

25. A method of adjusting a bridge stop in deployment of an implant in a heart of a patient, the heart having a valve annulus, the method comprising:

placing the implant in the heart of the patient such that a bridging element spans at least a portion of a chamber of the patient's heart between a posterior anchor and an anterior anchor, the anterior anchor having the bridge stop with an adjustment mechanism being operable between a restrained configuration that restrains movement of the bridging element through the bridge stop and an unrestrained configuration that allows movement of the bridging element through the bridge stop;

adjusting a length of the bridging element between the anterior and posterior anchors while the adjustment mechanism is in the unrestrained configuration; and activating the adjustment mechanism from the unrestrained configuration to the restrained configuration while the bridging element is in tension to fix the length of the bridging element at a first length, wherein the adjustment mechanism comprises an anterior portion of the bridging element having toothed projections and a bridge lock adjustment screw, the bridge lock adjustment screw having an interior bore with helical grooves thereon that mate with the toothed projections, wherein the step of activating the adjustment mechanism comprises rotating the bridge lock adjustment screw relative to the toothed portion of the bridging element.

* * * * *